US012424426B2

(12) United States Patent
Hahn et al.

(10) Patent No.: US 12,424,426 B2
(45) Date of Patent: Sep. 23, 2025

(54) BENZYLPYRIDINIUM REAGENT FOR MASS SPECTROMETRY

(71) Applicant: Roche Diagnostics Operations, Inc., Indianapolis, IN (US)

(72) Inventors: Robert Hahn, Munich (DE); Dieter Heindl, Munich (DE); Thomas Hoffmann, Bad Heilbrunn (DE); Hans-Peter Josel, Weilheim (DE); Uwe Kobold, Weilheim (DE); Hannes Kuchelmeister, Munich (DE); Simon Ferdinand Loibl, Wolfratshausen (DE); Daniela Mazzier, Munich (DE); Jelena Milic, Penzberg (DE); Giuseppe Prencipe, Penzberg (DE); Martin Rempt, Penzberg (DE); Christoph Seidel, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 497 days.

(21) Appl. No.: 17/990,714

(22) Filed: Nov. 20, 2022

(65) Prior Publication Data
US 2023/0127289 A1    Apr. 27, 2023

Related U.S. Application Data

(63) Continuation of application No. PCT/EP2021/063296, filed on May 19, 2021.

(30) Foreign Application Priority Data

May 20, 2020   (EP) .................................... 20175801

(51) Int. Cl.
*H01J 49/00*        (2006.01)

(52) U.S. Cl.
CPC ............................ *H01J 49/0031* (2013.01)

(58) Field of Classification Search
USPC ........................................................ 250/282
See application file for complete search history.

(56) References Cited

U.S. PATENT DOCUMENTS

| 11,764,043 B2 * | 9/2023 | Senko ................ G01N 33/6848 250/282 |
| 2004/0157344 A1 * | 8/2004 | Wang ................. G01N 33/6848 556/415 |
| 2017/0305861 A1 | 10/2017 | Kim et al. |

FOREIGN PATENT DOCUMENTS

| JP | H05170737 A | 7/1993 |
| JP | H05262813 A | 10/1993 |
| JP | H08208609 A | 8/1996 |
| JP | H11508570 A | 7/1999 |
| JP | 2007132741 A | 5/2007 |

(Continued)

OTHER PUBLICATIONS

Barrio et al., Specific and Fluorescent Modifications of Cytidine, J Am Chem Soc, (1973), pp. 1323-1328, vol. 95 Issue 4.

(Continued)

*Primary Examiner* — Kiet T Nguyen
(74) *Attorney, Agent, or Firm* — Taft Stettinius & Hollister LLP

(57) ABSTRACT

The present invention relates to compounds which are suitable to be used in mass spectrometry as well as methods of mass spectrometric determination of analyte molecules using said compounds.

14 Claims, 2 Drawing Sheets

(56) References Cited

FOREIGN PATENT DOCUMENTS

| JP | 2013518258 | A | 5/2013 |
|---|---|---|---|
| JP | 2015508504 | A | 3/2015 |
| JP | 2019510204 | A | 4/2019 |
| WO | 9955677 | A1 | 11/1999 |
| WO | 2010123919 | A2 | 10/2010 |
| WO | 2011091436 | A1 | 7/2011 |
| WO | 2015123355 | A1 | 8/2015 |
| WO | 2019213570 | A1 | 11/2019 |
| WO | 2020020850 | A1 | 1/2020 |
| WO | 2021234003 | A1 | 11/2021 |

OTHER PUBLICATIONS

Bran, Synthesis of 4+Pyridyl)oxazoles , Tetrahedron, (1994), pp. 10061-10072, vol. 50 Issue 33.
Buckley et al., Reactions of Charged Substrates. 4. The Gas-Phase Dissociation of (4-Substituted benzyl) dimethylsulfoniums and -pyridiniums, J Org Chem, (1996), pp. 2753-2762, vol. 61 Issue 8.
Katritzky et al., Intramolecular Reactions of Pyridinium-2-carbonyl Azides: Conversion of Amines into Aldehydes, J Chem Soc Perkin Trans 1, (1982), pp. 2953-2956.
Renom-Carrasco et al., Asymmetric Hydrogenation of 3-Substituted Pyridinium Salts, Chem A Europ J Comm, (2016), pp. 9528-9532, vol. 22 Issue 28.
Wu et al., Efficient and Chemoselective Reduction of Pyridines to Tetrahydropyridines and Piperidines via Rhodium-Catalyzed Transfer Hydrogenation, Adv Synt Catal, (2013), pp. 35-40, vol. 355 Issue 1.
Yong-Tae et al., Photocyclization Mechanism of Halopyridinium Salt Tethered to Arene: Flash Photolysis Observation of a Pyridinium ó, Cyclohexadienyl Radicals, and a Dihalide Radical Anion in Aqueous Solution, J Am Chem Soc, (1997), pp. 10677-10683, vol. 119 Issue 44.
International Search Report, European Patent Office; International Application No. PCT/EP2021/063296; Sep. 22, 2021; 5 pages.
Written Opinion of the International Searching Authority; European Patent Office; International Application No. PCT/EP2021/063296; Sep. 22, 2021; 7 pages.
Ban, Hitoshi et al., Tyrosine Bloconjugation through Aqueous Ene-Type Reactions: A Click-Like Reaction for Tyrosine, Journal of the American Chemical Society, 2010, pp. 1523-1525, vol. 132.
Beaudry, Francis et al., Development of a rapid and sensitive LC-ESI/MS/MS assay for the quantification of propofol using a simple off-line dansyl chloride derivatization reaction to enhance signal intensity, Journal of Pharmaceutical and Biomedical Analysis, 2005, pp. 411-417, vol. 39.
Frey, Alexander J. et al., Validation of highly sensitive simultaneous targeted and untargeted analysis of keto-steroids by Girard P derivatization and stable isotope dilution-liquid chromatography-high resolution mass spectrometry, Steroids, 2016, pp. 60-66, vol. 116.
Higashi, Tatsuya et al., Chemical derivatization for enhancing sensitivity during LC/ESI-MS/MS quantification of steroids in biological samples: a review, Journal of Steroid Biochemistry & Molecular Biology, 2016, pp. 57-69, vol. 162.
Higashi, Tatsuya et al., Isotope-coded ESI-enhancing derivatization reagents for differential analysis, quantification and profiling of metabolites in biological samples by LC/MS: A review, Journal of Pharmaceutical and Biomedical Analysis, 2016, pp. 181-193, vol. 130.
Hong, Haizheng et al., Derivatization with Girard Reagent T Combined with LC-MS/MS for the Sensitive Detection of 5-Formyl-2'-deoxyuridine in Cellular DNA, Analytical Chemistry, 2007, pp. 322-326, vol. 79, No. 1.
Rahimoff, René et al., 5-Formyl- and 5-Carboxydeoxycytidines Do Not Cause Accumulation of Harmful Repair Intermediates in Stem Cells, Journal of the American Chemical Society, 2017, p. 10359-10364, vol. 139.
Alley, William, RapiFluor-MS labeled glycan analysis for biotherapeutic proteins, 28th International Carbohydrate Symposium, 2016, Abstract only.
Japanese Office Action, Japan Patent Office, Japanese Patent Application No. 2022-570541, May 7, 2025.
Serban, Georgeta et al.: Synthetic Studies of Substituted Pyridine Aldehydes as Intermediates for the Synthesis of Toddaquinoline, Its Derivatives and Other Natural Products, Heterocycles, vol. 83, No. 9, 2011, pp. 1989-2000, DOI: 10.3987/COM-11.12239.
Bennesar, M.-L. et al.: Addition of Ester Enolatess To N-ALKYL-2-Fluoropyridinium Salts Total Synthesis of (+−)-20-DEOXYCAMPTOTHECIN and (+)-Camptothecin, J. Org. Chem., 2002, 67, 7465-7474.
Fozard, Alan et al.: The Synthesis of the Pyrido [2,1~a]Isoindole System By an Intramolecular Photochemical Cyclization, J. org. Chem., 1967, 32, 2966-2969.

* cited by examiner

Rating based on a LOD enhancement factor

BENZYLPYRIDINIUM REAGENT FOR MASS SPECTROMETRY

CROSS-REFERENCE TO RELATED APPLICATIONS

This application is a continuation of International PCT Application No. PCT/EP2021/063296 filed on May 19, 2021, which claims priority to European Patent Application No. 20175801.8 filed on May 20, 2020, the contents of each application are incorporated herein by reference in their entireties.

FIELD OF THE INVENTION

The present invention relates to compounds, compositions comprising said compounds, kits comprising said compositions and/or compounds and a complex which are suitable to be used in mass spectrometry. Further, the present invention relates to a method of mass spectrometric determination of analytes using said compounds.

BACKGROUND OF THE INVENTION

Mass spectrometry (MS) is a widely used technique for the qualitative and quantitative analysis of chemical substances ranging from small molecules to macromolecules. In general, it is a very sensitive and specific method, allowing even for the analysis of complex biological, e.g. environmental or clinical samples. However, for several analytes, especially if analysed from complex biological matrices such as serum, sensitivity of the measurement remains an issue.

Often MS is combined with chromatographic techniques, particularly gas and liquid chromatography such as e.g. HPLC. Here, the analysed molecule (analyte) of interest is separated chromatographically and is individually subjected to mass spectrometric analysis (Higashi et al. (2016) J. of Pharmaceutical and Biomedical Analysis 130 p. 181-190).

There is, however, still a need of increasing the sensitivity of MS analysis methods, particularly for the analysis of analytes that have a low abundance or when only little materials (such as biopsy tissues) are available.

In the art, several derivatization reagents (compounds) are known which aim to improve the sensitivity of the measurement for these analytes. Amongst others, reagents comprising charged units and neutral loss units which are combined in a single functional unit (e.g. WO 2011/091436 A1). Other reagents comprising separate units are structurally relatively large which effects the general workflow of sample preparation and the MS measurement (Rahimoff et al. (2017) J. Am. Chem. Soc. 139(30), p. 10359-10364). Known derivatization reagents are for example dansylchloride, RapiFluor-MS (RFMS), Cookson-type reagents, Amplifex Diene, Amplifex Keto, Girard T, Girard P, Pyridiyl amine (Hong and Wang, Anal Chem., 2007, 79(1): 322-326; Frey et al., Steroids, 2016 December, 116:60-66; Francis et al., Journal of Pharmaceutical and Biomedical Analysis, 2005, 39(3-4), 411-417; Alley William, 28th International Carbohydrate Symposium, New Orleans, LA, United States, Jul. 17-21 (2016), ICS-209). All of these bear disadvantages due to often insufficient labelling efficiencies, generation of structural isomers due to coupling chemistry, non-optimal ionization efficiencies, disadvantages for chromatographic separation after coupling, non-optimal fragmentation behaviour due to many fragmentation pathways and need for high collision energies.

There is thus an urgent need in the art for a derivatization reagents which allows for a sensitive detection of analytes from complex biological matrices as well as exhibiting a chemical structure which does not negatively influence the MS measurement workflow. This is of particular importance in a random-access, high-throughput MS set up, wherein several different analytes exhibiting different chemical properties have to be measured in a short amount of time.

The present invention relates to a novel reagent (compound) which allows for a sensitive determination of analyte molecules such as steroids, proteins, and other types of analytes, in biological samples. The reagent is designed in a modular manner to allow the individual adaption for specific needs arising in the measurement of certain analytes or for specific workflow adaptations.

It is an object of the present invention to provide a compound of formula I, a kit and a composition each of these comprises said compound for efficiently detection of an analyte by mass spectrometric determination. Furthermore, an object of the present invention is to provide a complex and a method for mass spectrometric determination of an analyte.

This object or these objects is/are solved by the subject matter of the independent claims. Further embodiments are subjected to the dependent claims.

SUMMARY OF THE INVENTION

In the following, the present invention relates to the following aspects:

In a first aspect, the present invention relates to a compound of formula I for mass spectrometric determination of an analyte.

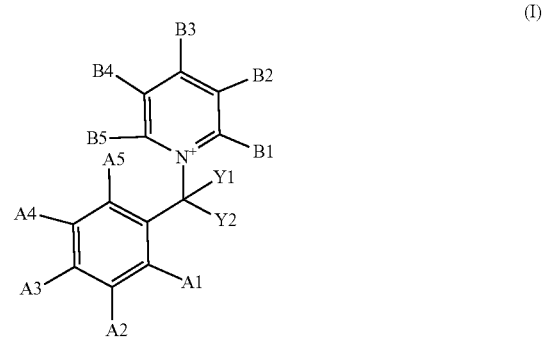

(I)

wherein one of the substituents B1, B2, B3, B4, B5 is a coupling group Q, which is capable of forming a covalent bond with the analyte, wherein the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof, wherein Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

In a second aspect, the present invention relates to a composition comprising the compound of the first aspect of the present invention.

In a third aspect, the present invention relates to a kit comprising the compound of the first aspect of the present invention or the composition of the second aspect of the present invention.

In a fourth aspect, the present invention relates to a complex for detecting an analyte using mass spectrometry comprising a binding analyte and a binding compound, which are covalently linked to each other, in particular wherein the complex is formed by chemical reaction of the analyte and the compound of the second aspect of the invention.

In a fifth aspect, the present invention relates to a use of the compound of the first aspect of the present invention for mass spectrometric determination of the analyte.

In a sixth aspect, the present invention relates to a method for mass spectrometric determination of an analyte comprising the steps of:
(a) reacting the analyte with the compound of formula I of the first aspect of the present invention, whereby a complex of the fourth aspect of the present invention is formed,
(b) subjected the complex from step (a) to a mass spectrometric analysis.

In a seventh aspect, the present invention relates to compound of formula V:

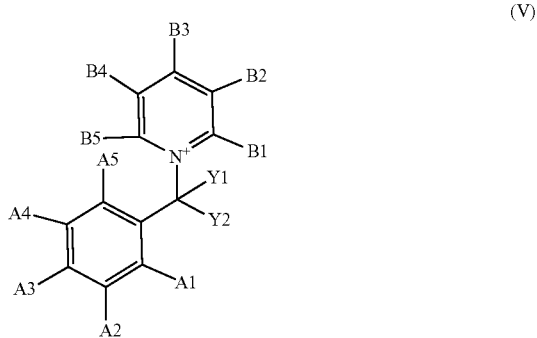

(V)

wherein one of the substituents B1, B2, B3, B4, B5 is a coupling group Q, which is capable of forming a covalent bond with the analyte,
wherein the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof,
wherein Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

LIST OF FIGURES

DETAILED DESCRIPTION OF THE INVENTION

Figure 1:
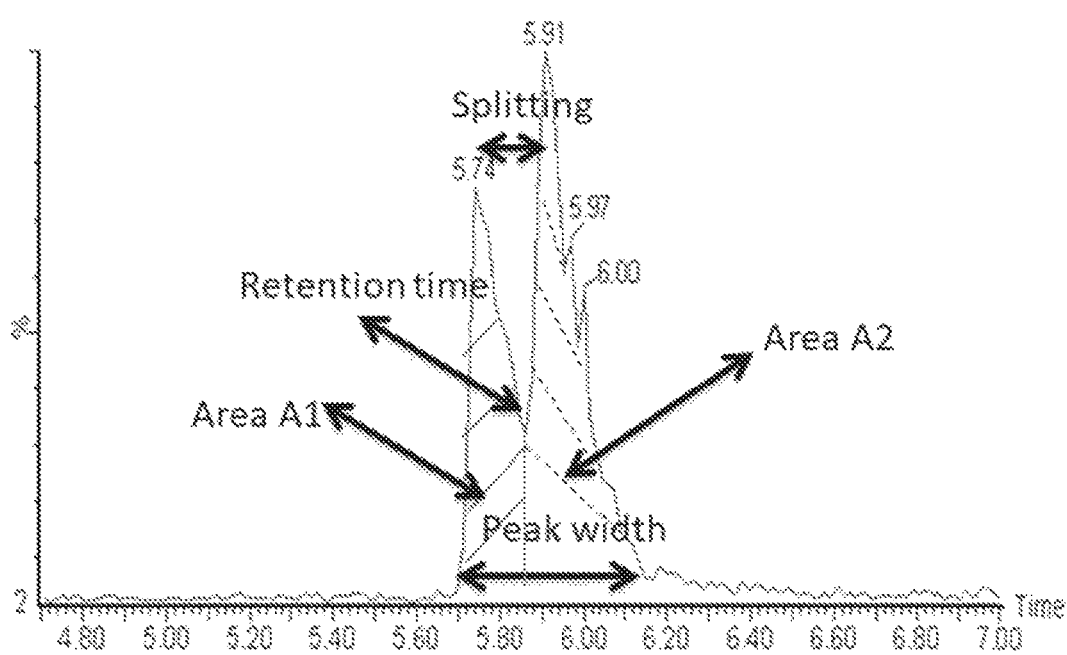
FIG. 1 shows the schematic illustration of peak "splitting": It describes the capability of the chromatographic system to separate the different isomers resulting from the derivatization reaction of the analyte molecule from each other.

Before the present invention is described in detail below, it is to be understood that this invention is not limited to the particular embodiments and examples described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The various described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4% to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%, 5-15%, 10-20%, etc. This same principle applies to ranges reciting minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

In the context of the present invention, the term "compound" refers to a chemical substance having a specific chemical structure. Said compound may comprise one or more reactive groups. Each reactive group may fulfil a different functionality, or two or more reactive groups may fulfil the same function. Reactive groups include but are not limited to reactive units, charged units, and neutral loss units. The compound can be named as label. In the context of the present invention, the term "binding compound" refers to the said compound, which is bonded to the analyte. In principle, the compound and the binding compound can be identical. The compound and the binding compound can be substantially identical. Substantially identical can mean that both compounds have an identical chemical structure with the exception that they differ from each other by the structure of the reactive unit K and/or the structure of the coupling group Q. Preferably, the compound is capable of forming a binding to the analyte, but is not yet bounded to the analyte. The binding compound is bounded to the analyte.

The term "Mass Spectrometry" ("Mass Spec" or "MS") or "mass spectrometric determination" relates to an analytical technology used to identify compounds by their mass. MS is a methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). The term "ionization" or "ionizing" refers to the process of generating an analyte ion having a net electrical charge equal to one or more electron units. Negative ions are those having a net negative charge of one or more electron units, while positive ions are those having a net positive charge of one or more electron units. The MS method may be performed either in "negative ion mode", wherein negative ions are generated and detected, or in "positive ion mode" wherein positive ions are generated and detected.

"Tandem mass spectrometry" or "MS/MS" involves multiple steps of mass spectrometry selection, wherein fragmentation of the analyte occurs in between the stages. In a tandem mass spectrometer, ions are formed in the ion source and separated by mass-to-charge ratio in the first stage of mass spectrometry (MS1). Ions of a particular mass-to-charge ratio (precursor ions or parent ion) are selected and fragment ions (or daughter ions) are created by collision-induced dissociation, ion-molecule reaction, or photodissociation. The resulting ions are then separated and detected in a second stage of mass spectrometry (MS2).

Since a mass spectrometer separates and detects ions of slightly different masses, it easily distinguishes different isotopes of a given element. Mass spectrometry is thus, an important method for the accurate mass determination and characterization of analytes, including but not limited to low-molecular weight analytes, peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

Most sample workflows in MS further include sample preparation and/or enrichment steps, wherein e.g. the analyte(s) of interest are separated from the matrix using e.g. gas or liquid chromatography. Typically, for the mass spectrometry measurement, the following three steps are performed:

1. a sample comprising an analyte of interest is ionized, usually by complex formation with cations, often by protonation to cations. Ionization source include but are not limited to electrospray ionization (ESI) and atmospheric pressure chemical ionization (APCI).
2. the ions are sorted and separated according to their mass and charge. High-field asymmetric-waveform ion-mobility spectrometry (FAIMS) may be used as ion filter.
3. the separated ions are then detected, e.g. in multiple reaction mode (MRM), and the results are displayed on a chart.

The term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyser by use of a set of differentially pumped skimmer stages. A counterflow of dry and preheated nitrogen gas may be used to improve removal of solvent. The gas-phase ionization in APCI can be more effective than ESI for analysing less-polar entity.

"High-field asymmetric-waveform ion-mobility spectrometry (FAIMS)" is an atmospheric pressure ion mobility technique that separates gas-phase ions by their behavior in strong and weak electric fields.

"Multiple reaction mode" or "MRM" is a detection mode for a MS instrument in which a precursor ion and one or more fragment ions are selectively detected.

Mass spectrometric determination may be combined with additional analytical methods including chromatographic methods such as gas chromatography (GC), liquid chromatography (LC), particularly HPLC, and/or ion mobility-based separation techniques.

In the context of the present disclosure, the term "analyte", "analyte molecule", or "analyte(s) of interest" are used interchangeably referring the chemical species to be analysed via mass spectrometry. Chemical species suitable to be analysed via mass spectrometry, i.e. analytes, can be any kind of molecule present in a living organism, include but are not limited to nucleic acid (e.g. DNA, mRNA, miRNA, rRNA etc.), amino acids, peptides, proteins (e.g. cell surface receptor, cytosolic protein etc.), metabolite or hormones (e.g. testosterone, estrogen, estradiol, etc.), fatty acids, lipids, carbohydrates, steroids, ketosteroids, secosteroids (e.g. Vitamin D), molecules characteristic of a certain modification of another molecule (e.g. sugar moieties or phosphoryl residues on proteins, methyl-residues on genomic DNA) or a substance that has been internalized by the organism (e.g. therapeutic drugs, drugs of abuse, toxins, etc.) or a metabolite of such a substance. Such analyte may serve as a biomarker. In the context of present invention, the term "biomarker" refers to a substance within a biological system that is used as an indicator of a biological state of said system. In the context of the present invention, the term "binding analyte" refers to the said analyte, which is bonded to the compound for forming a complex. In principle, the analyte and the binding analyte can be identical. The analyte and the binding analyte can be substantially identical. Substantially identical can mean that both analytes have an identical chemical structure with the exception that they differ from each other by the structure of the functional group. Preferably, the analyte is capable of forming a binding to the compound, but is not yet bounded to the compound. The binding analyte is bounded to the compound.

The term "permanent positively charged" is used in the context of the present disclosure that the positive charge of the pyridinium unit is not readily reversible, for example, via flushing, dilution, filtration, and the like. A permanent positive charge may be the result, for example, of covalent bonding. A permanent positive charge is in contrast to a reversible positive charge (a non-permanent positive charge) that may be the result, for example, of an electrostatic interaction.

The term "limit of detection" or "LOD" is the lowest concentration of an analyte that the bioanalytical procedure can reliably differentiate the analyte from background noise.

Analytes may be present in a sample of interest, e.g. a biological or clinical sample. The term "sample" or "sample of interest" are used interchangeably herein, referring to a pail or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial spinal fluid, urine, saliva, and lymphatic fluid, or solid samples such as dried blood spots and tissue extracts. Further examples of samples are cell cultures or tissue cultures.

In the context of the present disclosure, the sample may be derived from an "individual" or "subject". Typically, the subject is a mammal. Mammals include, but are not limited to, domesticated animals (e.g., cows, sheep, cats, dogs, and horses), primates (e.g., humans and non-human primates such as monkeys), rabbits, and rodents (e.g., mice and rats).

Before being analysed via Mass Spectrometry, a sample may be pre-treated in a sample- and/or analyte specific manner. In the context of the present disclosure, the term "pre-treatment" refers to any measures required to allow for the subsequent analysis of a desired analyte via Mass Spectrometry. Pre-treatment measures typically include but are not limited to the elution of solid samples (e.g. elution of dried blood spots), addition of hemolizing reagent (HR) to whole blood samples, and the addition of enzymatic reagents to urine samples. Also the addition of internal standards (ISTD) is considered as pre-treatment of the sample.

The term "hemolysis reagent" (HR) refers to reagents which lyse cells present in a sample, in the context of this invention hemolysis reagents in particular refer to reagents which lyse the cell present in a blood sample including but not limited to the erythrocytes present in whole blood samples. A well known hemolysis reagent is water ($H_2O$). Further examples of hemolysis reagents include but are not limited to deionized water, liquids with high osmolarity (e.g. 8M urea), ionic liquids, and different detergents.

Typically, an "internal standard" (ISTD) is a known amount of a substance which exhibits similar properties as the analyte of interest when subjected to the mass spectrometric detection workflow (i.e. including any pre-treatment, enrichment and actual detection step). Although the ISTD exhibits similar properties as the analyte of interest, it is still clearly distinguishable from the analyte of interest. Exemplified, during chromatographic separation, such as gas or liquid chromatography, the ISTD has about the same retention time as the analyte of interest from the sample. Thus, both the analyte and the ISTD enter the mass spectrometer at the same time. The ISTD however, exhibits a different molecular mass than the analyte of interest from the sample. This allows a mass spectrometric distinction between ions from the ISTD and ions from the analyte by means of their different mass/charge (m/z) ratios. Both are subject to fragmentation and provide daughter ions. These daughter ions can be distinguished by means of their m/z ratios from each other and from the respective parent ions. Consequently, a separate determination and quantification of the signals from the ISTD and the analyte can be performed. Since the ISTD has been added in known amounts, the signal intensity of the analyte from the sample can be attributed to a specific quantitative amount of the analyte. Thus, the addition of an ISTD allows for a relative comparison of the amount of analyte detected, and enables unambiguous identification and quantification of the analyte(s) of interest present in the sample when the analyte(s) reach the mass spectrometer. Typically, but not necessarily, the ISTD is an isotopically labeled variant (comprising e.g. $^2H$, $^{13}C$, or $^{15}N$ etc. label) of the analyte of interest.

In addition to the pre-treatment, the sample may also be subjected to one or more enrichment steps. In the context of the present disclosure, the term "first enrichment process" or "first enrichment workflow" refers to an enrichment process which occurs subsequent to the pre-treatment of the sample and provides a sample comprising an enriched analyte relative to the initial sample. The first enrichment workflow may comprise chemical precipitation (e.g. using acetonitrile) or the use of a solid phase. Suitable solid phases include but are not limited to Solid Phase Extraction (SPE) cartridges, and beads. Beads may be non-magnetic, magnetic, or paramagnetic. Beads may be coated differently to be specific for the analyte of interest. The coating may differ depending on the use intended, i.e. on the intended capture molecule. It is well-known to the skilled person which coating is suitable for which analyte. The beads may be made of various different materials. The beads may have various sizes and comprise a surface with or without pores.

In the context of the present disclosure the term "second enrichment process" or "second enrichment workflow" refers to an enrichment process which occurs subsequent to the pre-treatment and the first enrichment process of the sample and provides a sample comprising an enriched analyte relative to the initial sample and the sample after the first enrichment process.

The term "chromatography" refers to a process in which a chemical mixture carried by a liquid or gas is separated into components as a result of differential distribution of the chemical entities as they flow around or over a stationary liquid or solid phase.

The term "liquid chromatography" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Methods in which the stationary phase is more polar than the mobile phase (e.g., toluene as the mobile phase, silica as the stationary phase) are termed normal phase liquid chromatography (NPLC) and methods in which the stationary phase is less polar than the mobile phase (e.g., water-methanol mixture as the mobile phase and C18 (octadecylsilyl) as the stationary phase) is termed reversed phase liquid chromatography (RPLC).

"High performance liquid chromatography" or "HPLC" refers to a method of liquid chromatography in which the degree of separation is increased by forcing the mobile phase under pressure through a stationary phase, typically a densely packed column. Typically, the column is packed with a stationary phase composed of irregularly or spherically shaped particles, a porous monolithic layer, or a porous membrane. HPLC is historically divided into two different sub-classes based on the polarity of the mobile and stationary phases. Methods in which the stationary phase is more polar than the mobile phase (e.g., toluene as the mobile phase, silica as the stationary phase) are termed normal phase liquid chromatography (NPLC) and the opposite (e.g., water-methanol mixture as the mobile phase and C18 (octadecylsilyl) as the stationary phase) is termed reversed phase liquid chromatography (RPLC). Micro LC refers to a HPLC method using a column having a narrow inner column diameter, typically below 1 mm, e.g. about 0.5 mm. "Ultra high performance liquid chromatography" or "UHPLC" refers to a HPLC method using a pressure of 120 MPa (17,405 lbf/in2), or about 1200 atmospheres. Rapid LC refers to an LC method using a column having an inner diameter as mentioned above, with a short length <2 cm, e.g. 1 cm, applying a flow rate as mentioned above and with a pressure as mentioned above (Micro LC, UHPLC). The short Rapid LC protocol includes a trapping/wash/elution step using a single analytical column and realizes LC in a very short time <1 min.

Further well-known LC modi include "hydrophilic interaction chromatography" (HILIC), size-exclusion LC, ion exchange LC, and affinity LC.

LC separation may be single-channel LC or multi-channel LC comprising a plurality of LC channels arranged in parallel. In LC analytes may be separated according to their polarity or log P value, size or affinity, as generally known to the skilled person.

The term "fragmentation" refers to the dissociation of a single molecule into two or more separate molecules. As used herein, the term fragmentation refers to a specific fragmentation event, wherein the breaking point in the parent molecule at which the fragmentation event takes place is well defined, and wherein the two or more daughter molecules resulting from the fragmentation event are well characterised. It is well-known to the skilled person how to determine the breaking point of a parent molecule as well as the two or more resulting daughter molecules. The resulting daughter molecules may be stable or may dissociate in subsequent fragmentation events. Exemplified, in case a parent molecule undergoing fragmentation comprises a N-benzylpyridinium unit, the skilled person is able to determine based on the overall structure of the molecule whether the pyridinium unit will fragment to release a benzyl entity or would be released completely from the parent molecule, i.e the resulting daughter molecules would either be a benzyl molecule and a parent molecule lacking of benzyl. Fragmentation may occur via collision-induced dissociation (CID), electron-capture dissociation (ECD), electron-transfer dissociation (ETD), negative electron-transfer dissociation (NETD), electron-detachment dissociation (EDD), photodissociation, particularly infrared multiphoton dissociation (IRMPD) and blackbody infrared radiative dissociation (BIRD), surface-induced dissociation (SID), Higher-energy C-trap dissociation (HCD), charge remote fragmentation.

The term "reactive unit" refers to a unit able to react with another molecule, i.e. which is able to form covalent bond with another molecule, such as an analyte of interest. Typically, such covalent bond is formed with a chemical group present in the other molecule. Accordingly, upon chemical reaction, the reactive unit of the compound forms a covalent bond with a suitable chemical group present in the analyte molecule. As this chemical group present in the analyte molecule, fulfils the function of reacting with the reactive unit of the compound, the chemical group present in the analyte molecule is also referred to as the "functional group" of the analyte. The formation of the covalent bond occurs in each case in a chemical reaction, wherein the new covalent bond is formed between atoms of the reactive group and the functional groups of the analyte. It is well known to the person skilled in the art that in forming the covalent bond between the reactive group and the functional groups of the analyte, atoms are lost during this chemical reaction.

In the context of the present disclosure, the term "complex" refers to the product produced by the reaction of a compound with an analyte molecule. This reaction leads to the formation of a covalent bond between the compound and the analyte. Accordingly, the term complex refers to the covalently bound reaction product formed by the reaction of the compound with the analyte molecule.

A "kit" is any manufacture (e.g., a package or container) comprising at least one reagent, e.g., a medicament for treatment of a disorder, or a probe for specifically detecting a biomarker gene or protein of the invention. The kit is preferably promoted, distributed, or sold as a unit for performing the methods of the present invention. Typically, a kit may further comprise carrier means being compartmentalised to receive in close confinement one or more container means such as vials, tubes, and the like. In particular, each of the container means comprises one of the separate elements to be used in the method of the first aspect. Kits may further comprise one or more other reagents including but not limited to reaction catalyst. Kits may further comprise one or more other containers comprising further materials including but not limited to buffers, diluents, filters, needles, syringes, and package inserts with instructions for use. A label may be present on the container to indicate that the composition is used for a specific application, and may also indicate directions for either in vivo or in vitro use. The computer program code may be provided on a data storage medium or device such as a optical storage medium (e.g., a Compact Disc) or directly on a computer or data processing device. Moreover, the kit may, comprise standard amounts for the biomarkers as described elsewhere herein for calibration purposes.

EMBODIMENTS

In a first aspect, the present invention relates to compounds or at least one compound of formula I:

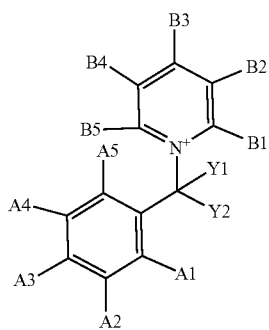

(I)

wherein one of the substituents B1, B2, B3, B4, B5 is a coupling group Q, which is capable of forming a covalent bond with the analyte, wherein the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof, wherein Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic. In particular, the compound or the compounds of formula I are for mass spectrometric determination of an analyte.

Compounds according to the present invention comprise moieties which show a mass fragmentation event at low collision energies (e.g. in the range of 10 eV to 50 eV, borders included). These compounds feature an overall compact structure. This can allow for a simple modular design of labeling reagents to solve various problems by modifying the charge-containing moiety pyridinium, quaternary ammonium, imidazolium, triphenylphosphonium, stable metal complexes, sulfonic acid, borates, aryl trifluoroborates, sulfates, phosphates, . . . ) whereas a permanent charge is preferred. This can allow to fine tune the hydrophobicity of the reagents to improve the separation of sample matrix in the purification process. Furthermore, the mass fragmentation can occur at low energy levels to favor the primary fragmentation pathway. This can result in an increased sensitivity in the MS/MS mode. Regardless of the above an extra MS experiment can be conducted at higher energies to gain additional fragmentation pathways.

In embodiments of the first aspect of the present invention, halogen is selected from the group consisting of F, Cl, Br and I.

In embodiments of the first aspect of the present invention, alkyl is selected from the group consisting of methyl, ethyl, propyl, iso-propyl, n-butyl, iso-butyl, sec-butyl, tenbutyl, pentyl, hexyl and cyclohexyl. Alkyl can comprise modified alkyl. Modified alkyl comprises the structural unit alkyl-O-alkyl, e.g. —CH$_2$O—CH$_3$, —CH$_2$—O—CH$_2$—CH$_3$.

In embodiments of the first aspect of the present invention, N-acylamino is selected from the group consisting of formylamino, acetylamino, propionylamino and benzoylamino.

In embodiments of the first aspect of the present invention, N, N-dialkylamino is selected from the group consisting of N,N-dimethylamino, N,N-ethylmethylamino, N,N-diethylamino, N,N-methylpropylamino, N,N-ethylpropylamino, N,N-dipropylamino, N,N-butylmethylamino, N,N-butylmethylamino, N,N-butylpropylamino, N,N-dibutylamino, N-azetidinyl, N-pyrrolidinyl, N-piperidinyl and N-piperazinyl.

In embodiments of the first aspect of the present invention, alkoxy is selected from the group consisting of methoxy, ethoxy, propoxy, butoxy, phenoxy and benzyloxy.

In embodiments of the first aspect of the present invention, thioalkoxy is selected from the group consisting of thiomethyl, thioethyl, thiopropyl, thiobutyl, thiopentyl and thiohexyl.

In embodiments of the first aspect of the present invention, alkoxycarbonyl is selected from the group consisting of methoxycarbonyl, ethoxycarbonyl, propoxycarbonyl, butoxycarbonyl, phenoxycarbonyl and benzyloxycarbonyl.

In embodiments of the first aspect of the present invention, alkoxythiocarbonyl is selected from the group consisting of methoxythiocarbonyl, ethoxythiocarbonyl, propoxythiocarbonyl, butoxythiocarbonyl, phenoxythiocarbonyl and benzyloxythiocarbonyl.

In embodiments of the first aspect of the present invention, acyl is selected from the group consisting of formyl, acetyl and propionyl.

In embodiments of the first aspect of the present invention, thioacyl is selected from the group consisting of thioformyl, thioacetyl, thiopropionyl and thiobenzoyl.

In embodiments of the first aspect of the present invention, aryloyl is selected from the group consisting of benzoyl, naphthoyl and anthracenoyl.

In embodiments of the first aspect of the present invention, acyloxy is selected from the group consisting of formyloxy, acetyloxy and propionyloxy.

In embodiments of the first aspect of the present invention, aryloyloxy is selected from the group consisting of benzoyloxy, naphthoyloxy and anthracenoyloxy.

In embodiments of the first aspect of the present invention, cycloalkyl is selected from the group consisting of cyclopropyl, cyclobutyl, cyclopentyl and cyclohexyl.

In embodiments of the first aspect of the present invention, aryl is selected from the group consisting of phenyl, benzyl, naphthyl, anthracenyl and phenathrenyl.

In embodiments of the first aspect of the present invention, heteroaryl is selected from the group consisting of imidazole, pyrazole, triazole, tetrazole, oxazole, isoxazole, thiophene, furan, thiazole, pyridine, pyrimidine, benzotriazole, benzofuran and benzoimidazole.

In embodiments of the first aspect of the present invention, heterocycloalkyl is selected from the group consisting of N-azetidinyl, N-pyrrolidinyl, N-piperidinyl and N-piperazinyl.

In embodiments of the first aspect of the present invention, substituted aromatic is selected from the group consisting of methoxyphenyl, cyanophenyl and ethylnaphthyl.

In embodiments of the first aspect of the present invention, the ring structure comprising Y1 and Y2 is selected from the group consisting of phenyl, benzyl, methyl, ethyl, propyl and acetyloxy.

In embodiments of the first aspect of the present invention, the other substituents A1, A2, A3, A4, A5, B1, B2, B3, B4, B5 are each independently selected from hydrogen, halogen, alkyl, N-acylamino, alkoxy, thioalkoxy, hydroxy, cyano, alkoxycarbonyl, alkoxythiocarbonyl, acyl, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, isotope or derivative thereof.

In embodiments of the first aspect of the present invention, Y1 and Y2 are each independently selected from hydrogen, methyl, ethyl, methoxy, amine or wherein Y1 and Y2 form a ring structure, which is selected from substituted cycloalkyl, unsubstituted cycloalkyl, substituted aromatic, benzylic, unsubstituted aromatic, substituted heteroaromatic, unsubstituted heteroaromatic.

In embodiments of the first aspect of the present invention, the compound of formula I comprises a coupling group Q. At least one of the substituents B1, B2, B3, B4 or B5 of formula I is the coupling group Q. Preferably, B1 or B2 or B3 is Q.

In embodiments of the first aspect of the present invention, the coupling group Q is bonded to X according to the following formula II:

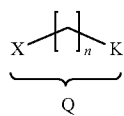

(II)

wherein K is a reactive unit, which is capable of forming the covalent bond with the analyte,
wherein n is 0, 1, 2, 3, 4 or 5, and wherein X is a carbon-atom of the pyridinium cation of formula I, in particular a binding carbon-atom of the pyridinium cation of formula I.

In embodiments of the first aspect of the present invention, Q does not show any fragmentation at energy levels that are lower than those who trigger the mass fragmentation.

In embodiments of the first aspect of the present invention, Q is bonded to X via a covalently bonding.

In embodiments of the first aspect of the present invention, Q is selected from the group consisting of methyl hydrazide, methyl hydrazine, hydrazine, methyl hydroxylamine, acetohydrazide, 4-substituted 1,2,4-triazoline-3,5-dione (TAD) and F.

In embodiments of the first aspect of the present invention, K is directly bonded to X (n=0).

In embodiments of the first aspect of the present invention, K is bonded to X via a methylene group (n=1).

In embodiments of the first aspect of the present invention, K is bonded to X via a ethylene group (n=2).

In embodiments of the first aspect of the present invention, K is bonded to X via a propylene group (n=3).

In embodiments of the first aspect of the present invention, K is bonded to X via a butylene group (n=4).

In embodiments of the first aspect of the present invention, K is bonded to X via a pentylene group (n=5).

In embodiments of the first aspect of the present invention, the carbon-atom X of the pyridinium cation of formula I is the binding partner of B1, B2, B3, B4 or B5.

In embodiments of the first aspect of the present invention, said compound is selected from the following group I-1, I-2, I-3, I-4 and I-5:

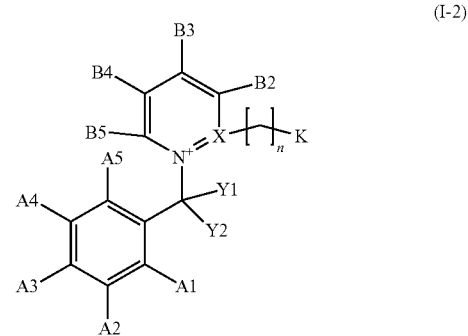

(I-2)

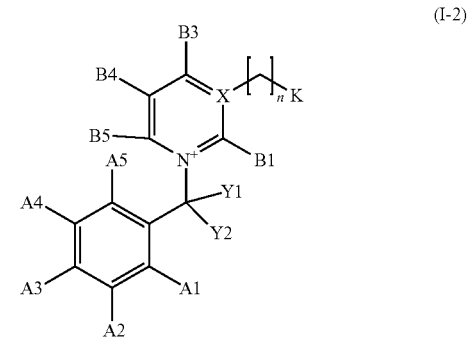

(I-2)

-continued

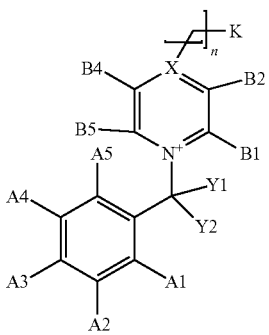

(I-3)

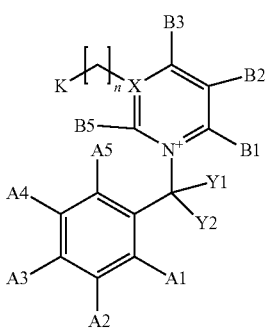

(I-4)

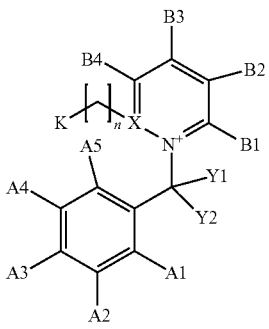

(I-5)

wherein each of A1, A2, A3, A4, A5, B1, B2, B3, B4, B5, K, X and n has the meaning as mentioned above. Preferably, the compound comprises formula I-1, I-2 or I-3.

In embodiments of the first aspect of the present invention, the compound of formula I according to the present invention comprises a reactive unit K which is capable of reacting with an analyte or an analyte molecule. The reactive unit K is capable of reacting with an analyte molecule such that a covalent bond between the compound of formula I and the analyte molecule is formed. Preferably, the covalent bond is a single or double bond.

In embodiments of the first aspect of the present invention, the reactive unit K forms a covalent bond with the compound of formula I. In particular, the covalent bond is formed between the reactive unit K of compound of formula I and a functional group present in the analyte molecule.

In embodiments of the first aspect of the present invention, K is capable of reacting with a carbonyl group, phenol group, amine, hydroxyl group or diene group of the analyte.

In embodiments of the first aspect of the present invention, K is selected from the group consisting of hydrazide, hydrazine, hydroxylamine, Br, F, 4-substituted 1,2,4-triazoline-3,5-dione (TAD), 4-Phenyl-1,2,4-triazoline-3,5-dione (PTAD), 4-pyridinium-1,2,4-triazoline-3,5-dione and reactive carbonyl group.

In embodiments of the first aspect of the present invention, n=0 and K is Br or n=0 and K is F.

Depending on the functional groups present in the analyte molecule to be determined, the skilled person will select an appropriate reactive unit K for compound of formula I. It is within common knowledge to decide which reactive unit K will qualify for binding to a functional group of an analyte of interest.

In embodiments of the first aspect of the present invention, the analyte molecule comprises a functional group selected from the group consisting of carbonyl group, diene group, hydroxyl group, amine group, imine group, ketone group, aldehyde group, thiol group, diol group, phenolic group, expoxid group, disulfide group, nucleobase group, carboxylic acid group, terminal cysteine group, terminal serine group and azide group, each of which is capable of forming a covalent bond with reactive unit K of compound of formula I. Further, it is also contemplated within the scope of the present invention that a functional group present on an analyte molecule would be first converted into another group that is more readily available for reaction with reactive unit K of compounds of formula I.

In embodiments of the first aspect of the present invention, the analyte molecule is selected from the group consisting of steroids, ketosteroids, secosteroids, amino acids, peptides, proteins, carbohydrates, fatty acids, lipids, nucleosides, nucleotides, nucleic acids and other biomolecules including small molecule metabolites and cofactors as well as therapeutic drugs, drugs of abuse, toxins or metabolites thereof.

In embodiments of the first aspect of the present invention, the analyte molecule comprises a carbonyl group as functional group which is selected from the group consisting of a carboxylic acid group, aldehyde group, keto group, a masked aldehyde, masked keto group, ester group, amide group, and anhydride group. Aldoses (aldehyde and keto) exist as acetal and hemiacetals, a sort of masked form of the parent aldehyde/keto.

In embodiments of the first aspect of the present invention, the carbonyl group is an amide group, the skilled person is well aware that the amide group as such is a stable group, but that it can be hydrolyzed to convert the amide group into a carboxylic acid group and an amino group. Hydrolysis of the amide group may be achieved via acid/base catalysed reaction or by enzymatic process either of which is well-known to the skilled person. In embodiments of the first aspect of the present invention, wherein the carbonyl group is a masked aldehyde group or a masked keto group, the respective group is either a hemiacetal group or acetal group, in particular a cyclic hemiacetal group or acetal group. In embodiments of the first aspect of the present invention, the acetal group, is converted into an aldehyde or keto group before reaction with the compound of formula I.

In embodiments of the first aspect of the present invention, the carbonyl group is a keto group. In embodiments of the first aspect of the present invention, the keto group may be transferred into an intermediate imine group before reacting with the reactive unit of compounds of formula I. In embodiments of the first aspect of the present invention, the analyte molecule comprising one or more keto groups is a ketosteroid. In particular embodiments of the first aspect of the present invention, the ketosteroid is selected from the group consisting of testosterone, epitestosterone, dihydrotestosterone (DHT), desoxymethyltestosterone (DMT), tetrahydrogestrinone (THG), aldosterone, estrone, 4-hydroxyestrone, 2-methoxyestrone, 2-hydroxyestrone, 6-ketoestradiol, 16-alpha-hydroxyestrone, 2-hydroxyestrone-3- methylether, prednisone, prednisolone, pregnenolone, progesterone, dehydroepiandrosterone (DHEA), 17-hydroxypregnenolone, 17-hydroxyprogesterone, androsterone, epiandrosterone, Δ4-androstenedione, 11-deoxycortisol, corticosterone, 21-deoxycortisol, 11-deoxycorticosterone, allopregnanolone and aldosterone.

In embodiments of the first aspect of the present invention, the carbonyl group is a carboxyl group. In embodiments of the first aspect of the present invention, the carboxyl group reacts directly with the compound of formula I or it is converted into an activated ester group before reaction with the compound of formula I. In embodiments of the first aspect of the present invention, the analyte molecule comprising one or more carboxyl groups is selected from the group consisting of Δ8-tetrahydrocannabinolic acid, benzoylecgonin, salicylic acid, 2-hydroxybenzoic acid, gabapentin, pregabalin, valproic acid, vancomycin, methotrexate, mycophenolic acid, montelukast, repaglinide, furosemide, telmisartan, gemfibrozil, diclofenac, ibuprofen, indomethacin, zomepirac, isoxepac and penicillin. In embodiments of the first aspect of the present invention, the analyte molecule comprising one or more carboxyl groups is an amino acid selected from the group consisting of arginine, lysine, aspartic acid, glutamic acid, glutamine, asparagine, histidine, serine, threonine, tyrosine, cysteine, tryptophan, alanine, isoleucine, leucine, methionine, phenylalanine, valine, proline and glycine.

In embodiments of the first aspect of the present invention, the carbonyl group is an aldehyde group. In embodiments of the first aspect of the present invention, the aldehyde group may be transferred into an intermediate imine group before reacting with the reactive unit of compounds of formula I. In embodiments of the first aspect of the present invention, the analyte molecule comprising one or more aldehyde groups is selected from the group consisting of pyridoxal, N-acetyl-D-glucosamine, alcaftadine, streptomycin and josamycin.

In embodiments of the first aspect of the present invention, the carbonyl group is an carbonyl ester group. In embodiments of the first aspect of the present invention, the analyte molecule comprising one or more ester groups is selected from the group consisting of cocaine, heroin, Ritalin, aceclofenac, acetylcholine, amcinonide, amiloxate, amylocaine, anileridine, aranidipine artesunate and pethidine.

In embodiments of the first aspect of the present invention, the carbonyl group is an anhydride group. In embodiments of the first aspect of the present invention, the analyte molecule comprising one or more anhydride groups is selected from the group consisting of cantharidin, succinic anhydride, trimellitic anhydride and maleic anhydride.

In embodiments of the first aspect of the present invention, the analyte molecule comprises one or more diene groups, in particular to conjugated diene groups, as functional group. In embodiments of the first aspect of the present invention, the analyte molecule comprising one or more diene groups is a secosteroid. In embodiments, the secosteroid is selected from the group consisting of cholecalciferol (vitamin D3), ergocalciferol (vitamin D2), calcifediol, calcitriol, tachysterol, lumisterol and tacalcitol. In particular, the secosteroid is vitamin D, in particular vitamin D2 or D3 or derivates thereof. In particular embodiments, the secosteroid is selected from the group consisting of vitamin D2, vitamin D3, 25-hydroxyvitamin D2, 25-hydroxyvitamin D3 (calcifediol), 3-epi-25-hydroxyvitamin D2, 3-epi-25-hydroxyvitamin D3, 1,25-dihydroxyvitamin D2, 1,25-dihydroxyvitamin D3 (calcitriol), 24,25-dihydroxyvitamin D2, 24,25-dihydroxyvitamin D3. In embodiments of the first aspect of the present invention, the analyte molecule comprising one or more diene groups is selected from the group consisting of vitamin A, tretinoin, isotretinoin, alitretinoin, natamycin, sirolimus, amphotericin B, nystatin, everolimus, temsirolimus and fidaxomicin.

In embodiments of the first aspect of the present invention, the analyte molecule comprises one or more hydroxyl group as functional group. In embodiments of the first aspect of the present invention, the analyte molecule comprises a single hydroxyl group or two hydroxyl groups. In embodiments wherein more than one hydroxyl group is present, the two hydroxyl groups may be positioned adjacent to each other (1,2-diol) or may be separated by 1, 2 or 3 C atoms (1,3-diol, 1,4-diol, 1,5-diol, respectively). In particular embodiments of the first aspect, the analyte molecule comprises a 1,2-diol group. In embodiments, wherein only one hydroxyl group is present, said analyte is selected from the group consisting of primary alcohol, secondary alcohol and tertiary alcohol. In embodiments of the first aspect of the present invention, wherein the analyte molecule comprises one or more hydroxyl groups, the analyte is selected from the group consisting of benzyl alcohol, menthol, L-carnitine, pyridoxine, metronidazole, isosorbide mononitrate, guaifenesin, clavulanic acid, Miglitol, zalcitabine, isoprenaline, aciclovir, methocarbamol, tramadol, venlafaxine, atropine, clofedanol, alpha-hydroxyalprazolam, alpha-Hydroxytriazolam, lorazepam, oxazepam, Temazepam, ethyl glucuronide, ethylmorphine, morphine, morphine-3-glucuronide, buprenorphine, codeine, dihydrocodeine, p-hydroxypropoxyphene, O-desmethyltramadol, Desmetramadol, dihydroquinidine and quinidine. In embodiments of the first aspect of the present invention, wherein the analyte molecule comprises more than one hydroxyl groups, the analyte is selected from the group consisting of vitamin C, glucosamine, mannitol, tetrahydrobiopterin, cytarabine, azacitidine, ribavirin, floxuridine, Gemcitabine, Streptozotocin, adenosine, Vidarabine, cladribine, estriol, trifluridine, clofarabine, nadolol, zanamivir, lactulose, adenosine monophosphate, idoxuridine, regadenoson, lincomycin, clindamycin, Canagliflozin, tobramycin, netilmicin, kanamycin, ticagrelor, epirubicin, doxorubicin, arbekacin, streptomycin, ouabain, amikacin, neomycin, framycetin, paromomycin, erythromycin, clarithromycin, azithromycin, vindesine, digitoxin, digoxin, metrizamide, acetyldigitoxin, deslanoside, Fludarabine, clofarabine, gemcitabine, cytarabine, capecitabine, vidarabine, and plicamycin.

In embodiments of the first aspect of the present invention, the analyte molecule comprises one or more thiol group (including but not limited to alkyl thiol and aryl thiol groups) as functional group. In embodiments of the first aspect of the present invention, the analyte molecule comprising one or more thiol groups is selected from the group consisting of thiomandelic acid, DL-captopril, DL-thiorphan, N-acetylcysteine, D-penicillamine, glutathione, L-cysteine, zofenoprilat, tiopronin, dimercaprol, succimer.

In embodiments of the first aspect of the present invention, the analyte molecule comprises one or more disulfide group as functional group. In embodiments of the first aspect of the present invention, the analyte molecule comprising one or more disulfide groups is selected from the group consisting of glutathione disulfide, dipyrithione, selenium sulfide, disulfiram, lipoic acid, L-cystine, fursultiamine, octreotide, desmopressin, vapreotide, terlipressin, linaclotide and peginesatide. Selenium sulfide can be selenium disulfide, $SeS_2$, or selenium hexasulfide, $Se_2S_6$.

In embodiments of the first aspect of the present invention, the analyte molecule comprises one or more epoxide group as functional group. In embodiments of the first aspect of the present invention, the analyte molecule comprising one or more epoxide groups is selected from the group consisting of Carbamazepine-10,11-epoxide, carfilzomib, furosemide epoxide, fosfomycin, sevelamer hydrochloride, cerulenin, scopolamine, tiotropium, tiotropium bromide, methyl scopolamine bromide, eplerenone, mupirocin, natamycin, and troleandomycin.

In embodiments of the first aspect of the present invention, the analyte molecule comprises one or more phenol groups as functional group. In particular embodiments of the first aspect of the present invention, analyte molecules comprising one or more phenol groups are steroids or steroid-like compounds. In embodiments of the first aspect of the present invention, the analyte molecule comprising one or more phenol groups is a steroid or a steroid-like compound having an A-ring which is $sp^2$ hybridized and an OH group at the 3-position of the A-ring. In particular embodiments of the first aspect of the present invention, the steroid or steroid-like analyte molecule is selected from the group consisting of estrogen, estrogen-like compounds, estrone (E1), estradiol (E2), 17a-estradiol, 17b-estradiol, estriol (E3), 16-epiestriol, 17-epiestriol, and 16, 17-epiestriol and/or metabolites thereof. In embodiments, the metabolites are selected from the group consisting of estriol, 16-epiestriol (16-epiE3), 17-epiestriol (17-epiE3), 16,17-epiestriol (16,17-epiE3), 16-ketoestradiol (16-ketoE2), 16a-hydroxyestrone (16a-OHE1), 2-methoxyestrone (2-MeOE1), 4-methoxyestrone (4-MeOE1), 2-hydroxyestrone-3-methyl ether (3-MeOE1), 2-methoxyestradiol (2-MeOE2), 4-methoxyestradiol (4-MeOE2), 2-hydroxyestrone (2-OHE1), 4-hydroxyestrone (4-OHE1), 2-hydroxyestradiol (2-OHE2), estrone (E1), estrone sulfate (E1s), 17a-estradiol (E2a), 17b-estradiol (E2B), estradiol sulfate (E2S), equilin (EQ), 17a-dihydroequilin (EQa), 17b-dihydroequilin (EQb), Equilenin (EN), 17-dihydroequilenin (ENa), 17α-dihydroequilenin, 17β-dihydroequilenin (ENb), Δ8,9-dehydroestrone (dE1), Δ8,9-dehydroestrone sulfate (dE1s), Δ9-tetrahydrocannabinol, mycophenolic acid. β or b can be used interchangeable. α and a can be used interchangeable.

In embodiments of the first aspect of the present invention, the analyte molecule comprises an amine group as functional group. In embodiments of the first aspect of the present invention, the amine group is an alkyl amine or an aryl amine group. In embodiments of the first aspect of the present invention, the analyte comprising one or more amine groups is selected from the group consisting of proteins and peptides. In embodiments of the first aspect of the present invention, the analyte molecule comprising an amine group is selected from the group consisting of 3,4-methylenedioxyamphetamine, 3,4-methylenedioxy-N-ethylamphetamine, 3,4-methylenedioxymethamphetamine, Amphetamine, Methamphetamine, N-methyl-1,3-benzodioxolylbutanamine, 7-aminoclonazepam, 7-aminoflunitrazepam, 3,4-dimethylmethcathinone, 3-fluoromethcathinone, 4-methoxymethcathinone, 4-methylethcathinone, 4-methylmethcathinone, amfepramone, butylone, ethcathinone, elephedrone, methcathinone, methylone, methylenedioxypyrovalerone, benzoylecgonine, dehydronorketamine, ketamine, norketamine, methadone, normethadone, 6-acetylmorphine, diacetylmorphine, morphine, norhydrocodone, oxycodone, oxymorphone, phencyclidine, norpropoxyphene, amitriptyline, clomipramine, dothiepin, doxepin, imipramine, nortriptyline, trimipramine, fentanyl, glycylxylidide, lidocaine, monoethylglycylxylidide, N-acetylprocainamide, procainamide, pregabalin, 2-Methylamino-1-(3,4-methylendioxyphenyl)butan, N-methyl-1,3-benzodioxolylbutanamine, 2-Amino-1-(3,4-methylendioxyphenyl)butan, 1,3-benzodioxolylbutanamine, normeperidine, O-Destramadol, desmetramadol, tramadol, lamotrigine, Theophylline, amikacin, gentamicin, tobramycin, vancomycin, Methotrexate, Gabapentin sisomicin and 5-methylcytosine.

In embodiments of the first aspect of the present invention, the analyte molecule is a carbohydrate or substance having a carbohydrate moiety, e.g. a glycoprotein or a nucleoside. In embodiments of the first aspect of the present invention, the analyte molecule is a monosaccharide, in particular selected from the group consisting of ribose, desoxyribose, arabinose, ribulose, glucose, mannose, galactose, fucose, fructose, N-acetylglucosamine, N-acetylgalactosamine, neuraminic acid, N-acetylneurominic acid, etc. In embodiments, the analyte molecule is an oligosaccharide, in particular selected from the group consisting of a disaccharide, trisaccharid, tetrasaccharide, polysaccharide. In embodiments of the first aspect of the present invention, the disaccharide is selected from the group consisting of sucrose, maltose and lactose. In embodiments of the first aspect of the present invention, the analyte molecule is a substance comprising above described mono-, di-, tri-, tetra-, oligo- or polysaccharide moiety.

In embodiments of the first aspect of the present invention, the analyte molecule comprises an azide group as functional group which is selected from the group consisting of alkyl or aryl azide. In embodiments of the first aspect of the present invention, the analyte molecule comprising one or more azide groups is selected from the group consisting of zidovudine and azidocillin.

Such analyte molecules may be present in biological or clinical samples such as body liquids, e.g. blood, serum, plasma, urine, saliva, spinal fluid, etc., tissue or cell extracts, etc. In embodiments of the first aspect of the present invention, the analyte molecule(s) are present in a biological or clinical sample selected from the group consisting of blood, serum, plasma, urine, saliva, spinal fluid, and a dried blood spot. In some embodiments of the first aspect of the present invention, the analyte molecules may be present in a sample which is a purified or partially purified sample, e.g. a purified or partially purified protein mixture or extract.

In embodiments of the first aspect of the present invention, the reactive unit K is selected from the group consisting of a carbonyl reactive unit, a diene reactive unit, a hydroxyl reactive unit, an amino reactive unit, an imine reactive unit, a thiol reactive unit, a diol reactive unit, a phenol reactive unit, an epoxide reactive unit, a disulfide reactive unit, and an azido reactive unit.

In embodiments of the first aspect of the present invention, the reactive unit K is a carbonyl reactive unit, which is capable of reacting with any type of molecule having a carbonyl group. In embodiments of the first aspect of the present invention, the carbonyl reactive unit is selected from the group consisting of carboxyl reactive unit, keto reactive unit, aldehyde reactive unit, anhydride reactive unit, carbonyl ester reactive unit, and imide reactive unit. In embodiments of the first aspect of the present invention, the carbonyl-reactive unit may have either a super-nucleophilic N atom strengthened by the α-effect through an adjacent O or N atom NH2-N/O or a dithiol molecule.

In embodiments of the first aspect of the present invention, the carbonyl-reactive unit is selected from the group:

(i) a hydrazine unit, e.g. a $H_2N$—NH—, or $H_2N$—$NR^1$— unit, wherein $R^1$ is aryl, aryl containing one or more heteroatoms or $C_{1-4}$ alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N$—NH—C(O)—, or $H_2N$—$NR^2$—C(O)— unit, wherein $R^2$ is aryl, aryl containing one or more heteroatoms or $C_{1-4}$ alkyl, particularly $C_1$ or $C_2$ alkyl, optionally substituted e.g. with halo, hydroxyl, and/or $C_{1-3}$ alkoxy, (iii) a hydroxylamino unit, e.g. a $H_2N$—O— unit, and (iv) a dithiol unit, particularly a 1,2-dithiol or 1,3-dithiol unit.

In embodiments of the first aspect of the present invention, the carbonyl reactive unit is a carboxyl reactive unit, the carboxyl reactive units reacts with carboxyl groups on an analyte molecule. In embodiment of the first aspect of the present invention, the carboxyl reactive unit is selected from the group consisting of a diazo unit, an alkylhalide, amine, and hydrazine unit.

In embodiments of the first aspect of the present invention, analyte molecule comprises an ketone or aldehyde group and K is a carbonyl reactive unit, which is selected from the group:

(i) a hydrazine unit,
(ii) a hydrazide unit,
(iii) a hydroxylamino unit, and
(iv) a dithiol unit.

In embodiments of the first aspect of the present invention, the reactive unit K is a diene reactive unit, which is capable of reacting with an analyte comprising a diene group. In embodiments of the first aspect of the present invention, the diene reactive unit is selected from the group consisting of Cookson-type reagents, e.g. 1,2,4-triazoline-3,5-diones, which are capable to act as a dienophile.

In embodiments of the first aspect of the present invention, the reactive unit K is a hydroxyl reactive unit, which is capable of reacting with an analyte comprising a hydroxyl group. In embodiments of the first aspect of the present invention, the hydroxyl reactive units is selected from the group consisting of sulfonylchlorides, activated carboxylic esters (NHS, or imidazolide), and fluoro aromates/heteroaromates capable for nucleophilic substitution of the fluorine (T. Higashi J Steroid Biochem Mol Biol. 2016 September; 162:57-69). In embodiments of the first aspect of the present invention, the reactive unit K is a diol reactive unit which reacts with an diol group on an analyte molecule. In embodiments of the first aspect of the present invention, wherein the reactive unit is a 1,2 diol reactive unit, the 1,2 diol reactive unit comprises boronic acid. In further embodiments, diols can be oxidised to the respective ketones or aldehydes and then reacted with ketone/aldehyde-reactive units K.

In embodiments of the first aspect of the present invention, the amino reactive unit reacts with amino groups on an analyte molecule. In embodiments of the first aspect of the present invention, the amino-reactive unit is selected from the group consisting of active ester group such as N-hydroxy succinimide (NHS) ester or sulfo-NHS ester, pentafluoro phenyl ester, cabonylimidazole ester, quadratic acid esters, a hydroxybenzotriazole (HOBO ester, 1-hydroxy-7-azabenzotriazole (HOAt) ester, and a sulfonylchloride unit.

In embodiments of the first aspect of the present invention, the thiol reactive unit reacts with an thiol group on an analyte molecule. In embodiments of the first aspect of the present invention, the thiole reactive unit is selected from the group consisting of haloacetyl group, in particular selected from the group consisting of Br/I—CH2-C(=O)— unit, acrylamide/ester unit, unsaturated imide unit such as maleimide, methylsulfonyl phenyloxadiazole and sulfonylchloride unit.

In embodiments of the first aspect of the present invention, the phenol reactive unit reacts with phenol groups on an analyte molecule. In embodiments of the first aspect of the present invention, the phenol-reactive unit is selected from the group consisting of active ester unit such as N-hydroxy succinimide (NHS) ester or sulfo-NHS ester, pentafluoro phenyl ester, carbonyl imidazole ester, quadratic acid esters, a hydroxybenzotriazole (HOBt) ester, 1-hydroxy-7-azabenzotriazole (HOAt) ester, and a sulfonylchloride unit. Phenol groups present on an analyte molecule can be reacted with highly reactive electrophiles like triazolinedione (like TAD) via a reaction (H. Ban et al J. Am. Chem. Soc., 2010, 132 (5), pp 1523-1525) or by diazotization or alternatively by ortho nitration followed by reduction to an amine which could then be reacted with an amine reactive reagent. In embodiments of the first aspect of the present invention, the phenol-reactive unit is fluoro-1-pyridinium.

In embodiments of the first aspect of the present invention, the reactive unit K is an epoxide reactive unit, which is capable of reacting with an analyte comprising an epoxide group. In embodiments of the first aspect of the present invention, the epoxide reactive unit is selected from the group consisting of amino, thiol, super-nucleophilic N atom strengthened by the α-effect through an adjacent O or N atom NH2-N/O molecule. In embodiments of the first aspect of the present invention, the epoxide reactive unit is selected from the group:

(i) a hydrazine unit, e.g. a $H_2N$—NH—, or $H_2N$—NR' unit, wherein $R^1$ is aryl, aryl containing one or more heteroatoms or $C_{1-4}$ alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N$—NH—C(O)—, or $H_2N$—NR'—C(O)— unit, wherein $R^2$ is aryl, aryl containing one or more heteroatoms or $C_{1-4}$ alkyl, particularly $C_1$ or $C_2$ alkyl, optionally substituted e.g. with halo, hydroxyl, and/or $C_{1-3}$ alkoxy, and (iii) a hydroxylamino unit, e.g. a $H_2N$—O— unit.

In embodiments of the first aspect of the present invention, the reactive unit K is a disulfide reactive unit, which is capable of reacting with an analyte comprising a disulfide group. In embodiments of the first aspect of the present invention, the disulfide reactive unit is selected from the group consisting of thiol. In further embodiments, disulfide group can be reduced to the respective thiol group and then reacted with thiol reactive units K.

In embodiments of the first aspect of the present invention, the reactive unit K is a azido reactive unit which reacts with azido groups on an analyte molecule. In embodiments of the first aspect of the present invention, the azido-reactive unit reacts with azido groups through azide-alkyne cycloaddition. In embodiments of the first aspect of the present invention, the azido-reactive unit is selected from the group consisting of alkyne (alkyl or aryl), linear alkyne or cyclic alkyne. The reaction between the azido and the alkyne can proceed with or without the use of a catalyst.

In further embodiments of the first aspect of the present invention the azido group can be reduced to the respective amino group and then reacted with amino reactive units K.

In embodiments of the first aspect of the present invention, the functional group of the analyte is selected from the options mentioned in the left column of the table 1. The reactive group of K of the corresponding functional group of the analyte is selected from the the group mentioned in the right column of table 1.

TABLE 1

Functional group of the analyte and reactive groups for the specific labels

| Functional group of the analyte | Reactive group |
|---|---|
| Amine | Active ester with NHS leaving group, pentafluorophenyl ester, squaric acid esters, sulfonyl chloride, ketone or aldehyde (reductive amination) |
| Thiol | Maleimide, iodoacetyl, methylsulfonyl phenyloxadiazole |
| Diol | Boronic acid (or oxidation to ketone or aldehyde) |
| Ketone, aldehyde | ( )-substituted hydroxylamine, hydrazines, hydrazides. |
| Diene | Dienophiles, triazolinedione (TAD) |
| Phenoles | Ene reaction triazolinedione (TAD), ortho nitration/reduction, diazo formulation/nucleophilic substitution. Active ester with NHS leaving group, pentafluorophenyl ester, squaric acid esters, sulfonyl chloride, fluoro-1-pyridinium. |
| Nucleobase | Chloro acetyl/Pt complexes |
| Unspecific | Azide (Nitrene) |
| Carboxylic acids | EDAC activation => amine Base/alkyl halide Chloroformate/alcohol Diazoalkane |
| Terminal cysteine | Hetero aryl/Aryl cyanides |
| Terminal serine | Oxidation (followed by aldehyde reactive reagents |

In embodiments of the first aspect of the present invention, B1 is Q or B2 is Q or B3 is Q or B4 is Q or B5 is Q. In particular, B1 is Q or B2 is Q or B3 is Q.

In embodiments of the first aspect of the present invention, one of B1 or B2 or B3 is Q. Q is selected from the following group: a hydrazine unit, a hydrazide unit, hydroxylamino unit, F, TAD. The other substituents, which are not Q, are: A1=H, A2=H, A3=H, A4=H, A5=H, Y1=H, Y2=H, B1=H, B2=H, B3=H, B4=H and B5=H.

In embodiments of the first aspect of the present invention, one of B1 or B2 or B3 is Q. Q is selected from the following group: a hydrazine unit, a hydrazide unit, hydroxylamino unit, F, TAD. The other substituents, which are not Q, are: A1 alkoxy, in particular methoxy, A2=H, A3=H, A4=H, A5=H, Y1=H, Y2=H, B1=B2=H, B3=H, B4=H and B5=H.

In embodiments of the first aspect of the present invention, one of B1 or B2 or B3 is Q. Q is selected from the following group: a hydrazine unit, a hydrazide unit, hydroxylamino unit, F, TAD. The other substituents, which are not Q, are: A1=H, A2=alkoxy, in particular methoxy, A=3H, A4=alkoxy, in particular methoxy, A5=H, Y1=H Y2=H, B1=H, B2=H, B3=H, B4=H and B5=H.

In embodiments of the first aspect of the present invention, one of B1 or B2 or B3 is Q. Q is selected from the following group: a hydrazine unit, a hydrazide unit, hydroxylamino unit, F, TAD. The other substituents, which are not Q, are: A1=H, A2=alkoxy, in particular methoxy, A3=alkoxy, in particular methoxy, A4=alkoxy, in particular methoxy, A5=H, Y1=H, Y2=H, B1=H, B2=H, B3=H, B4=H and B5=H.

In embodiments of the first aspect of the present invention, one of B1 or B2 or B3 is Q. Q is selected from the following group: a hydrazine unit, a hydrazide unit, hydroxylamino unit, F, TAD. The other substituents, which are not Q, are: A1=H, A2=H, A3=H, A4=H, A5=alkoxy, in particular methoxy, Y1=H, Y2=H, B1=H, B2=H, B3=-NMe$_2$, B4=H and B5=H.

In embodiments of the first aspect of the present invention, one of B1 or B2 or B3 is Q. Q is selected from the following group: a hydrazine unit, a hydrazide unit, hydroxylamino unit, F, TAD. The other substituents, which are not Q, are: A1=H, A2=tertiary butyl, A3=H, A4=tertiary butyl, A5=H, Y1 and Y2 form a condensed ring system, B1=H, B2=H, B3=H, B4=H and B5=H.

In embodiments of the first aspect of the present invention, one of B1 or B2 or B3 is Q. Q is selected from the following group: a hydrazine unit, a hydrazide unit, hydroxylamino unit, F, TAD. The other substituents, which are not Q, are: A1=H, A2=H, A3=H, A4=H, A5=H, Y1 and Y2 form a condensed ring system, B1=H, B2=H, B3=H, B4=H and B5=H.

In embodiments of the first aspect of the present invention, Q is acetomethylhydrazide.

In embodiments of the first aspect of the present invention, A1 is H or methoxy.

In embodiments of the first aspect of the present invention, A2 is H, tert-butyl or methoxy.

In embodiments of the first aspect of the present invention, A3 is H or methoxy.

In embodiments of the first aspect of the present invention, A4 is H, tert-butyl or methoxy.

In embodiments of the first aspect of the present invention, A5 is H or methoxy.

In embodiments of the first aspect of the present invention, Y1 is H or forms with Y2 a condensed aromatic or heteroaromatic ring structure.

In embodiments of the first aspect of the present invention, Y2 is H or forms with Y12 a condensed aromatic or heteroaromatic ring structure.

In embodiments of the first aspect of the present invention, B3 is H or N,N dimethylamineamine.

In embodiments of the first aspect of the present invention, B4 is H.

In embodiments of the first aspect of the present invention, B5 is H.

In embodiments of the first aspect of the present invention, B1 or B2 or B3 is Q, wherein Q is acetomethylhydrazide, wherein A1 is H or methoxy, wherein A2 is H, tert-butyl or methoxy, wherein A3 is H or methoxy, wherein A4 is H, tert-butyl or methoxy, wherein A5 is H or methoxy, wherein Y1 is H or forms with Y2 a condensed aromatic or heteroaromatic ring structure, wherein Y2 is H or forms with Y12 a condensed aromatic or heteroaromatic ring structure, wherein B3 is H or N,N dimethylamineamine, wherein B4 is H, wherein B5 is H.

In embodiments of the first aspect of the present invention, A1 is H.

In embodiments of the first aspect of the present invention, A2 is H, tert-butyl or methoxy.

In embodiments of the first aspect of the present invention, A3 is H or methoxy.

In embodiments of the first aspect of the present invention, A4 is H, tert-butyl or methoxy.

In embodiments of the first aspect of the present invention, A5 is H.

In embodiments of the first aspect of the present invention, Y1 is H or forms with Y2 a condensed aromatic or heteroaromatic ring structure.

In embodiments of the first aspect of the present invention, Y2 is H or forms with Y1 a condensed aromatic or heteroaromatic ring structure.

In embodiments of the first aspect of the present invention, B3 is H.

In embodiments of the first aspect of the present invention, B4 is H.

In embodiments of the first aspect of the present invention, B5 is H.

In embodiments of the first aspect of the present invention, the other substituents A1, A2, A3, A4, A5, B1, B2, B3, B4, B5, which are not forming the coupling group Q, are each independently selected from hydrogen, methyl, ethyl, propyl, cyclopropyl, isopropyl, butyl, tert-butyl, N,N dimethylamine or methoxy.

In embodiments of the first aspect of the present invention, the compound is charged.

In embodiments of the first aspect of the present invention, the compound is positively charged.

In embodiments of the first aspect of the present invention, the compound is permanent positively charged. In particular, the compound is one-time permanent positively charged. This can mean that the sum of the net charge is one-time permanent positive.

In embodiments of the first aspect of the present invention, the positively charge is part of a pyridinium.

In embodiments of the first aspect of the present invention, the permanent positive charge is located at the nitrogen of the pyridiunium moiety. The compound comprises a pyridinium cation.

In embodiments of the first aspect of the present invention, Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine. Hydrogen, alkyl and/or substituted aromatic are preferred embodiments.

In embodiments of the first aspect of the present invention, Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

In embodiments of the first aspect of the present invention, the compound comprises a counter ion for forming a salt. In particular, the counter ion is permanent negatively charged.

In embodiments of the first aspect of the present invention, the compound comprises a counter ion for forming a salt, wherein the counter ion is selected from the following group: Cl$^-$, Br$^-$, F$^-$, formate, trifluoroacetate, PF$_6^-$, sulfonate, phosphate, acetate.

In embodiments of the first aspect of the present invention, the compound of formula I is selected from the following group:

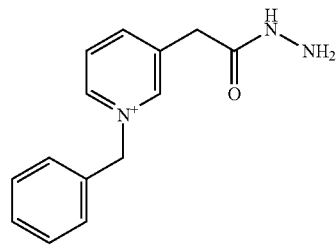

Label 1

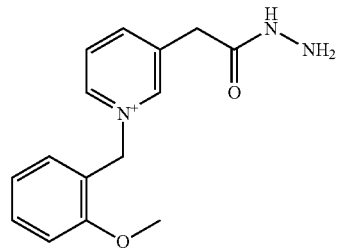

Label 2

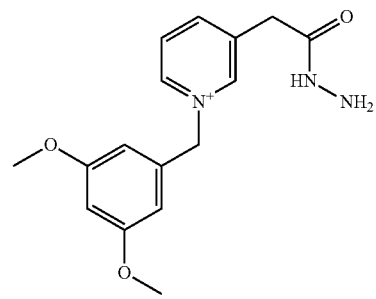

Label 3

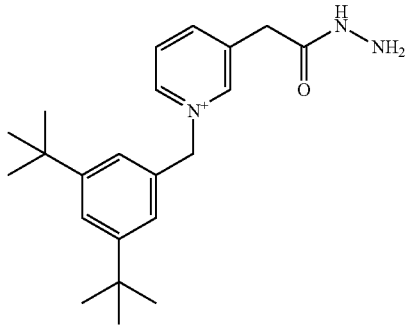

Label 4

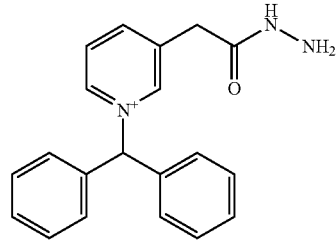

Label 5

Label 6

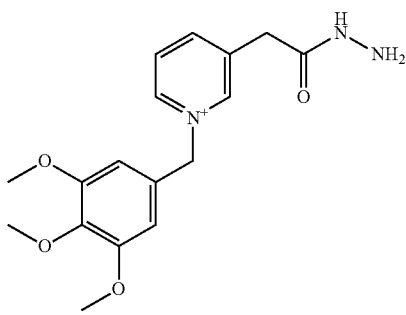

Label 7

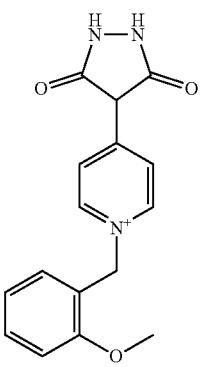

Label 8

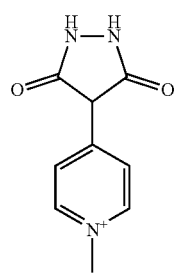

Label 9

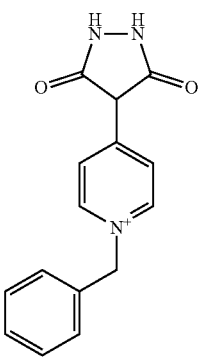

Label 10

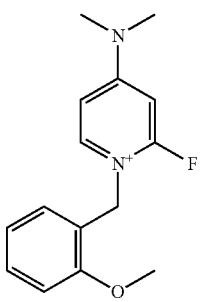

Label 11

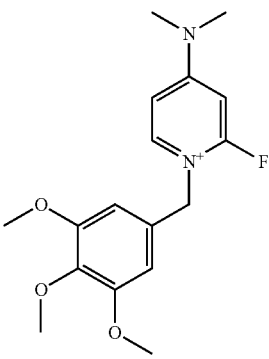

Label 12

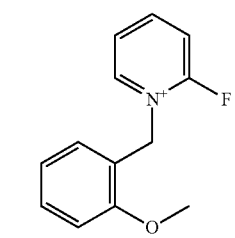

Each of the labels 1 to 12 mentioned above can form the compound alone or in combination with a counterion.

Stabilization of carbocation after neutral loss fragmentation at benzylic position enables fragment loss at low energy giving a highly dominant fragmentation pathway enabling high signal enhancement. In some embodiments, especially with meta substitution pattern favorable LC (liquid chromatography) elution characteristics can be observed. Either one of the two E/Z stereoisomers which can form in hydrazides or oximes (e.g. for testosterone labeling) can predominantly being generated or both isomers co-elute. This increases sensitivity due to better S/N (signal to noise ratio).

Alkylated pyridine can be fragmented at intermediate energy at N position. Alkylated pyridine combined with stabilized benzylic cation as loss fragment resulted in lower energy fragmentations and highly dominant fragmentation pathway enabling high signal enhancement. Either one of the two E/Z stereoisomers which can form from hydrazides or hydroxylamine (e.g. for testosterone labeling) can predominantly being generated or both isomers co-elute. This increases sensitivity electron donating substituents A1, A2, A3, A3, A4 and/or A5 (e.g. OMe). According to embodiments of the first aspect of the invention, a high signal enhancement can be achieved with Y1=H, Y2=H, A1=OMe, A2=H, A3=H, A4=H, A5=H, n=1 and K=hydrazide.

In a second aspect, the present invention relates to a composition comprising the compound of formula I as disclosed in detail above with regard to first aspect of the present invention. All embodiments mentioned for the first aspect of the invention apply for the second aspect of the invention and vice versa.

In a third aspect, the present invention relates to a kit comprising the compound of formula I as disclosed in detail herein above with regard to first aspect of the present invention or the composition of the second aspect of the present invention as disclosed in detail herein above. All embodiments mentioned for the first aspect of the invention and/or second aspect of the invention apply for the third aspect of the invention and vice versa.

In a fourth aspect, the present invention relates to a complex for detecting an analyte using mass spectrometry comprising a binding analyte and a binding compound, which are covalently linked to each other, in particular wherein the complex is formed by chemical reaction of the analyte and the compound of first aspect of the invention and/or in particular wherein the analyte is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof. All embodiments mentioned for the first aspect of the invention and/or second aspect of the invention and/or third aspect of the invention apply for the fourth aspect of the invention and vice versa.

In embodiments of the fourth aspect of the present invention, the binding complex of formula III resulting from the formation of a covalent bond between the compound of compound of formula I with a functional group present in the analyte molecule. Depending on the reactive unit K of the compound of formula I, and the functional group of the analyte molecule, the skilled person is well able to determine the covalent bond formed between the two.

In embodiments of the fourth aspect of the present invention, the binding compound comprises the formulae III and IV:

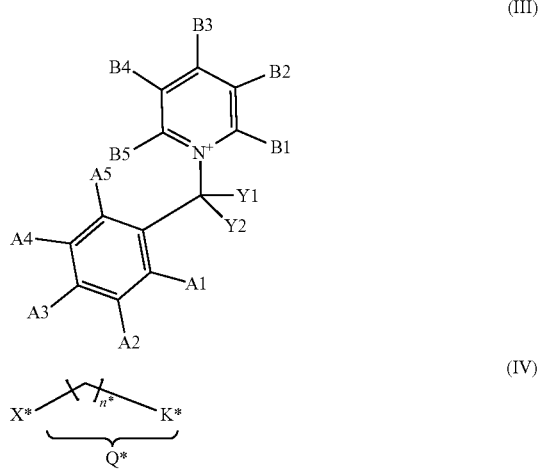

wherein one of the substituents B1, B2, B3, B4, B5 is a coupling group Q*, which forms a covalent bond with the analyte, wherein the other substituents A1, A2, A3, A4, A5, B1, B2, B3, B4, B5 are each independently selected from hydrogen, halogen, alkyl, N-acylamino, alkoxy, thioalkoxy, hydroxy, cyano, alkoxycarbonyl, alkoxythiocarbonyl, acyl, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, isotope or derivative thereof, wherein Y1 and Y2 are each independently selected from hydrogen, methyl, ethyl, methoxy, amine or wherein Y1 and Y2 form a ring structure, which is selected from substituted cycloalkyl, unsubstituted cycloalkyl, substituted aromatic, benzylic, unsubstituted aromatic, substituted heteroaromatic, unsubstituted heteroaromatic, wherein n* is 0, 1, 2, 3, 4 or 5, wherein the binding analyte is covalently bonded via K*, and wherein X* is a binding carbon-atom of the pyridinium cation of formula III. In particular the binding analyte is covalently bonded via K* for pyridinium-hydrazide and pyridinium-1,2,4-triazoline-3,5-dione. In the case of fluoro-pyridinium: K*=X* and n*=0.

In embodiments of the fourth aspect of the present invention, each of A1, A2, A3. A4, A5, B1, B2, B3, B4, B5, Y1 and Y2 of formula III has the same meaning as mentioned above for the first aspect of the present invention (A1, A2, A3, A4, A5, B1, B2, B3, B4, B5, Y1 and Y2 of formula I).

In embodiments of the fourth aspect of the present invention, the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof.

In embodiments of the fourth aspect of the present invention, Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

In embodiments of the fourth aspect of the present invention, X* has the same meaning as X mentioned above for the first aspect of the present invention.

In embodiments of the fourth aspect of the present invention, K* results from the formation of a covalent bond between the reactive unit K of compound of formula I with a functional group present in the analyte molecule. Depending on the reactive unit K of compound of formula I, and the functional group of the analyte molecule, the skilled person is well able to determine the covalent bond formed between the two.

Further, it is also contemplated within the scope of the present invention that a functional group present on an analyte molecule can be first converted into another group that is more readily available for reaction with reactive unit K of compounds of formula I.

In embodiments of the fourth aspect of the present invention, the analyte is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof.

In embodiments of the fourth aspect of the present invention, the analyte molecule comprises a functional group selected from the group consisting of carbonyl group, diene group, hydroxyl group, amine group, imine group, thiol group, diol group, phenolic group, expoxid group, disulfide group, and azide group, each of which is capable of forming a covalent bond with reactive unit K of compound of formula I.

In embodiments of the fourth aspect of the present invention, the analyte molecule is selected from the group consisting of steroids, ketosteroids, secosteroids, amino acids, peptides, proteins, carbohydrates, fatty acids, lipids, nucleosides, nucleotides, nucleic acids and other biomolecules including small molecule metabolites and cofactors as well as therapeutic drugs, drugs of abuse, toxins or metabolites thereof.

In embodiments of the fourth aspect of the present invention, the analyte molecule comprises a carbonyl group as functional group which is selected from the group consisting of a carboxylic acid group, aldehyde group, keto group, a masked aldehyde, masked keto group, ester group, amide group, and anhydride group.

In embodiments of the fourth aspect of the present invention, the carbonyl group is an amide group, the skilled person is well aware that the amide group as such is a stable group, but that it can be hydrolyzed to convert the amide group into a carboxylic acid group and an amino group. Hydrolysis of the amide group may be achieved via acid/base catalysed reaction or by enzymatic process either of which is well-known to the skilled person. In embodiments of the fourth aspect of the present invention, wherein the carbonyl group is a masked aldehyde group or a masked keto group, the respective group is either a hemiacetal group or acetal group, in particular a cyclic hemiacetal group or acetal group. In embodiments of the fourth aspect of the present invention, the acetal group, is converted into an aldehyde or keto group before reaction with the compound of formula I.

In embodiments of the first aspect of the present invention, the carbonyl group is a keto group. In embodiments of the first aspect of the present invention, the keto group may be transferred into an intermediate imine group before reacting with the reactive unit of compounds of formula I. In embodiments of the first aspect of the present invention, the analyte molecule comprising one or more keto groups is a ketosteroid. In particular embodiments of the first aspect of the present invention, the ketosteroid is selected from the group consisting of testosterone, epitestosterone, dihydrotestosterone (DHT), desoxymethyltestosterone (DWI), tetrahydrogestrinone (THG), aldosterone, estrone, 4-hydroxyestrone, 2-methoxyestrone, 2-hydroxyestrone, 16-ketoestradiol, 16-alpha-hydroxyestrone, 2-hydroxyestrone-3-methyl ether, prednisone, prednisolone, pregnenolone, progesterone, dehydroepiandrosterone (DHEA), 17-hydroxypregnenolone, 17-hydroxyprogesterone, androsterone, epiandrosterone, Δ4-androstenedione, 11-deoxycortisol, corticosterone, 21-deoxycortisol, 11-deoxycorticosterone, allopregnanolone and aldosterone.

In embodiments of the fourth aspect of the present invention, the carbonyl group is a carboxyl group. In embodiments of the first aspect of the present invention, the carboxyl group reacts directly with the compound of formula I or it is converted into an activated ester group before reaction with the compound of formula I. In embodiments of the first aspect of the present invention, the analyte molecule comprising one or more carboxyl groups is selected from the group consisting of Δ8-tetrahydrocannabinolic acid, benzoylecgonin, salicylic acid, 2-hydroxyhenzoic acid, gabapentin, pregabalin, valproic acid, vancomycin, methotrexate, mycophenolic acid, montelukast, repaglinide, furosemide, telmisartan, gemfibrozil, diclofenac, ibuprofen, indomethacin, zomepirac, isoxepac and penicillin. In embodiments of the first aspect of the present invention, the analyte molecule comprising one or more carboxyl groups is an amino acid selected from the group consisting of arginine, lysine, aspartic acid, glutamic acid, glutamine, asparagine, histidine, serine, threonine, tyrosine, cysteine, tryptophan, alanine, isoleucine, leucine, methionine, phenylalanine, valine, proline and glycine.

In embodiments of the fourth aspect of the present invention, the carbonyl group is an aldehyde group. In embodiments of the first aspect of the present invention, the aldehyde group may be transferred into an intermediate imine group before reacting with the reactive unit of compounds of formula I. In embodiments of the first aspect of the present invention, the analyte molecule comprising one or more aldehyde groups is selected from the group consisting of pyridoxal, N-acetyl-D-glucosamine, alcaftadine, streptomycin and josamycin.

In embodiments of the fourth aspect of the present invention, the carbonyl group is an carbonyl ester group. In embodiments of the first aspect of the present invention, the analyte molecule comprising one or more ester groups is selected from the group consisting of cocaine, heroin, Ritalin, aceclofenac, acetylcholine, amcinonide, amiloxate, amylocaine, anileridine, aranidipine artesunate and pethidine.

In embodiments of the fourth aspect of the present invention, the carbonyl group is an anhydride group. In embodiments of the first aspect of the present invention, the analyte molecule comprising one or more anhydride groups is selected from the group consisting of cantharidin, succinic anhydride, trimellitic anhydride and maleic anhydride.

In embodiments of the fourth aspect of the present invention, the analyte molecule comprises one or more diene groups, in particular to conjugated diene groups, as functional group. In embodiments of the first aspect of the present invention, the analyte molecule comprising one or more diene groups is a secosteroid. In embodiments, the secosteroid is selected from the group consisting of cholecalciferol (vitamin D3), ergocalciferol (vitamin D2), calcifediol, calcitriol, tachysterol, lumisterol and tacalcitol. In particular, the secosteroid is vitamin D, in particular vitamin D2 or D3 or derivates thereof. In particular embodiments, the secosteroid is selected from the group consisting of vitamin D2, vitamin D3, 25-hydroxyvitamin D2, 25-hydroxyvitamin D3 (calcifediol), 3-epi-25-hydroxyvitamin D2, 3-epi-25-hydroxyvitamin D3, 1,25-dihydroxyvitamin D2, 1,25-dihydroxyvitamin D3 (calcitriol), 24,25-dihydroxyvitamin D2, 24,25-dihydroxyvitamin D3. In embodiments of the first aspect of the present invention, the analyte molecule comprising one or more diene groups is selected from the group consisting of vitamin A, tretinoin, isotretinoin, alitretinoin, natamycin, sirolimus, amphotericin B, nystatin, everolimus, temsirolimus and fidaxomicin.

In embodiments of the fourth aspect of the present invention, the analyte molecule comprises one or more hydroxyl group as functional group. In embodiments of the first aspect of the present invention, the analyte molecule comprises a single hydroxyl group or two hydroxyl groups. In embodiments wherein more than one hydroxyl group is present, the two hydroxyl groups may be positioned adjacent to each other (1,2-diol) or may be separated by 1, 2 or 3 C atoms (1,3-diol, 1,4-diol, 1,5-diol, respectively). In particular embodiments of the first aspect, the analyte molecule comprises a 1,2-diol group. In embodiments, wherein only one hydroxyl group is present, said analyte is selected from the group consisting of primary alcohol, secondary alcohol and tertiary alcohol. In embodiments of the first aspect of the present invention, wherein the analyte molecule comprises one or more hydroxyl groups, the analyte is selected from the group consisting of benzyl alcohol, menthol, L-carnitine, pyridoxine, metronidazole, isosorbide mononitrate, guaifenesin, clavulanic acid, Miglitol, zalcitabine, isoprenaline, aciclovir, methocarbamol, tramadol, venlafaxine, atropine, clofedanol, alpha-hydroxyalprazolam, alpha-Hydroxytriazolam, lorazepam, oxazepam, Temazepam, ethyl glucuronide, ethyl morphine, morphine, morphine-3-glucuronide, buprenorphine, codeine, dihydrocodeine, p-hydroxypropoxyphene, O-desmethyltramadol, Desmetramadol, dihydroquinidine and quinidine. In embodiments of the first aspect of the present invention, wherein the analyte molecule comprises more than one hydroxyl groups, the analyte is selected from the group consisting of vitamin C, glucosamine, mannitol, tetrahydrobiopterin, cytarabine, azacitidine, ribavirin, floxuridine, Gemcitabine, Streptozotocin, adenosine, Vidarabine, cladribine, estriol, trifluridine, clofarabine, nadolol, zanamivir, lactulose, adenosine monophosphate, idoxuridine, regadenoson, lincomycin, clindamycin, Canagliflozin, tobramycin, netilmicin, kanamycin, ticagrelor, epirubicin, doxorubicin, arbekacin, streptomycin, ouabain, amikacin, neomycin, framycetin, paromomycin, erythromycin, clarithromycin, azithromycin, vindesine, digitoxin, digoxin, metrizamide, acetyldigitoxin, deslanoside, Fludarabine, clofarabine, gemcitabine, cytarabine, capecitabine, vidarabine, and plicamycin.

In embodiments of the fourth aspect of the present invention, the analyte molecule comprises one or more thiol group (including but not limited to alkyl thiol and aryl thiol groups) as functional group. In embodiments of the first aspect of the present invention, the analyte molecule comprising one or more thiol groups is selected from the group consisting of thiomandelic acid, DL-captopril, DL-thiorphan, N-acetylcysteine, D-penicillamine, glutathione, L-cysteine, zofenoprilat, tiopronin, dimercaprol, succimer.

In embodiments of the fourth aspect of the present invention, the analyte molecule comprises one or more disulfide group as functional group. In embodiments of the first aspect of the present invention, the analyte molecule comprising one or more disulfide groups is selected from the group consisting of glutathione disulfide, dipyrithione, selenium sulfide, disulfiram, lipoic acid, L-cystine, fursultiamine, octreotide, desmopressin, vapreotide, terlipressin, linaclotide and peginesatide. Selenium sulfide can be selenium disulfide, $SeS_2$, or selenium hexasulfide, $Se_2S_6$.

In embodiments of the fourth aspect of the present invention, the analyte molecule comprises one or more epoxide group as functional group. In embodiments of the first aspect of the present invention, the analyte molecule comprising one or more epoxide groups is selected from the group consisting of Carbamazepine-10,11-epoxide, carfilzomib, furosemide epoxide, fosfomycin, sevelamer hydrochloride, cerulenin, scopolamine, tiotropium, tiotropium bromide, methylscopolamine bromide, eplerenone, mupirocin, natamycin, and troleandomycin.

In embodiments of the fourth aspect of the present invention, the analyte molecule comprises one or more phenol groups as functional group. In particular embodiments of the first aspect of the present invention, analyte molecules comprising one or more phenol groups are steroids or steroid-like compounds. In embodiments of the first aspect of the present invention, the analyte molecule comprising one or more phenol groups is a steroid or a steroid-like compound having an A-ring which is $sp^2$ hybridized and an OH group at the 3-position of the A-ring. In particular embodiments of the first aspect of the present invention, the steroid or steroid-like analyte molecule is selected from the group consisting of estrogen, estrogen-like compounds, estrone (E1), estradiol (E2), 17a-estradiol, 17b-estradiol, estriol (E3), 16-epiestriol, 17-epiestriol, and 16, 17-epiestriol and/or metabolites thereof. In embodiments, the metabolites are selected from the group consisting of estriol, 16-epiestriol (16-epiE3), 17-epiestriol (17-epiE3), 16,17-epiestriol (16,17-epiE3), 16-ketoestradiol (16-ketoE2), 16a-hydroxyestrone (16a-OHE1), 2-methoxyestrone (2-MeOE1), 4-methoxyestrone (4-MeOE1), 2-hydroxyestrone-3-methyl ether (3-MeOE1), 2-methoxyestradiol (2-MeOE2), 4-methoxyestradiol (4-MeOE2), 2-hydroxyestrone (2-OHE1), 4-hydroxyestrone (4-OHE1), 2-hydroxyestradiol (2-OHE2), estrone (E1), estrone sulfate (E1s), 17a-estradiol (E2a), 17b-estradiol (E2B), estradiol sulfate (E2S), equilin (EQ), 17a-dihydroequilin (EQa), 17b-dihydroequilin (EQb), Equilenin (EN), 17-dihydroequilenin (ENa), 17α-dihydroequilenin, 17β-dihydroequilenin (ENb), Δ8,9-dehydroestrone (dE1), Δ8,9-dehydroestrone sulfate (dE1s), Δ9-tetrahydrocannabinol, mycophenolic acid. β or b can be used interchangeable. α and a can be used interchangeable.

In embodiments of the fourth aspect of the present invention, the analyte molecule comprises an amine group as functional group. In embodiments of the first aspect of the present invention, the amine group is an alkyl amine or an aryl amine group. In embodiments of the first aspect of the present invention, the analyte comprising one or more amine groups is selected from the group consisting of proteins and peptides. In embodiments of the first aspect of the present invention, the analyte molecule comprising an amine group is selected from the group consisting of 3,4-methylenedioxyamphetamine, 3,4-methylenedioxy-N-ethylamphetamine, 3,4-methylenedioxymethamphetamine, Amphetamine, Methamphetamine, N-methyl-1,3-benzodioxolylbutanamine, 7-aminoclonazepam, 7-aminoflunitrazepam, 3,4-dimethylmethcathinone, 3-fluoromethcathinone, 4-methoxymethcathinone, 4-methylethcathinone, 4-methylmethcathinone, amfepramone, butylone, ethcathinone, elephedrone, methcathinone, methylone, methylenedioxypyrovalerone, benzoylecgonine, dehydronorketamine, ketamine, norketamine, methadone, normethadone, 6-acetylmorphine, diacetylmorphine, morphine, norhydrocodone, oxycodone, oxymorphone, phencyclidine, norpropoxyphene, amitriptyline, clomipramine, dothiepin, doxepin, imipramine, nortriptyline, trimipramine, fentanyl, glycylxylidide, lidocaine, monoethylglycylxylidide, N-acetylprocainamide, procainamide, pregabalin, 2-Methylamino-1-(3,4-methylendioxyphenyl)butan, N-methyl-1,3-benzodioxolylbutanamine, 2-Amino-1-(3,4-methylendioxyphenyl)butan, 1,3-benzodioxolylbutanamine, normeperidine, O-Destramadol, desmetramadol, tramadol, lamotrigine, Theophylline, amikacin, gentamicin, tobramycin, vancomycin, Methotrexate, Gabapentin sisomicin and 5-methylcytosine.

In embodiments of the fourth aspect of the present invention, the analyte molecule is a carbohydrate or substance having a carbohydrate moiety, e.g. a glycoprotein or a nucleoside. In embodiments of the fourth aspect of the present invention, the analyte molecule is a monosaccharide, in particular selected from the group consisting of ribose, desoxyribose, arabinose, ribulose, glucose, mannose, galactose, fucose, fructose, N-acetylglucosamine, N-acetylgalactosamine, neuraminic acid, N-acetylneurominic acid, etc. In embodiments, the analyte molecule is an oligosaccharide, in particular selected from the group consisting of a disaccharide, trisaccharid, tetrasaccharide, polysaccharide. In embodiments of the fourth aspect of the present invention, the disaccharide is selected from the group consisting of sucrose, maltose and lactose. In embodiments of the fourth aspect of the present invention, the analyte molecule is a substance comprising above described mono-, di-, tri-, tetra-, oligo- or polysaccharide moiety.

In embodiments of the fourth aspect of the present invention, the analyte molecule comprises an azide group as functional group which is selected from the group consisting of alkyl or aryl azide. In embodiments of the fourth aspect of the present invention, the analyte molecule comprising one or more azide groups is selected from the group consisting, of zidovudine and azidocillin.

Such analyte molecules may be present in biological or clinical samples such as body liquids, e.g. blood, serum, plasma, urine, saliva, spinal fluid, etc., tissue or cell extracts, etc. In embodiments of the fourth aspect of the present invention, the analyte molecule(s) are present in a biological or clinical sample selected from the group consisting of blood, serum, plasma, urine, saliva, spinal fluid, and a dried blood spot. In some embodiments of the fourth aspect of the present invention, the analyte molecules may be present in a sample which is a purified or partially purified sample, e.g. a purified or partially purified protein mixture or extract.

In embodiments of the fourth aspect of the present invention, the reactive unit K is selected from the group consisting of a carbonyl reactive unit, a diene reactive unit, a hydroxyl reactive unit, an amino reactive unit, an imine reactive unit, a thiol reactive unit, a diol reactive unit, a phenol reactive unit, an epoxide reactive unit, a disulfide reactive unit, and a azido reactive unit.

In embodiments of the fourth aspect of the present invention, the reactive unit K is a carbonyl reactive unit, which is capable of reacting with any type of molecule having a carbonyl group. In embodiments of the fourth aspect of the present invention, the carbonyl reactive unit is selected from the group consisting of carboxyl reactive unit, keto reactive unit, aldehyde reactive unit, anhydride reactive unit, carbonyl ester reactive unit, and imide reactive unit. In embodiments of the fourth aspect of the present invention, the carbonyl-reactive unit may have either a super-nucleophilic N atom strengthened by the α-effect through an adjacent O or N atom NH2-N/O or a dithiol molecule. In embodiments of the fourth aspect of the present invention, the carbonyl-reactive unit is selected from the group:
  (i) a hydrazine unit, e.g. a H$_2$N—NH—, or H$_2$N—NR$^1$— unit, wherein R$^1$ is aryl, aryl containing one or more heteroatoms or C$_{1-4}$ alkyl, particularly C$_1$ or C$_2$ alkyl, optionally substituted e.g. with halo, hydroxyl, and/or C$_{1-3}$alkoxy,
  (ii) a hydrazide unit, in particular a carbo-hydrazide or sulfo-hydrazide unit, in particular a H$_2$N—NH—C(O)—, or H$_2$N—NR$^2$—C(O)— unit,
    wherein R$^1$ is aryl, aryl containing one or more heteroatoms or C$_{1-4}$ alkyl, particularly C$_1$ or C$_2$ alkyl, optionally substituted e.g. with halo, hydroxyl, and/or C$_{1-3}$ alkoxy,
  (iii) a hydroxylamino unit, e.g. a H$_2$N—O— unit, and
  (iv) a dithiol unit, particularly a 1,2-dithiol or 1,3-dithiol unit.

In embodiments of the fourth aspect of the present invention, wherein the carbonyl reactive unit is a carboxyl reactive unit, the carboxyl reactive units reacts with carboxyl groups on an analyte molecule. In embodiment of the fourth aspect of the present invention, the carboxyl reactive unit is selected from the group consisting of a diazo unit, an alkylhalide, amine, and hydrazine unit.

In embodiments of the fourth aspect of the present invention, the reactive unit K is a diene reactive unit, which is capable of reacting with an analyte comprising a diene group. In embodiments of the fourth aspect of the present invention, the diene reactive unit is selected from the group consisting of Cookson-type reagents, e.g. 1,2,4-triazoline-3,5-diones, which are capable to act as a dienophile.

In embodiments of the fourth aspect of the present invention, the reactive unit K is a hydroxyl reactive unit, which is capable of reacting with an analyte comprising a hydroxyl group. In embodiments of the fourth aspect of the present invention, the hydroxyl reactive units is selected from the group consisting of sulfonylchlorides, activated carboxylic esters (NHS, or imidazolide), and fluoro aromates/heteroaromates capable for nucleophilic substitution of the fluorine (T. Higashi J Steroid Biochem Mol Biol. 2016 September; 162:57-69). In embodiments of the fourth aspect of the present invention, the reactive unit K is a diol reactive unit which reacts with an diol group on an analyte molecule. In embodiments of the fourth aspect of the present invention, wherein the reactive unit is a 1,2 diol reactive unit, the 1,2 diol reactive unit comprises boronic acid. In further embodiments, diols can be oxidised to the respective ketones or aldehydes and then reacted with ketone/aldehyde-reactive units K.

In embodiments of the fourth aspect of the present invention, the amino reactive unit reacts with amino groups on an analyte molecule. In embodiments of the fourth aspect of the present invention, the amino-reactive unit is selected from the group consisting of active ester group such as N-hydroxy succinimide (NHS) ester or sulfo-NHS ester, pentafluoro phenyl ester, cabonylimidazole ester, quadratic acid esters, a hydroxybenzotriazole (HOBt) ester, 1-hydroxy-7-azabenzotriazole (HOAt) ester, and a sulfonylchloride unit.

In embodiments of the fourth aspect of the present invention, the thiol reactive unit reacts with an thiol group on an analyte molecule. In embodiments of the fourth aspect of the present invention, the thiole reactive unit is selected from the group consisting of haloacetyl group, in particular selected from the group consisting of Br/I—CH$_2$—C(=O)— unit, acrylamide/ester unit, unsaturated imide unit such as maleimide, methylsulfonyl phenyloxadiazole and sulfonylchloride unit.

In embodiments of the fourth aspect of the present invention, the phenol reactive unit reacts with phenol groups on an analyte molecule. In embodiments of the fourth aspect of the present invention, the phenol-reactive unit is selected from the group consisting of active ester unit such as N-hydroxy succinimide (NHS) ester or sulfo-NHS ester, pentafluoro phenyl ester, carbonylimidazole ester, quadratic acid esters, a hydroxybenzotriazole (HOBt) ester, 1-hydroxy-7-azabenzotriazole (HOAt) ester, and a sulfonylchloride unit.

Phenol groups present on an analyte molecule can be reacted with highly reactive electrophiles like triazolinedione (like TAD) via a reaction (H. Ban et al J. Am. Chem. Soc., 2010, 132 (5), pp 1523-1525) or by diazotization or alternatively by ortho nitration followed by reduction to an amine which could then be reacted with an amine reactive reagent. In embodiments of the first aspect of the present invention, the phenol-reactive unit is selected from the group consisting of fluoro-1-pyridinium.

In embodiments of the fourth aspect of the present invention, the reactive unit K is a epoxide reactive unit, which is capable of reacting with an analyte comprising a epoxide group. In embodiments of the fourth aspect of the present invention, the epoxide reactive unit is selected from the group consisting of amino, thiol, super-nucleophilic N atom strengthened by the α-effect through an adjacent O or N atom NH2-N/O molecule. In embodiments of the fourth aspect of the present invention, the epoxide reactive unit is selected from the group:

(i) a hydrazine unit, e.g. a $H_2N$—NH—, or $H_2N$—$NR^1$— unit, wherein $R^1$ is aryl, aryl containing one or more heteroatoms or $C_{1-4}$ alkyl, particularly $C_1$ or $C_2$ alkyl, optionally substituted e.g. with halo, hydroxyl, and/or $C_{1-3}$ alkoxy, (ii) a hydrazide unit, in particular a carbo-hydrazide or sulfo-hydrazide unit, in particular a $H_2N$—NH—C(O)—, or $H_2N$—$NR^2$—C(O)— unit, wherein $R^2$ is aryl, aryl containing one or more heteroatoms or $C_{1-4}$ alkyl, particularly $C_1$ or $C_2$ alkyl, optionally substituted e.g. with halo, hydroxyl, and/or $C_{1-3}$ alkoxy, and (iii) a hydroxylamino unit, e.g. a $H_2N$—O— unit.

In embodiments of the fourth aspect of the present invention, the reactive unit K is a disulfide reactive unit, which is capable of reacting with an analyte comprising a disulfide group. In embodiments of the fourth aspect of the present invention, the disulfide reactive unit is selected from the group consisting of thiol. In further embodiments, disulfide group can be reduced to the respective thiol group and then reacted with thiol reactive units K.

In embodiments of the fourth aspect of the present invention, the reactive unit K is a azido reactive unit which reacts with azido groups on an analyte molecule. In embodiments of the fourth aspect of the present invention, the azido-reactive unit reacts with azido groups through azide-alkyne cycloaddition. In embodiments of the fourth aspect of the present invention, the azido-reactive unit is selected from the group consisting of alkyne (alkyl or aryl), linear alkyne or cyclic alkyne. The reaction between the azido and the alkyne can proceed with or without the use of a catalyst. In further embodiments of the fourth aspect of the present invention the azido group can be reduced to the respective amino group and then reacted with amino reactive units K.

In embodiments of the fourth aspect of the present invention, the binding analyte is covalently bonded via K*. In particular, in case of pyridinium-hydrazide. K* is the hydrazide and the nitrogen from the hydrazide binds covalently with the analyte. In case of 4-pyridinium 1,2,4-triazoline-3,5-dione K* is 1,2,4-triazoline-3,5-dione and the nitrogen/nitrogens from the 1,2,4-triazoline-3,5-dione bind covalently with the analyte. In case of fluoro-pyridinium K* is K*=X* and n*=0, the carbon X* binds covalently with the analyte.

In embodiments of the fourth aspect of the present invention, K* is selected from the group consisting of hydrazide, hydrazine, hydroxylamine, Br, F, 4-substituted 1,2,4-triazoline-3,5-dione (TAD), 4-Phenyl-1,2,4-triazoline-3,5-dione (PTAD), 4-pyridinium-1,2,4-triazoline-3,5-dione and reactive carbonyl group.

In embodiments of the fourth aspect of the present invention, X* is the binding carbon-atom of the pyridinium cation of formula III to the group, which is selected from the group consisting of B1, B2, B3, B4 and B5.

In embodiments of the fourth aspect of the present invention, n* is 0, 1, 2, 3, 4 or 5. Preferably n* is 0 or 1.

In embodiments of the fourth aspect of the present invention, the binding compound is covalently linked via a carbonyl group, hydroxyl group or diene group of the analyte to form the said complex.

In a fifth aspect, the present invention relates to the use of the compound of formula I for mass spectrometric determination of the analyte. Preferably the mass spectrometric determination comprises a tandem mass spectrometric determination, in particular a triple quadrupole mass spectrometric determination. All embodiments mentioned for the first aspect of the invention and/or second aspect of the invention and/or third aspect of the invention and/or fourth aspect of the invention apply for the fifth aspect of the invention and vice versa.

In embodiments of the fifth aspect of the present invention, the mass spectrometric determination comprises a tandem mass spectrometric determination, in particular a triple quadrupole mass spectrometric determination.

In embodiments of the fifth aspect of the present invention, the use of a compound of formula I comprises the use as a derivatization reagent. In embodiments of the fifth aspect of the present invention, the compound of formula I is used to increase the sensitivity of MS measurement. In embodiments, the compound of formula I is used to detect the analyte of interest at a lower level of detection, in particular at a lower level of quantification.

In embodiments of the fifth aspect of the present invention, the compound of formula I according to the present invention comprises a reactive unit K which is capable of reacting with an analyte molecule. The reactive unit K is capable of reacting with an analyte molecule such that a covalent bond between the compound of formula I and the analyte molecule is formed. In embodiments of the fifth aspect of the present invention, the reactive unit K forms a covalent bond with the compound of formula I. In particular, the covalent bond is formed between the reactive unit K of compound of formula I and a functional group present in the analyte molecule.

Depending on the functional groups present in the analyte molecule to be determined, the skilled person will select an appropriate reactive unit K for compound of formula I. It is within common knowledge to decide which reactive unit K will qualify for binding to a functional group of an analyte of interest.

What has been said above for the analyte applies mutatis mutandis for the analyte in the context of the fifth aspect of the present invention.

Analyte molecules may be present in biological or clinical samples such as body liquids, e.g. blood, serum, plasma, urine, saliva, spinal fluid, etc., tissue or cell extracts, etc. In embodiments of the fifth aspect of the present invention, the analyte molecule(s) are present in a biological or clinical sample selected from the group consisting of blood, serum, plasma, urine, saliva, spinal fluid, and a dried blood spot. In some embodiments of the fifth aspect of the present invention, the analyte molecules may be present in a sample which is a purified or partially purified sample, e.g. a purified or partially purified protein mixture or extract.

In a sixth aspect, the present invention relates to a method for mass spectrometric determination of an analyte comprising the steps of:

(a) reacting the analyte with the compound of formula I as disclosed herein above with regard to the first aspect of the present invention, whereby a complex as disclosed herein above with regard to the fourth aspect of the present invention is formed, (b) subjected the complex from step (a) to a mass spectrometric analysis.

Preferably step (b) comprises:

(i) subjecting an ion of the complex to a first stage of mass spectrometric analysis, whereby the ion of the complex is characterized according to its mass/charge (m/z) ratio, (ii) causing fragmentation of the complex ion, whereby a first entity, particularly a low-molecular weight entity, and a daughter ion of the complex is generated, wherein the daughter ion of the complex differs in its m/z ratio from the complex ion, and (iii) subjecting the daughter ion of the complex to a second stage of mass spectrometric analysis, whereby the daughter ion of the complex is characterized according to its m/z ratio, and/or wherein (ii) may further comprise alternative fragmentation of the complex ion, whereby a second entity, different from the first entity is released and a second daughter ion of the complex is generated, and wherein (iii) may further comprise subjecting the first and second daughter ions of the complex to a second stage of mass spectrometric analysis, whereby the first and second daughter ions of the complex are characterized according to their m/z ratios.

Step (a) may occur at different stages within the sample preparation workflow prior to mass spectrometric determination. The samples comprising an analyte molecule may be pre-treated and/or enriched by various methods. The pre-treatment method is dependent upon the type of sample, such as blood (fresh or dried), plasma, serum, urine, or saliva, whereas the enrichment method is dependent on the analyte of interest. It is well known to the skilled person which pre-treatment sample is suitable for which sample type. It is also well-known to the skilled person which enrichment method is suitable for which analyte of interest.

In embodiments of the sixth aspect of the present invention, step (a) of the present method for the mass spectrometric determination of an analyte molecule takes place i) subsequent to a pre-treatment step of the sample, ii) subsequent to a first enrichment of the sample, or iii) subsequent to a second enrichment of the sample.

In embodiments of the sixth aspect of the present invention, wherein the sample is a whole blood sample, it is assigned to one of two pre-defined sample pre-treatment (PT) workflows, both comprising the addition of an internal standard (ISTD) and a hemolysis reagent (HR) followed by a pre-defined incubation period (Inc), where the difference between the two workflows is the order in which the internal standard (ISTD) and a hemolysis reagent (HR) are added. In embodiments water is added as a hemolysis reagents, in particular in an amount of 0.5:1 to 20:1 ml water/ml sample, in particular in an amount of 1:1 to 10:1 ml water/ml sample, in particular in an amount of 2:1 to 5:1 mL water/ml sample.

In embodiments of the sixth aspect of the present invention, the sample is a urine sample, it is assigned to one of other two pre-defined sample PT workflows, both comprising the addition of an internal standard and an enzymatic reagent followed by a pre-defined incubation period, where the difference between the two workflows is the order in which the internal standard and a enzymatic reagent are added. An enzymatic reagent is typically a reagent used for glucuronide cleavage or protein cleavage or any pre-processing of analyte or matrix. In an additional step a derivatization reagent such as compounds of the present invention as disclosed herein above or below, is added followed by an incubation period.

In embodiments of the sixth aspect of the present invention, the enzymatic reagent in selected from the group consisting of glucuronidase, (partial) exo- or endo-deglycoslation enzymes, or exo- or endo preoteases. In embodiments, glucoronidase is added in amount of 0.5-10 mg/ml, in particular in an amount of 1 to 8 mg/ml, in particular in an amount of 2 to 5 mg/ml.

In embodiments of the sixth aspect of the present invention, wherein the sample is plasma or serum it is assigned to another pre-defined PT workflow including only the addition of an internal standard (ISTD) followed by a pre-defined incubation time.

It is well-known to the skilled person which incubation time and temperature to choose for a sample treatment, chemical reaction or method step considered and as named herein above or below. In particular, the skilled person knows that incubation time and temperature depend upon each other, in that e.g. a high temperature typically leads to a shorter incubation period and vise versa. In embodiments of the sixth aspect of the invention, the incubation temperature is in a range of 4 to 45° C., in particular in a range of 10-40° C., in particular at 20-37° C. In embodiments, the incubationen time is in the range of 30 sec to 120 min, in particular 30 sec to 1 min, sec to 5 min, 30 sec to 10 min, 1 min to 10 min, or 1 min to 20 min, 10 min to 30 min, 30 min to 60 min, or 60 min to 120 min. In particular embodiments, the incubation time is a multiple of 36 sec.

Accordingly, the embodiments of the present method, step a) takes place subsequent to either of the above disclosed pre-treatment process of the sample.

In embodiment of the sixth aspect of the present invention, the reaction of the compound of formula I and the analyte molecule in step a) takes place before any enrichment process, the compound of formula I is added to the pre-treated sample of interest. Accordingly, the complex of the analyte molecule and the compound of formula I is formed after the pre-treatment and prior to the first enrichment process. The complex is thus, subjected to the first enrichment process and to the second enrichment process before being subjected to the mass spectrometric analysis of step b).

The pre-treated sample may be further subjected to an analyte enrichment workflow. The analyte enrichment workflow may include one or more enrichment methods. Enrichment methods are well-known in the art and include but are not limited to chemical enrichment methods including but not limited to chemical precipitation, and enrichment methods using solid phases including but not limited to solid phase extraction methods, bead workflows, and chromatographic methods (e.g. gas or liquid chromatography).

In embodiments of the sixth aspect of the present invention, a first enrichment workflow comprises the addition of of a solid phase, in particular of solid beads, carrying analyte-selective groups to the pre-treated sample. In embodiments of the sixth aspect of the present invention, a first enrichment workflow, comprises the addition of magnetic or paramagnetic beads carrying analyte-selective groups to the pre-treated sample. In embodiments of the sixth aspect of the present invention, the addition of the magnetic beads comprises agitation or mixing. A pre-defined incubation period for capturing the analyte(s) of interest on the bead follows. In embodiments of the sixth aspect of the present invention, the workflow comprises a washing step (W1) after incubation with the magnetic beads. Depending on the analyte(s) one or more additional washing steps (W2) are performed. One washing step (W1, W2) comprises a series of steps including magnetic bead separation by a magnetic bead handling unit comprising magnets or electromagnets, aspiration of liquid, addition of a washing buffer, resuspension of the magnetic beads, another magnetic bead separation step and another aspiration of the liquid. Moreover washing steps may differ in terms of type of solvent (water/organic/salt/pH), apart from volume and number or combination of washing cycles. It is well-known to the skilled person how to choose the respective parameters. The last washing step (W1, W2) is followed by the addition of an elution reagent followed by resuspension of the magnetic beads and a pre-defined incubation period for releasing the analyte(s) of interest from the magnetic beads.

The bound-free magnetic beads are then separated and the supernatant containing derivatized analyte(s) of interest is captured.

In embodiments of the sixth aspect of the present invention, a first enrichment workflow comprises the addition of magnetic beads carrying matrix-selective groups to the pre-treated sample. In embodiments of the sixth aspect of the present invention, the addition of the magnetic beads comprises agitation or mixing. A pre-defined incubation period for capturing the matrix on the bead follows. Here, the analyte of interest does not bind to the magnetic beads but remains in the supernatant. Thereafter, the magnetic beads are separated and the supernatant containing the enriched analyte(s) of interest is collected.

In embodiments of the sixth aspect of the present invention, the supernatant is subjected to a second enrichment workflow. Here, the supernatant is transferred to the LC station or is transferred to the LC station after a dilution step by addition of a dilution liquid. Different elution procedures/reagents may also be used, by changing e.g. the type of solvents (water/organic/salt/pH) and volume. The various parameters are well-known to the skilled person and easily chosen.

In embodiments of the sixth aspect of the present invention, wherein step a) of the present method did not take place directly after the pre-treatment method, step a) may take place after the first enrichment workflow using magnetic beads as described herein above.

In embodiments of the sixth aspect of the present invention, wherein analyte specific magnetic beads are used, the compounds of formula I as disclosed herein above or below, is added to the sample of interest after the washing steps (W1, W2) are concluded either prior to, together with or subsequent with the elution reagent, which is followed by an incubation period (defined time and temperature).

In embodiments of the sixth aspect of the present invention, the bound-free magnetic beads are then separated and the supernatant containing the complex of step a) is collected. In embodiments of the sixth aspect of the present invention, the supernatant containing the complex of step a) is transferred to a second enrichment workflow, in particular either directly transferred to an LC station or after a dilution step by addition of a dilution liquid.

In embodiments of the sixth aspect of the present invention, wherein matrix-specific magnetic beads are used, the compounds of formula I as disclosed herein above or below, is added to the sample of interest before or after the magnetic beads are separated. In embodiments of the sixth aspect of the present invention, the supernatant containing the complex of step a) is transferred to a second enrichment workflow, in particular either directly to an LC station or after a dilution step by addition of a dilution liquid.

Accordingly, in embodiments of the sixth aspect of the present invention, wherein the reaction of the compound of formula I and the analyte molecule in step a) takes place subsequent to a first enrichment process, the compound of formula I is added to the sample of interest after the first enrichment process, in particular a first enrichment process using magnetic beads, is concluded. Accordingly, the sample is first pre-treated as described herein above, is then subjected to a first enrichment process, in particular using magnetic beads, carrying analyte selective groups as described herein above, and prior to, simultaneously with or subsequently to the elution from the beads, the compound of formula I is added. Accordingly, the complex of the analyte molecule and the compound of formula I is formed after the first enrichment process and prior to the second enrichment process. The complex is thus, subjected to the second enrichment process before being subjected to the mass spectrometric analysis of step b).

In another embodiment of the sixth aspect of the present invention, step (a) of the present method takes place after a second analyte enrichment workflow. In the second enrichment workflow, chromatographic separation is used to further enrich the analyte of interest in the sample. In embodiments of the sixth aspect of the present invention, the chromatographic seperation is gas or liquid chromatography. Both methods are well known to the skilled person. In embodiments of the sixth aspect of the present invention, the liquid chromatography is selected from the group consisting of HPLC, rapid LC, micro-LC, flow injection, and trap and elute.

In embodiments of the sixth aspect of the present invention, step a) of the present method takes place concurrent with or subsequent to the chromatographic seperation. In embodiment of the sixth aspect of the present invention, the compound of formula I is added to the column together with the elution buffer. In alternative embodiments, the compound of formula f is added post column.

In embodiments of the sixth aspect of the present invention, the first enrichment process includes the use of analyte selective magnetic beads. In embodiments of the sixth aspect of the present invention, the second enrichment process includes the use of chromatographic separation, in particular using liquid chromatography.

Accordingly, in embodiments of the sixth aspect of the present invention, wherein the reaction of the compound of formula I and the analyte molecule in step a) takes place subsequent to a second enrichment process, the compound of formula I is added to the sample of interest after the second enrichment process using chromatography, in particular liquid chromatography, is concluded. Accordingly, in this case, the sample is first pre-treated as described herein above, is then subjected to a first enrichment process, in particular using magnetic bead, as described herein above, followed by chromatographic separation, in particular using liquid chromatography, and subsequent to chromatographic separation the compound of formula i is added. Accordingly, the complex of the binding analyte molecule and the binding compound of formula I is formed after the second enrichment process. The complex is thus, not subjected to a enrichment process before being subjected to the mass spectrometric analysis of step b).

In a seventh aspect, the present invention relates to a compound of formula V:

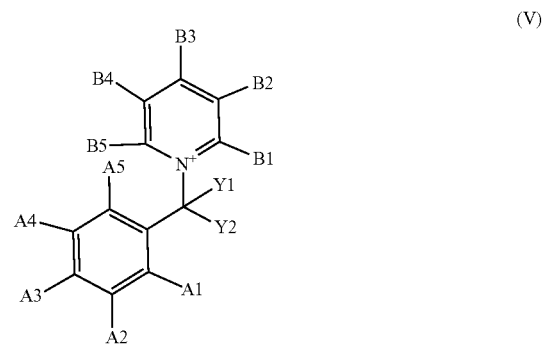

(V)

wherein one of the substituents B1, B2, B3, B4, B5 is a coupling group Q, which is capable of forming a covalent bond with the analyte, wherein the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof, wherein Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

All embodiments mentioned for the first aspect of the invention and/or second aspect of the invention and/or third aspect of the invention and/or fourth aspect of the invention and/or fifth aspect of the invention and/or sixth aspect of the invention apply for the seventh aspect of the invention and vice versa. In particular, all embodiments mentioned for the first aspect of the invention, e.g. for A1, A2, A3, A4, A5, B1, B2, B3, B4, B5, Y1 and Y2, apply for the compound of formula V. In particular, the compound of formula V is capable to be used for mass spectrometric determination. Alternatively or in addition, the compound of formula V can be used in other technical fields, e.g. chemical labeling and drug delivery.

In embodiments of the seventh aspect of the invention, the other substituents A1, A2, A3, A4, A5, B1, B2, B3, B4, B5 are each independently selected from hydrogen, halogen, alkyl, N-acylamino, alkoxy, thioalkoxy, hydroxy, cyano, alkoxycarbonyl, alkoxythiocarbonyl, acyl, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, isotope or derivative thereof.

In embodiments of the seventh aspect of the invention, Y1 and Y2 are each independently selected from hydrogen, methyl, ethyl, methoxy, amine or wherein Y1 and Y2 form a ring structure, which is selected from substituted cycloalkyl, unsubstituted cycloalkyl, substituted aromatic, benzylic, unsubstituted aromatic, substituted heteroaromatic, unsubstituted heteroaromatic.

In a eighth aspect, the present invention relates to a compound of formula VI:

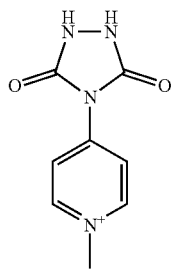

(VI). This compound shows good stability, binding affinity to an analyte and/or lead to an enhancement of the MS signal.

In a ninth aspect, the present invention relates to compound of formula VII:

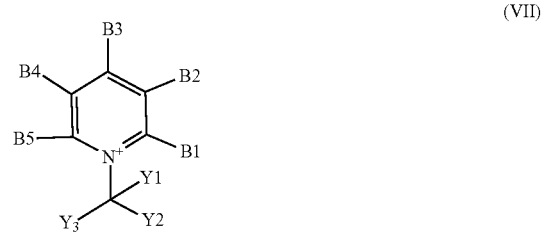

(VII)

wherein:
Y1=H,
Y2=H,
Y3 is H or

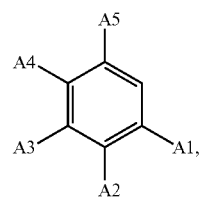

B3 is

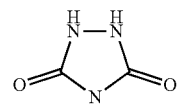

or its oxidized and reactive form:

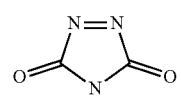

and
wherein the other substituents A1, A2, A3, A4, A5, B1, B2, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof. All embodiments mentioned for the first aspect of the invention and/or second aspect of the invention and/or third aspect of the invention and/or fourth aspect of the invention and/or fifth aspect of the invention and/or sixth aspect of the invention and/or seventh aspect of the invention and/or eighth aspect of the invention apply for the ninth aspect of the invention and vice versa.

In embodiments of the present invention, a clinical diagnostic system comprises the compound of the first aspect of the invention and/or the composition of the second aspect of the present invention and/or the kit of the third aspect of the present invention and/or the complex of the fourth aspect of the present invention and/or compound of the seventh aspect of the present invention. Additionally or optionally, the compound of the first aspect of the present invention is used for mass spectrometric determination of an analyte, wherein the clinical diagnostic system comprises the mass spectrometric determination. Additionally or optionally, the method for mass spectrometric determination of an analyte of the sixth aspect of the present invention is performed by the clinical diagnostic system.

A "clinical diagnostics system" is a laboratory automated apparatus dedicated to the analysis of samples for in vitro diagnostics. The clinical diagnostics system may have different configurations according to the need and/or according to the desired laboratory workflow. Additional configurations may be obtained by coupling a plurality of apparatuses and/or modules together. A "module" is a work cell, typically smaller in size than the entire clinical diagnostics system, which has a dedicated function. This function can be analytical but can be also pre-analytical or post analytical or it can be an auxiliary function to any of the pre-analytical function, analytical function or post-analytical function. In particular, a module can be configured to cooperate with one or more other modules for carrying out dedicated tasks of a sample processing workflow, e.g. by performing one or more pre-analytical and/or analytical and/or post-analytical steps. In particular, the clinical diagnostics system can comprise one or more analytical apparatuses, designed to execute respective workflows that are optimized for certain types of analysis, e.g. clinical chemistry, immunochemistry, coagulation, hematology, liquid chromatography separation, mass spectrometry, etc. Thus the clinical diagnostic system may comprise one analytical apparatus or a combination of any of such analytical apparatuses with respective workflows, where pre-analytical and/or post analytical modules may be coupled to individual analytical apparatuses or be shared by a plurality of analytical apparatuses. In alternative pre-analytical and/or post-analytical functions may be performed by units integrated in an analytical apparatus. The clinical diagnostics system can comprise functional units such as liquid handling units for pipetting and/or pumping and/or mixing of samples and/or reagents and/or system fluids, and also functional units for sorting, storing, transporting, identifying, separating, detecting. The clinical diagnostic system can comprise a sample preparation station for the automated preparation of samples comprising analytes of interest, a liquid chromatography (LC) separation station comprising a plurality of LC channels and/or a sample preparation/LC interface for inputting prepared samples into any one of the LC channels. The clinical diagnostic system can further comprise a controller programmed to assign samples to pre-defined sample preparation workflows each comprising a pre-defined sequence of sample preparation steps and requiring a pre-defined time for completion depending on the analytes of interest. The clinical diagnostic system can further comprise a mass spectrometer (MS) and an LC/MS interface for connecting the LC separation station to the mass spectrometer. The term "automatically" or "automated" as used herein is a broad term and is to be given its ordinary and customary meaning to a person of ordinary skill in the art and is not to be limited to a special or customized meaning.

The term specifically may refer, without limitation, to a process which is performed completely by means of at least one computer and/or computer network and/or machine, in particular without manual action and/or interaction with a user.

A "sample preparation station" can be a pre-analytical module coupled to one or more analytical apparatuses or a unit in an analytical apparatus designed to execute a series of sample processing steps aimed at removing or at least reducing interfering matrix components in a sample and/or enriching analytes of interest in a sample. Such processing steps may include any one or more of the following processing operations carried out on a sample or a plurality of samples, sequentially, in parallel or in a staggered manner: pipetting (aspirating and/or dispensing) fluids, pumping fluids, mixing with reagents, incubating at a certain temperature, heating or cooling, centrifuging, separating, filtering, sieving, drying, washing, resuspending, aliquoting, transferring, storing, etc.).

A "liquid chromatography (LC) separation station" is an analytical apparatus or module or a unit in an analytical apparatus designed to subject the prepared samples to chromatographic separation in order for example to separate analytes of interest from matrix components, e.g. remaining matrix components after sample preparation that may still interfere with a subsequent detection, e.g. a mass spectrometry detection, and/or in order to separate analytes of interest from each other in order to enable their individual detection. According to an embodiment, the LC separation station is an intermediate analytical apparatus or module or a unit in an analytical apparatus designed to prepare a sample for mass spectrometry and/or to transfer the prepared sample to a mass spectrometer. In particular, the LC separation station is a multi-channel LC station comprising a plurality of LC channels.

The clinical diagnostic system, e.g. the sample preparation station, may also comprise a buffer unit for receiving a plurality of samples before a new sample preparation start sequence is initiated, where the samples may be individually randomly accessible and the individual preparation of which may be initiated according to the sample preparation start sequence.

The clinical diagnostic system makes use of LC coupled to mass spectrometry more convenient and more reliable and therefore suitable for clinical diagnostics. In particular, high-throughput, e.g. up to 100 samples/hour or more with random access sample preparation and LC separation can be obtained while enabling online coupling to mass spectrometry. Moreover the process can be fully automated increasing the walk-away time and decreasing the level of skills required.

In further embodiments, the present invention relates to the following aspects:

1. A compound of formula I for mass spectrometric determination of an analyte:

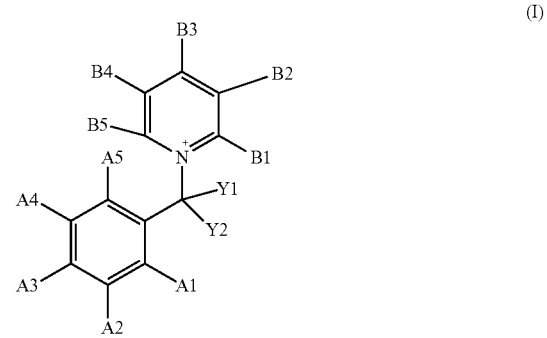

(I)

wherein one of the substituents B1, B2, B3, B4, B5 is a coupling group Q, which is capable of forming a covalent bond with the analyte, wherein the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof, wherein Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

2. The compound of aspect 1, wherein the coupling group Q is bonded to X according to the following formula II:

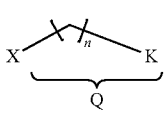

(II)

wherein K is a reactive unit, which is capable of forming the covalent bond with the analyte, wherein n is 0, 1, 2, 3, 4 or 5, and wherein X is a binding carbon-atom of the pyridinium cation of formula I.

3. The compound of aspect 2, wherein K is capable of reacting with a carbonyl group, phenol group, amine, hydroxyl group or diene group of the analyte.

4. The compound of aspects 2 or 3, wherein K is selected from the group consisting of hydrazide, hydrazine, hydroxylamine, Br, F, 4-substituted 1,2,4-triazoline-3,5-dione (TAD) and reactive carbonyl.

5. The compound of any of the proceeding aspects, wherein Q is selected from methyl hydrazide, methyl hydrazine, methyl hydroxylamine.

6. The compound of any of the proceeding aspects 2 to 5, wherein n=0 and K is Br or n=0 and K is F.

7. The compound of any of the proceeding aspects, wherein the other substituents A1, A2, A3, A4, A5, B1, B2, B3, B4, B5, which are not forming the coupling group Q, are each independently selected from hydrogen, methyl, ethyl, propyl, cyclopropyl, isopropyl, butyl, tert-butyl, N,N dimethylamine or methoxy.

8. The compound of any of the proceeding aspects, wherein B1 is Q or B2 is Q or B3 is Q.

9. The compound of any of the proceeding aspects, wherein Q is acetohydrazide or carbonylhydrazide.

10. The compound of any of the proceeding aspects, wherein Q is 4-substituted 1,2,4-triazoline-3,5-dione (TAD).

11. The compound of any of the proceeding aspects, wherein Q is F and n=0.

12. The compound of any of the proceeding aspects, wherein A1 is H or methoxy.

13. The compound of any of the proceeding aspects, wherein A2 is H, tert-butyl or methoxy.

14. The compound of any of the proceeding aspects, wherein A3 is H or methoxy.

15. The compound of ally of the proceeding aspects, wherein A4 is H, tert-butyl or methoxy.

16. The compound of any of the proceeding aspects, wherein A5 is H or methoxy.

17. The compound of any of the proceeding aspects, wherein Y1 is H or forms with Y2 a condensed aromatic or heteroaromatic ring structure.

18. The compound of any of the proceeding aspects, wherein Y2 is H or forms with Y1 a condensed aromatic or heteroaromatic ring structure.

19. The compound of any of the proceeding aspects, wherein B3 is H or N,N dimethylamine.

20. The compound of any of the proceeding aspects, wherein B4 is H.

21. The compound of any of the proceeding aspects, wherein B5 is H.

22. The compound of any of the proceeding aspects, wherein B4 or B5 is N,N dimethylamine.

23. The compound of any of the proceeding aspects, wherein A1 is H.

24. The compound of any of the proceeding aspects, wherein A2 is H, tert-butyl or methoxy.

25. The compound of any of the proceeding aspects, wherein A3 is H or methoxy.

26. The compound of any of the proceeding aspects, wherein A4 is H, tert-butyl or methoxy.

27. The compound of any of the proceeding aspects, wherein A5 is H.

28. The compound of any of the proceeding aspects, wherein Y1 is H or forms with Y2 a condensed aromatic or heteroaromatic ring structure.

29. The compound of any of the proceeding aspects, wherein Y2 is H or forms with Y1 a condensed aromatic or heteroaromatic ring structure.

30. The compound of any of the proceeding aspects, wherein B3 is H.

31. The compound of any of the proceeding aspects, wherein B4 is H.

32. The compound of any of the proceeding aspects, wherein B5 is H.

33. The compound of any of the proceeding aspects, which is permanent positively charged.

34. The compound of any of the proceeding aspects, which comprises a counter ion for forming a salt, wherein the counter ion is preferably selected from the following group: $Cl^-$, $Br^-$, $F^-$, formate, trifluoroacetate, $PF_6^-$, sulfonate, phosphate, acetate.

35. A composition comprising the compound of any of aspects 1 to 34.

36. A kit comprising the compound of any of aspects 1 to 34 or the composition of aspect 35.

37. A complex for detecting an analyte using mass spectrometric determination comprising a binding analyte and a binding compound, which are covalently linked to each other, in particular wherein the complex is formed by chemical reaction of the analyte and the compound of any of aspects 1 to 34.

38. The complex of aspects 37, wherein the binding compound comprises the formulae III and IV:

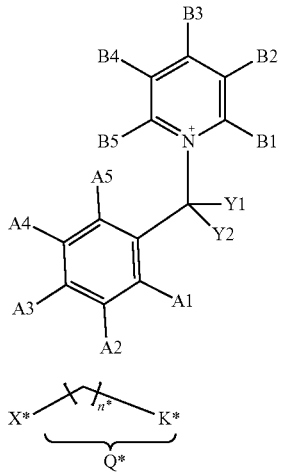

wherein one of the substituents B1, B2, B3, B4, B5 is a coupling group Q*, which forms a covalent bond with the analyte,
wherein the other substituents A1, A2, A3, A4, A5, B1, B2, B3, B4, B5 are each independently selected from hydrogen, halogen, alkyl, N-acylamino, alkoxy, thioalkoxy, hydroxy, cyano, alkoxycarbonyl, alkoxythiocarbonyl, acyl, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, isotope or derivative thereof,
wherein Y1 and Y2 are each independently selected from hydrogen, methyl, ethyl, methoxy, amine or wherein Y1 and Y2 form a ring structure, which is selected from substituted cycloalkyl, unsubstituted cycloalkyl, substituted aromatic, benzylic, unsubstituted aromatic, substituted heteroaromatic, unsubstituted heteroaromatic,
wherein n* is 0, 1, 2, 3, 4 or 5,
wherein the binding analyte is covalently bonded via K*, this is true for pyridinium-hydrazide and pyridinium-1,2,4-triazoline-3,5-dione, but in the case of fluoropyridinium K*=X* and n*=0, and
wherein X* is a binding carbon-atom of the pyridinium cation of formula III.

39. The complex of aspect 30 or 31, wherein K* is selected from the group consisting of hydrazide, hydrazine, hydroxylamine, Br, F, 4-substituted 1,2,4-triazoline-3,5-dione (TAD) and reactive carbonyl.

40. The complex of any of the proceeding aspects 37 to 39, wherein the analyte is selected from the group consisting of nucleic acid, amino acid, peptide, protein, metabolite, hormones, fatty acid, lipid, carbohydrate, steroid, ketosteroid, secosteroid, a molecule characteristic of a certain modification of another molecule, a substance that has been internalized by the organism, a metabolite of such a substance and combination thereof.

41. The complex of any of the proceeding aspects 37 to 40, wherein the binding compound is covalently linked via a carbonyl group, hydroxyl group or diene group of the analyte to form the said complex.

42. Use of the compound of any of aspects 1 to 34 for mass spectrometric determination of the analyte.

43. The use of the compound of aspects 42, wherein the mass spectrometric determination comprises a tandem mass spectrometric determination, in particular a triple quadrupole mass spectrometric determination.

44. A method for mass spectrometric determination of an analyte comprising the steps of:
(a) reacting the analyte with the compound of formula I as defined in anyone of aspects 1 to 34, whereby a complex as defined in anyone of aspects 37 to 41 is formed,
(b) subjected the complex from step (a) to a mass spectrometric analysis.

45. The method of aspect 44, wherein the mass spectrometric analysis step (b) comprises:
(i) subjecting an ion of the complex to a first stage of mass spectrometric analysis, whereby the ion of the complex is characterized according to its mass/charge (m/z) ratio,
(ii) causing fragmentation of the complex ion, whereby a first entity, particularly a low-molecular weight entity is released and a daughter ion of the complex is generated, wherein the daughter ion of the complex differs in its m/z ratio from the complex ion, and
(iii) subjecting the daughter ion of the complex to a second stage of mass spectrometric analysis, whereby the daughter ion of the complex is characterized according to its m/z ratio, and/or
wherein (ii) may further comprise alternative fragmentation of the complex ion, whereby a second entity, in particular a second entity, different from the first entity is released and a second daughter ion of the complex is generated, and
wherein (iii) may further comprise subjecting the first and second daughter ions of the complex to a second stage of mass spectrometric analysis, whereby the first and second daughter ions of the complex are characterized according to their m/z ratios.

46. A compound of formula V:

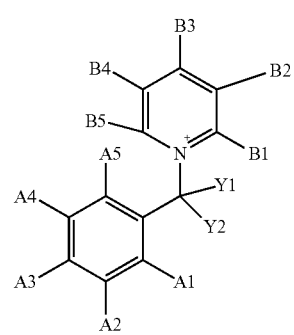

wherein one of the substituents B1, B2, B3, B4, B5 is a coupling group Q, which is capable of forming a covalent bond with the analyte,
wherein the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof, wherein Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

47. A compound of formula VI:

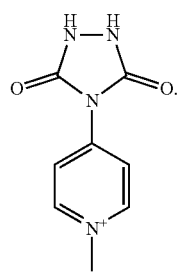

(VI)

48. A compound of formula VII:

(VII)

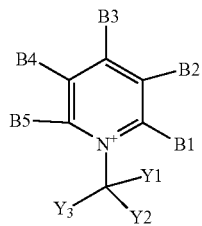

wherein:
Y1=H,
Y2=H,
Y3 is H or

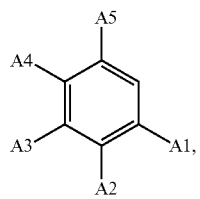

B3 is

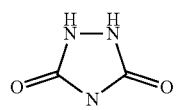

or its oxidized and reactive form:

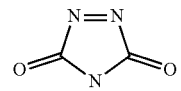

and wherein the other substituents A1, A2, A3, A4, A5, B1, B2, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof.

EXAMPLES

The following, examples are provided to illustrate, but not to limit the presently claimed invention.

Example 1: Synthesis of Label 1

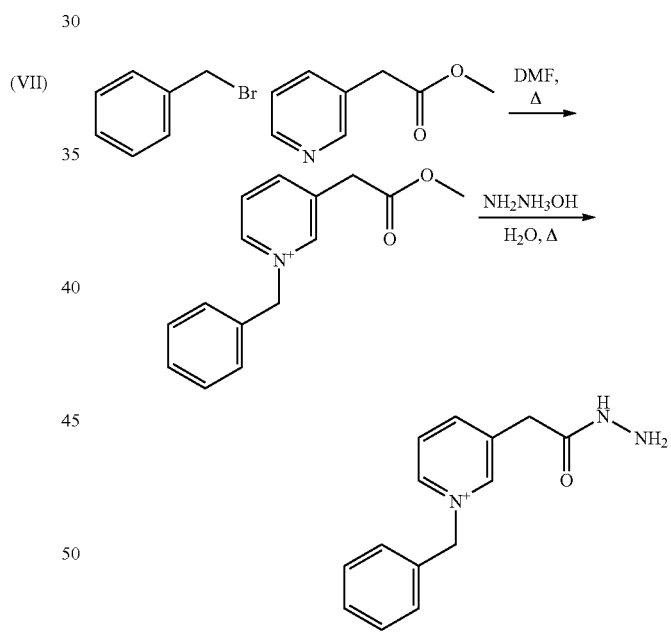

Step 1: Pyridine alkylation: Synthesis of methyl 2-(1-benzylpyridin-1-ium-3-yl)acetate formate

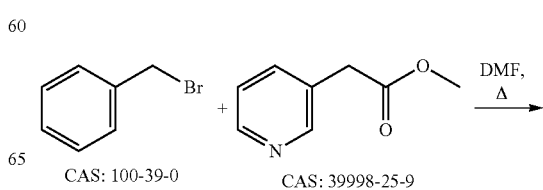

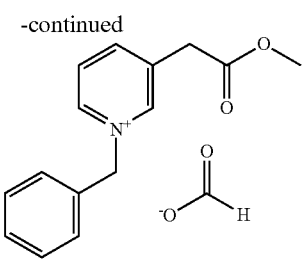

methyl 2-(1-benzylpyridin-1-ium-3-yl)acetate:formate

Methyl 3-pyridylacetate (0.87 mmol) and benzyl bromide (1.14 mmol) were dissolved in 3 mL DMF. The reaction mixture was stirred at 115° C. for 2 h. DMF was removed in vacuum and residue was purified by preparative HPLC. The pure fractions were collected and lyophilized to give 214 mg (85% yield) of the desired product of coloured oil.

HPLC purification method: Residue was dissolved in 4 mL 25 mM NH$_4$COOH aqueous solution. Colum: C-18 LiChroprep (45 g); Solvent A: H$_2$O+0.1% HCOOH; Solvent B: CH$_3$CN+0.1% HCOOH; Flow: 26 mL/min
  0-5 min: 95% A; 5% B
  5-30 min: 10% A; 90% B
  30-38 min: 10% A; 90% B $^1$H NMR (400 MHz, DMSO-d6) δ ppm 3.67 (s, 2H), 4.06 (s, 3H), 5.84 (s, 2H), 7.43-7.53 (m, 5H), 8.12-8.17 (m, 1H), 8.31 (s, 1H), 8.57 (d, J=8.16 Hz, 1H), 9.15 (d, J=6.15 Hz, 1H), 9.20 (s, 1H).

HPLC-MS (m/z) [M]+ calcd 242.1, found 242.2.

Step 2: Synthesis of [[2-(1-benzylpyridin-1-ium-3-yl)acetyl]amino]ammonium diformate

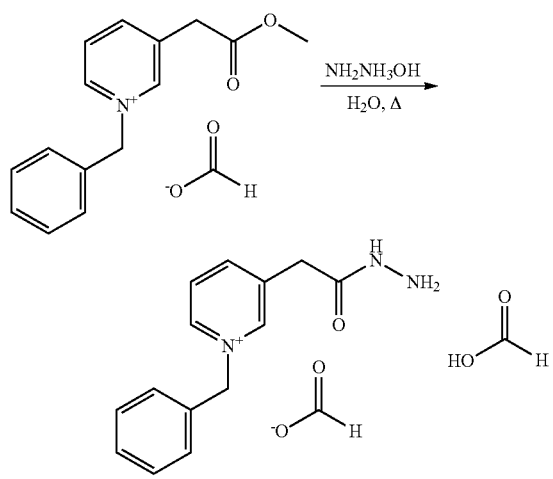

2-(1-benzylpyridin-1-ium-3-yl)acetohydrazide:formic acid:formate

Methyl 2-(1-benzylpyridin-1-ium-3-yl)acetate formate (0.74 mmol) was dissolved in 2 mL of water. Hydrazine monohydrate (0.74 mmol) was added and reaction mixture was stirred at room temperature (r.t.) for 2 h. The reaction mixture was purified by preparative HPLC. The pure fractions were collected and lyophilised to give 125 mg (58% yield) of the desired product as white solid.

HPLC purification method: The reaction mixture (2 mL) was loaded to column without any work up. Colum: C-18 LiChroprep (45 g); Solvent A: H$_2$O+0.1% HCOOH; Solvent B: CH$_3$CN+0.1% HCOOH; Flow: 26 mL/min
  0-8 min: 95% A; 5% B
  8-33 min: 10% A; 90% B
  33-38 min: 10% A; 90% B $^1$H NMR (400 MHz, DMSO-d6) δ ppm 3.67 (s, 2H), 5.81 (s, 2H), 7.39-7.49 (m, 5H), 8.10 (dd, J=7.97; 5.96 Hz, 1H), 8.42 (s, 1H), 8.46 (d, J=8.16 Hz, 1H), 9.07 (br d, J=6.15 Hz, 1H), 9.16 (s, 1H).

HPLC-MS (m/z) [M]+ calcd 242.1, found 242.2.

Example 2: Synthesis of Label 2

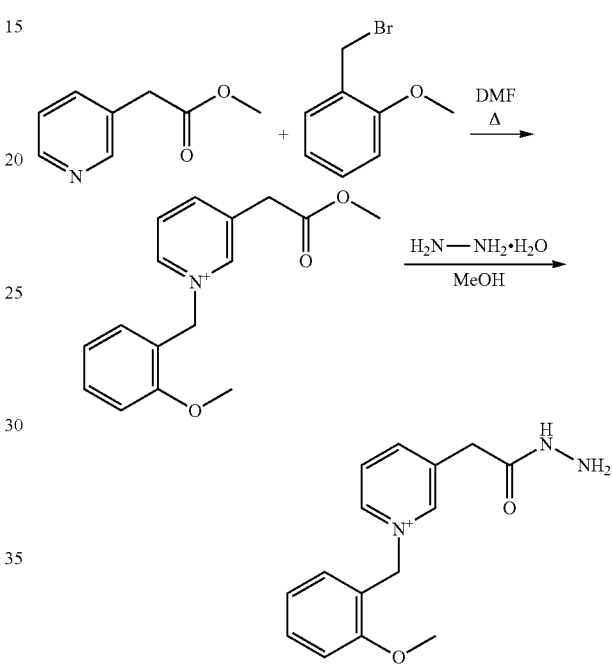

Step 1: Pyridine alkylation: Synthesis of methyl 2-[1-[(2-methoxyphenyl)methyl]pyridin-1-ium-3-yl] acetate trifluoroacetate

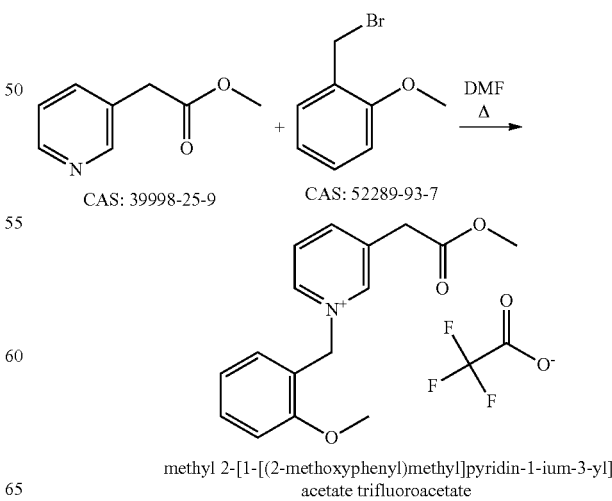

methyl 2-[1-[(2-methoxyphenyl)methyl]pyridin-1-ium-3-yl] acetate trifluoroacetate Methyl 3-pyridylacetate (0.87 mmol) and 1-(Bromomethyl)-2-methoxybenzene (1.14 mmol) were dissolved in 3 mL DMF. The reaction mixture was stirred at 115° C. for 2 h. DMF was removed in vacuum and residue was purified by preparative HPLC. The pure fractions were collected and lyophilized to give 167 mg (94% yield) of the desired product of coloured oil.

HPLC method C-18 column:

0 min: 100% H₂O 0.1% TFA, 0% CH₃CN 0.1% TFA;
0-60 min: 50% H₂O 0.1% TFA, 50% CH₃CN 0.1% TFA;
60-64 min: 2% H₂O 0.1% TFA; 98% CH₃CN 0.1% TFA;
64-80 min: 2% H₂O 0.1% TFA; 98% CH₃CN 0.1% TFA;
80-83 min: 60% H₂O 0.1% TFA; 40% CH₃CN 0.1% TFA;
83-89 min: 60% H₂O 0.1% TFA; 40% CH₃CN 0.1% TFA;
89-90 min: 60% H₂O 0.1% TFA; 40% CH₃CN 0.1% TFA.

$^1$H NMR (400 MHz, METHANOL-di) δ ppm 3.73 (s, 3H) 3.81 (s, 3H) 3.99 (s, 2H) 5.76 (s, 2H) 7.04-7.08 (m, 2H) 7.45-7.50 (m, 1H) 7.55 (dd, J=7.65, 1.5 Hz, 1H) 8.00 (dd, J=7.78, 6.65 Hz, 1H) 8.48 (d, J=8.03 Hz, 1H) 8.89 (d, J=6.15 Hz, 1H) 9.02 (s, 1H).

$^{13}$C NMR (101 MHz, METHANOL-d₄) δ ppm 36.12 (1C) 51.61 (1C) 54.66 (1C) 60.93 (1C) 111.14 (1C) 120.84 (1C) 120.93 (1C) 127.10 (1C) 131.20 (1C) 131.95 (1C) 136.00 (1C) 142.89 (1C) 145.34 (1C) 146.72 (1C) 158.07 (1C) 169.96 (1C).

HPLC-MS (m/z) [M]+ calcd 272.13, found 272.32.

Step 2: Synthesis of [2-[1-[(2-methoxyphenyl)methyl]pyridin-1-ium-3-yl]acetohydrazide bistrifluoroacetate

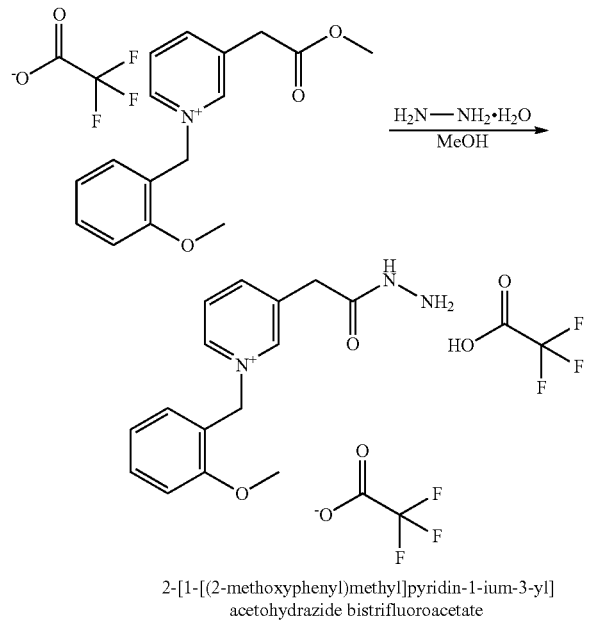

2-[1-[(2-methoxyphenyl)methyl]pyridin-1-ium-3-yl]acetohydrazide bistrifluoroacetate 2-[1-[(2-methoxyphenyl)methyl]pyridin-1-ium-3-yl]acetate trifluoroacetate (0.14 mmol) was dissolved in 1 mL MeOH. Hydrazine monohydrate (1.40 mmol) was added and reaction mixture was stirred at 50° C. for 3 h. The reaction mixture was purified by preparative HPLC. The pure fractions were collected and lyophilised to give 33 mg (46% yield) of the desired product as a yellow oil.

HPLC method C-18 column:

0 min: 100% H₂O 0.1% TFA, 0% CH₃CN 0.1% TFA;
0-30 min: 100% H₂O 0.1% TFA, 0% CH₃CN 0.1% TFA;
30-34 min: 2% H₂O 0.1% TFA; 98% CH₃CN 0.1% TFA:
34-50 min: 2% H₂O 0.1% TFA; 98% CH₃CN 0.1% TFA;
50-53 min: 60% H₂O 0.1% TFA; 40% CH₃CN 0.1% TFA;
53-59 min: 60% H₂O 0.1% TFA; 40% CH₃CN 0.1% TFA;
59-60 min: 60% H₂O 0.1% TFA; 40% CH₃CN 0.1% TFA.

$^1$H NMR (400 MHz, METHANOL-d₄) δ ppm 3.81 (s, 3H) 3.91 (s, 2H) 5.77 (s, 2H) 7.03-7.07 (m, 2H) 7.44-7.48 (m, 1H) 7.55 (dd, J=7.53, 1.63 Hz, 1H) 8.01 (dd, J=7.91, 6.27 Hz, 1H) 8.46-8.49 (m, 1H) 8.90 (dd, J=6.15, 1.13 Hz, 1H) 9.03 (s, 1H).

$^{13}$C NMR (101 MHz, METHANOL-d₄) δ ppm 35.58 (1C) 54.70 (1C) 60.93 (1C) 111.14 (1C) 120.84 (1C) 120.91 (1C) 127.15 (1C) 131.23 (1C) 131.95 (1C) 135.77 (1C) 143.07 (1C) 145.17 (1C) 146.53 (1C) 158.08 (1C) 168.03 (1C).

HPLC-MS (m/z) [M]+ calcd 272.14, found 272.06.

Example 3: Synthesis of Label 3

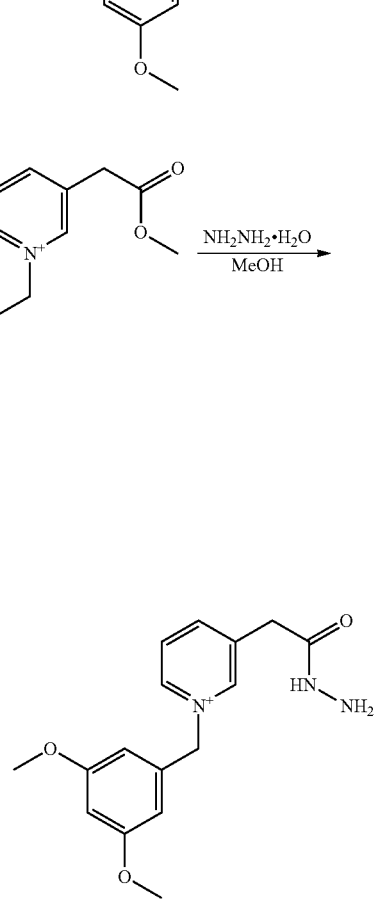

Step 1: Pyridine alkylation: Synthesis of methyl 2-[1-[(3,5-dimethoxyphenyl)methyl]pyridin-1-ium-3-yl]acetate trifluoroacetate

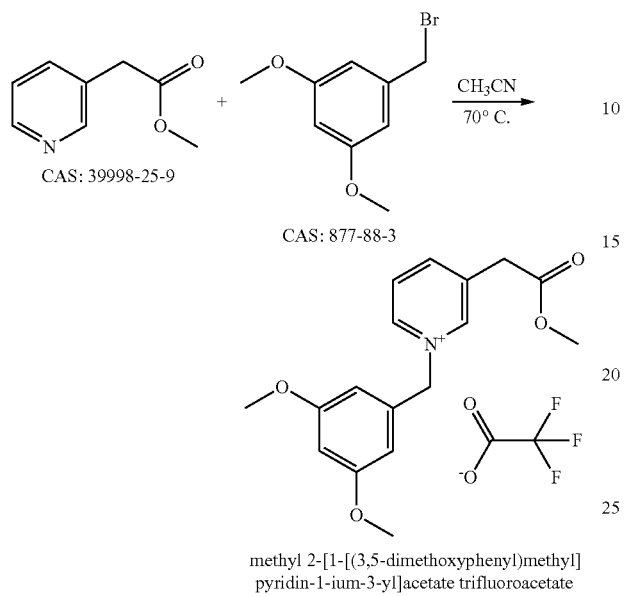

methyl 2-[1-[(3,5-dimethoxyphenyl)methyl] pyridin-1-ium-3-yl]acetate trifluoroacetate Methyl 3-pyridylacetate (0.53 mmol) and 3,5-Dimethoxybenzyl bromide (0.64 mmol) were dissolved in 3 mL DMF. The reaction mixture was stirred at 70° C. for 6 h. DMF was removed in vacuum and residue was purified by preparative HPLC. The pure fractions were collected and lyophilized to give 212 mg (96% yield) of the desired product as a oil.

HPLC method C-18 column:
0 min: 98% $H_2O$ 0.1% TFA, 2% $CH_3CN$ 0.1% TFA;
0-10 min: 98% $H_2O$ 0.1% TFA, 2% $CH_3CN$ 0.1% TFA;
10-60 min: 60% $H_2O$ 0.1% TFA; 40% $CH_3CN$ 0.1% TFA;
60-70 min: 10% $H_2O$ 0.1% TFA; 90% $CH_3CN$ 0.1% TFA.

$^1H$ NMR (400 MHz, METHANOL-d4) δ ppm 3.73 (s, 3H) 3.78 (s, 6H) 4.01 (s, 2H) 5.72 (s, 2H) 6.55 (t, J=2.26 Hz, 1H) 6.62 (d, J=2.26 Hz, 2 Hz) 8.06 (dd, J=7.91, 6.27 Hz, 1H) 8.54 (d, J=8.03 Hz, 1H) 8.95 (d, J=6.02 Hz, 1H) 9.07 (s, 1H).

$^{13}C$ NMR (101 MHz, METHANOL-$d_4$) δ ppm 36.18 (1C) 46.92 (1C) 51.65 (2C) 54.56 (1C) 64.38 (1C) 100.86 (1C) 106.42 (1C) 106.48 (2C) 127.61 (1C) 134.92 (1C) 136.56 (1C) 147.05 (1C) 161.86 (2C) 169.94 (1C).

HPLC-MS (m/z) [M]+ calcd 302.14, found 302.33.

Step 2: hydrazide formation: Synthesis of 2-[1-[(3,5-dimethoxyphenyl)methyl]pyridin-1-ium-3-yl]acetohydrazide bistrifluoroacetate

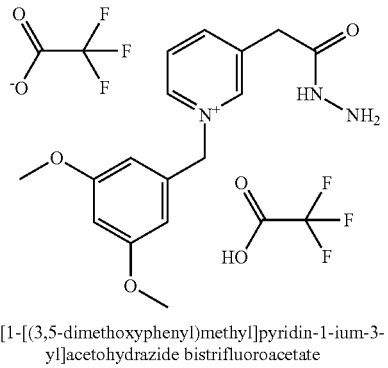

2-[1-[(3,5-dimethoxyphenyl)methyl]pyridin-1-ium-3-yl]acetohydrazide bistrifluoroacetate Methyl 2-[1-[(3,5-dimethoxyphenyl)methyl]pyridin-1-ium-3-yl]acetate trifluoroacetate (0.24 mmol) was dissolved in 2 mL of MeOH. Hydrazine monohydrate (2.40 mmol) was added and reaction mixture was stirred at r.t. for 2 h. The reaction mixture was purified by preparative HPLC. The pure fractions were collected and lyophilised to give 100 mg (79% yield) of the desired product as oil.

HPLC method C-18 column:
0 min: 98% $H_2O$ 0.1% TFA, 2% $CH_3CN$ 0.1% TFA;
0-10 min: 98% $H_2O$ 0.1% TFA, 2% $CH_3CN$ 0.1% TFA;
10-60 min: 60% $H_2O$ 0.1% TFA; 40% $CH_3CN$ 0.1% TFA;
60-70 min: 10% $H_2O$ 0.1% TFA; 90% $CH_3CN$ 0.1% TFA.

$^1H$ NMR (400 MHz, METHANOL-$d_4$) δ ppm 3.77 (s, 6H) 3.92 (s, 2H) 5.71 (s, 2H) 6.53 (t, J=2.20 Hz, 1H) 6.62 (d, J=2.10 Hz, 2H) 8.06 (dd, J=7.40, 6.53 Hz, 1H) 8.52 (d, J=7.78 Hz, 1H) 8.96 (d, J=6.00 Hz, 1H) 9.05 (s, 1H).

$^{13}C$ NMR (101 MHz, METHANOL-$d_4$) δ ppm 35.90 (1C) 54.56 (2C) 64.43 (1C) 100.84 (1C) 106.55 (2C) 127.63 (1C) 134.87 (1C) 136.83 (s, 1C) 142.85 (1C) 144.95 (1C) 146.84 (1C) 161.84 (2C) 170.42 (1C).

HPLC-MS (m/z) [M]+ calcd 302.15, found 302.35.

Example 4: Synthesis of Label 4

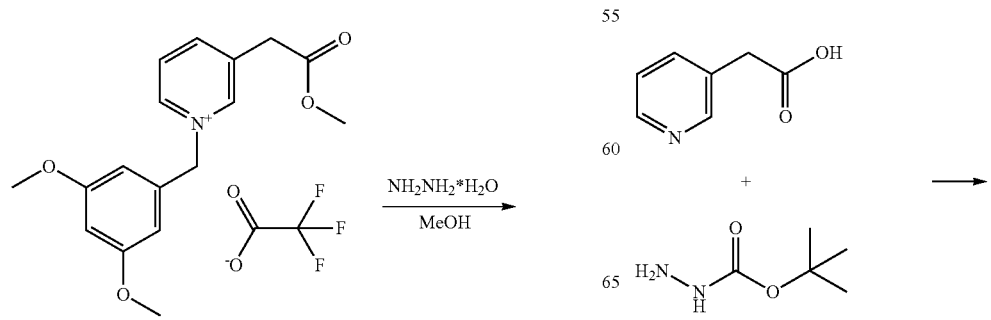

-continued

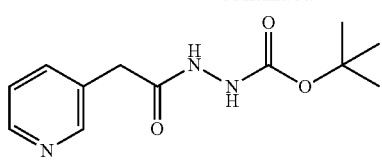

+

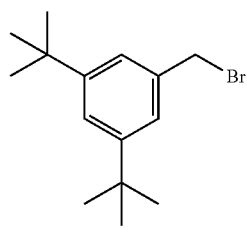

→ CH₃CN / Δ

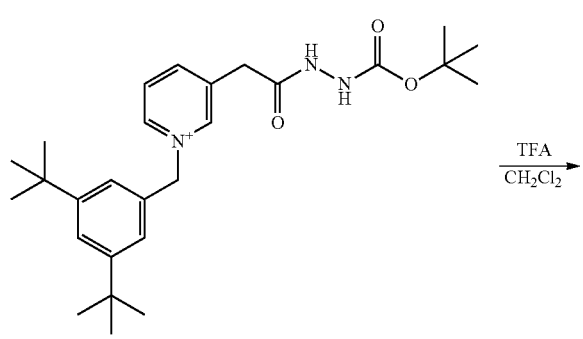

→ TFA / CH₂Cl₂

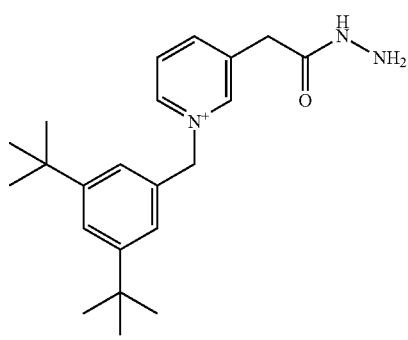

Step 1: Synthesis of tert-butyl N-[[2-(3-pyridyl)acetyl]amino]carbamate

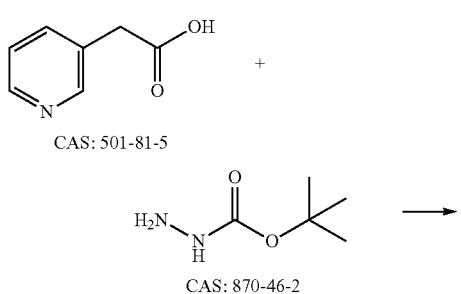

-continued

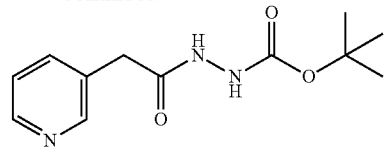

tert-butyl N-[[2-(3-pyridyl)acetyl]amino]carbamate

3-Pyridineacetic acid (500 mg, 3.65 mmol), tert-butyl carbazate (531 mg, 4.02 mmol) and EDC.HCl (796 mg, 4.15 mmol) were dissolved in dry DCM (3 mL) and stirred at room temperature (r.t.) for 1 d. Saturated NaHCO₃ (aq) was added and washed five times with DCM. The combined organic phases were washed with saturated NaCl (aq) and dried over Na₂SO₄. The solvent was removed under vacuum and the mixture was purified by flash chromatography (eluent EtOAc). The product was obtained as a white solid (852 mg, 93% yield).

$^1$H NMR (400 MHz, METHANOL-d₄) δ ppm 1.44 (s, 9H) 3.58 (s, 2H) 7.38 (ddd, J=7.87, 4.93, 0.75 Hz, 1H) 7.71-7.92 (m, 1H) 8.41 (dd, J=4.89, 1.51 Hz, 1H) 8.49 (d, J=1.63 Hz, 1H).

$^{13}$C NMR (101 MHz, METHANOL-d₄) δ ppm 27.08 (3C) 36.90 (1C) 80.45 (1C) 123.70 (1C) 131.63 (1C) 137.68 (1C) 147.09 (1C) 149.20 (1C) 156.26 (1C) 170.94 (1C).

HPLC-MS (m/z) [M+H]+ calcd 252.13, found 252.57.

Step 2: Synthesis of tert-butyl N-[[2-[1-[(3,5-ditert-butylphenyl)methyl]pyridin-1-ium-3-yl]acetyl]amino]carbamate bromide

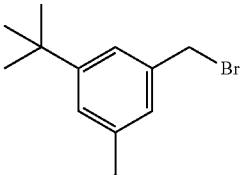

+

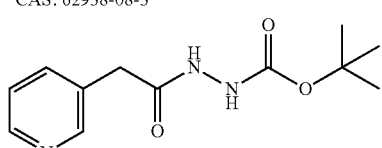

tert-butyl N-[[2-(3-pyridyl)acetyl]amino]carbamate

→ CH₃CN / 70° C.

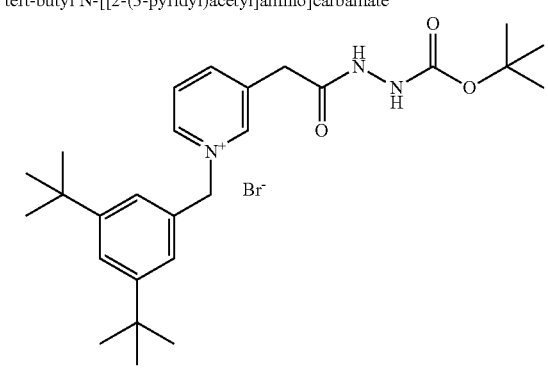

tert-butyl N-[[2-[1-[(3,5-ditert-butylphenyl)methyl] pyridin-1-ium-3-yl]acetyl]amino]carbamate; bromide Tert-butyl N-[[2-(3-pyridyl)acetyl]amino]carbamate (0.40 mmol) and 3,5-ditert-butylbenzyl bromide (0.48 mmol) were dissolved in dry CH₃CN. Then the solution was stirred at 70° C. overnight. The solvent was removed under vacuum and the crude purified by flash chromatography (gradient CH$_2$C$_2$→CH$_2$Cl$_2$/MeOH 80:20). 190 mg of the pure compound was obtained as a white solid (89% yield).

¹H NMR (400 MHz, METHANOL-d$_4$) δ ppm 1.33 (m, 18H) 1.45 (s, 9H) 3.87 (s, 2H) 5.80 (s, 2H) 7.38 (d, J=1.70 Hz, 2H) 7.53 (t, J=1.69 Hz, 1H) 8.06 (dd, J=7.80, 6.40 Hz, 1H) 8.53 (d, J=8.00 Hz, 1H) 8.95 (d, J=6.15 Hz, 1H) 9.15 (s, 1H).

¹³C NMR (101 MHz, METHANOL-d$_4$) δ ppm 27.10 (3C) 30.31 (6C) 34.48 (2C) 65.02 (1C) 80.69 (1C) 122.97 (2C) 123.72 (1C) 127.59 (1C) 132.39 (1C) 136.89 (1C) 142.47 (1C) 144.92 (1C) 146.69 (1C) 152.37 (2C) 156.45 (1C) 173.59 (1C).

HPLC-MS (m/z) [M]+ calcd 454.31, found 454.40.

Step 3: hydrazide formation: Synthesis of 2-[1-[(3,5-ditert-butylphenyl)methyl]pyridin-1-ium-3-yl]acetohydrazide bistrifluoroacetate

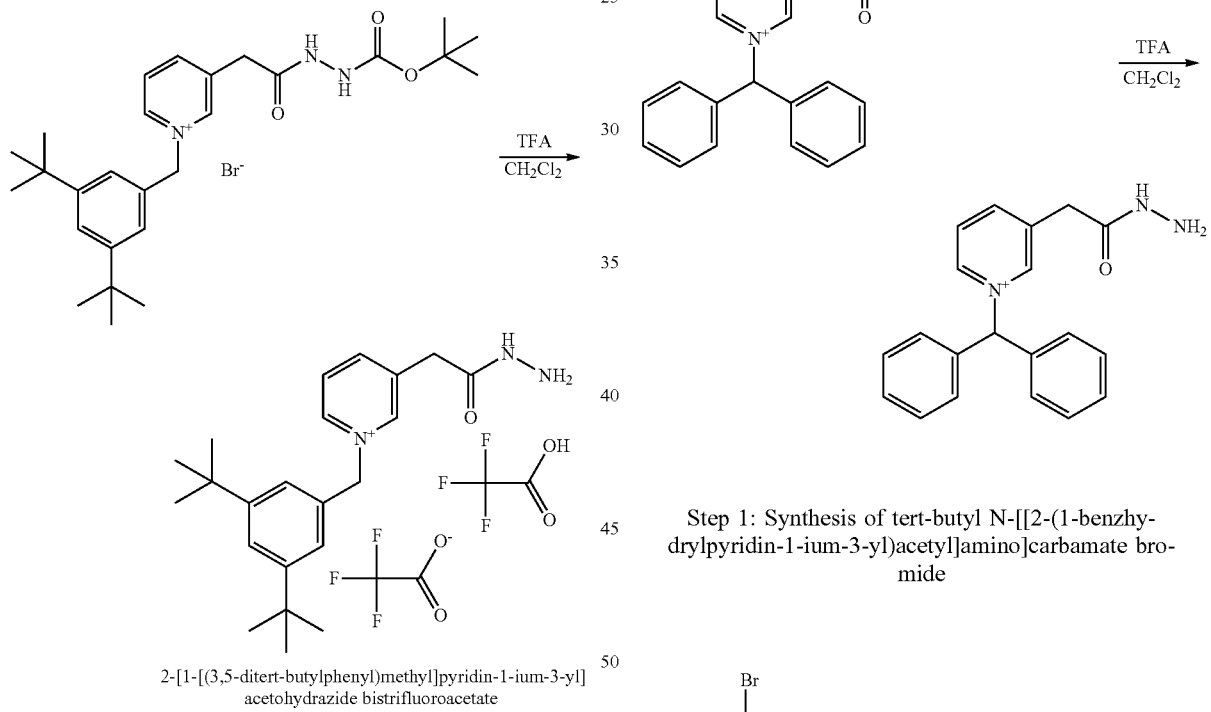

2-[1-[(3,5-ditert-butylphenyl)methyl]pyridin-1-ium-3-yl]acetohydrazide bistrifluoroacetate Tert-butyl N-[[2-[1-[(3,5-ditert-butylphenyl)methyl] pyridin-1-ium-3-yl]acetyl]amino]carbamate bromide (0.19 mmol) was treated with 50% TFA in CH₂Cl₂ (2 mL). The reaction mixture was stirred at room temperature for 1 h. The solvent was removed under vacuum and the crude suspended in water and lyophilized. 108 mg of the pure compound was obtained as a white solid, TFA salt (quantitative yield).

¹H NMR (400 MHz, METHANOL-d$_4$) δ ppm 1.30 (s, 18H) 3.97 (s, 2H) 5.81 (s, 2H) 7.37 (d, J=1.76 Hz, 2H) 7.53 (t, J=1.76 Hz, 1H) 8.08 (dd, J=7.91, 6.27 Hz, 1H) 8.53 (d, J=8.03 Hz, 1H) 8.97 (d, J=6.15 Hz, 1H) 9.15 (s, 1H).

¹³C NMR (101 MHz, METHANOL-d$_4$) δ ppm 30.29 (6C) 34.48 (2C) 35.56 (s, 1C) 65.01 (1C) 122.92 (2C) 123.73 (1C) 127.67 (1C) 132.39 (1C) 136.12 (1C) 142.79 (1C) 145.05 (1C) 146.81 (1C) 152.39 (2C) 167.95 (1C).

HPLC-MS (m/z) [M]+ calcd 354.25, found 354.43.

Scheme 5: Synthesis of Label 5

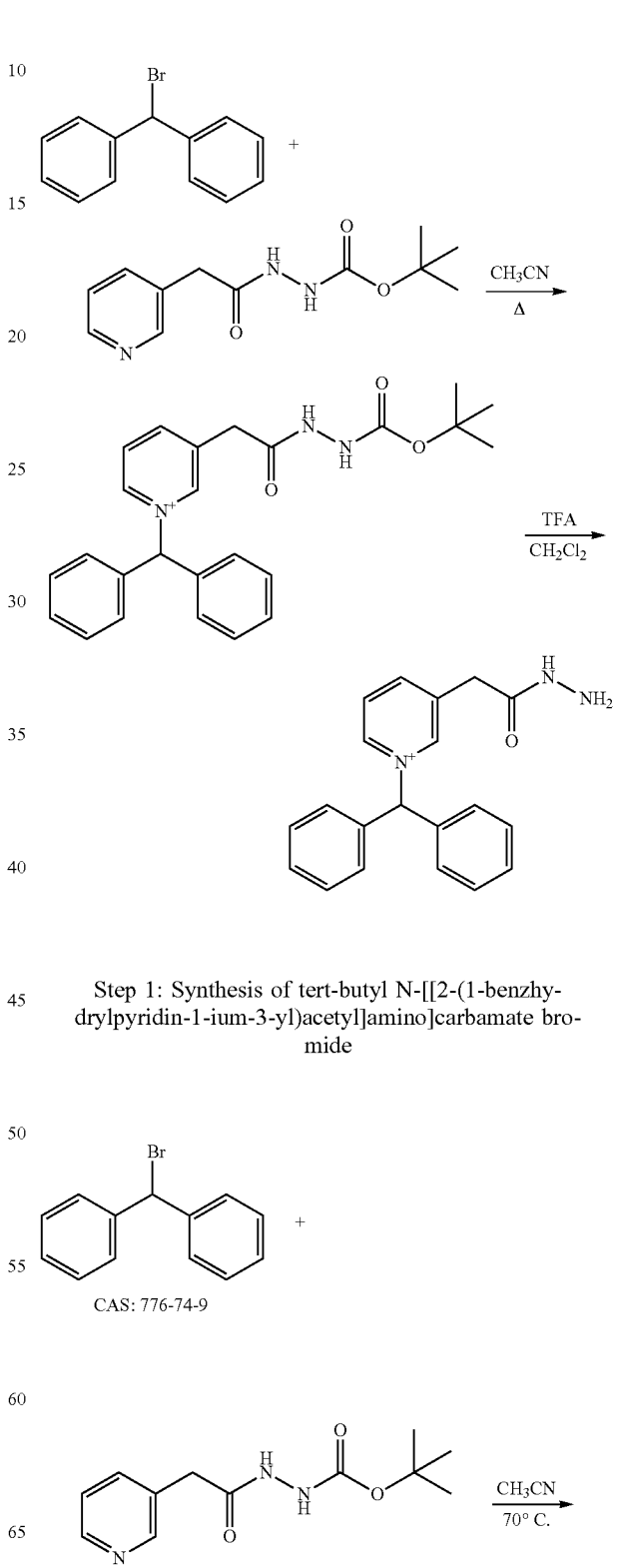

Step 1: Synthesis of tert-butyl N-[[2-(1-benzhydrylpyridin-1-ium-3-yl)acetyl]amino]carbamate bromide

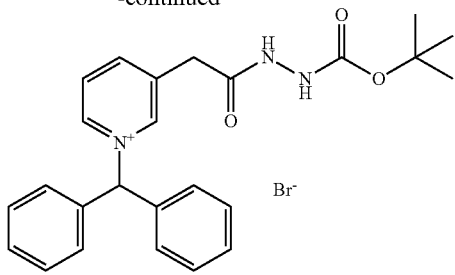

tert-butyl N-[[2-(1-benzhydrylpyridin-1-ium-3-yl)acetyl]amino]carbamate; bromide Tert-butyl N-[[2-(3-pyridyl)acetyl]amino]carbamate [synthesized as in example 4, step 1] (0.40 mmol) and Bromodiphenylmethane (0.48 mmol) were dissolved in dry CH$_3$CN. Then the solution was stirred at 70° C. overnight. The solvent was removed under vacuum and the crude purified by flash chromatography (gradient CH$_2$Cl$_2$→CH$_2$Cl$_2$/MeOH 80:20). 70 mg (44% yield) of the pure compound was obtained as a white solid.

$^1$H NMR (400 MHz, METHANOL-d$_4$) δ ppm 1.45 (s, 9H) 3.34 (s, 2H) 7.27-7.30 (m, 4H) 7.47-7.50 (m, 6H) 7.54 (s, 1H) 8.09 (dd, J=7.90, 6.30 Hz 1H) 8.58 (d, J=8.10 Hz, 1H) 8.84 (d, J=6.22 Hz, 1H) 8.97 (s, 1H).

$^{13}$C NMR (101 MHz, METHANOL-d$_4$) δ ppm 27.07 (3C) 77.79 (1C) 80.70 (1C) 127.73 (1C) 128.60 (4C) 129.28 (4C) 129.59 (2C) 135.37 (2C) 137.10 (1C) 142.68 (1C) 144.74 (1C) 147.50 (1C) 161.94 (s, 1C) 171.19 (1C).

HPLC-MS (m/z) [M]+ calcd 418.21, found 418.30.

Step 2: Synthesis of
2-(1-benzhydrylpyridin-1-ium-3-yl)acetohydrazide bistrifluoroacetate

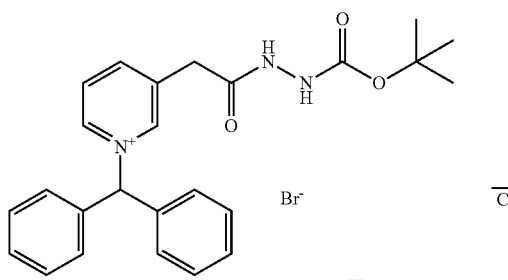

2-(1-benzhydrylpyridin-1-ium-3-yl)acetohydrazide bistrifluoroacetate

Tert-butyl N-[[2-(1-benzhydrylpyridin-1-ium-3-yl)acetyl]amino]carbamate bromide (0.19 mmol) was treated with 50% TFA in CH$_2$Cl$_2$ (2 mL). The reaction mixture was stirred at room temperature for 1 h. The solvent was removed under vacuum and the crude suspended in water and lyophilized. 24 mg of the pure compound (34% yield) was obtained as a oil.

HPLC method C-18 column:

0 min: 100% H$_2$O 0.1% TFA, 0% CH$_3$CN 0.1% TFA;

0-60 min: 40% H$_2$O 0.1% TFA; 60% CH$_3$CN 0.1% TFA;

60-65 min: 2% H$_2$O 0.1% TFA; 98% CH$_3$CN 0.1% TFA;

65-80 min: 2% H$_2$O 0.1% TFA; 98% CH$_3$CN 0.1% TFA.

$^1$H NMR (400 MHz, METHANOL-d$_4$) δ ppm 3.94 (s, 2H) 7.17-7.36 (m, 4H) 7.41-7.57 (m, 6H) 8.10 (dd, J=7.84, 6.46 Hz, 1H) 8.59 (d, J=7.91 Hz, 1H) 8.86 (d, J=6.02 Hz, 1H) 8.98 (s, 1H).

$^{13}$C NMR (101 MHz, METHANOL-d$_4$) δ ppm 38.99 (1C) 77.83 (1C) 127.80 (2C) 128.55 (4C) 129.31 (4C) 129.65 (1C) 135.32 (2C) 136.31 (1C) 142.91 (1C) 144.89 (1C) 147.63 (1C) 167.97 (1C).

HPLC-MS (m/z) [M]+ calcd 318.2, found 318.3.

Example 6: Synthesis of Label 6

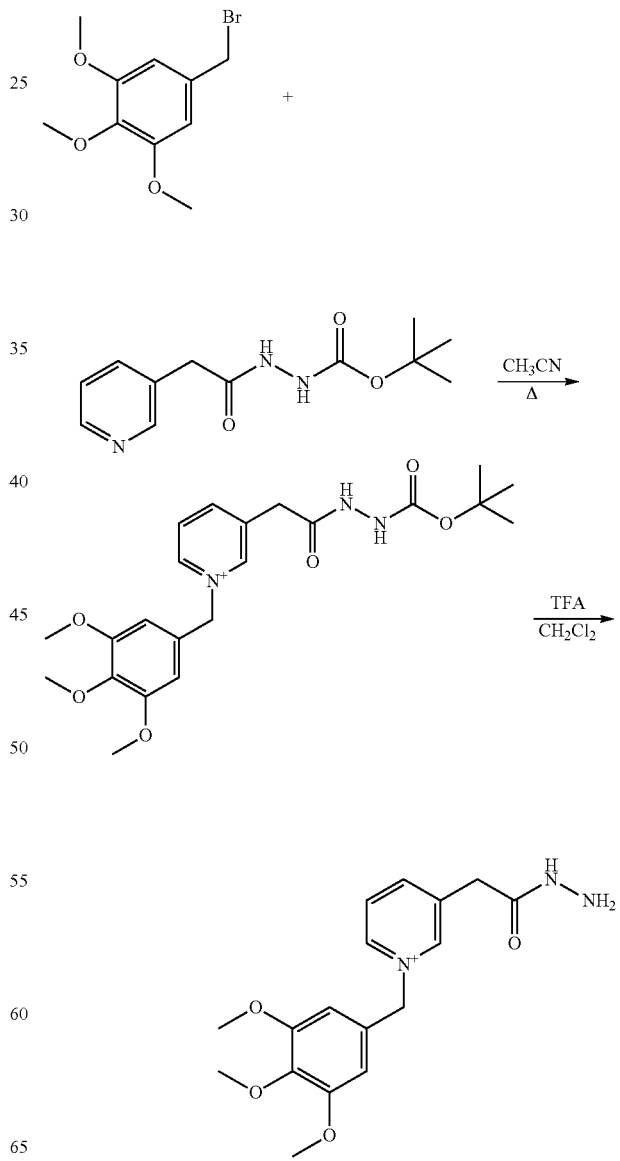

Step 1: Synthesis of tert-butyl N-[[2-[1-[3,4,5-trimethoxyphenyl)methyl]pyridin-1-ium-3-yl]acetyl]amino]carbamate bromide

Step 2: Synthesis of 2-[1-[(3,4,5-trimethoxyphenyl)methyl]pyridin-1-ium-3-yl]acetohydrazide bistrifluoroacetate

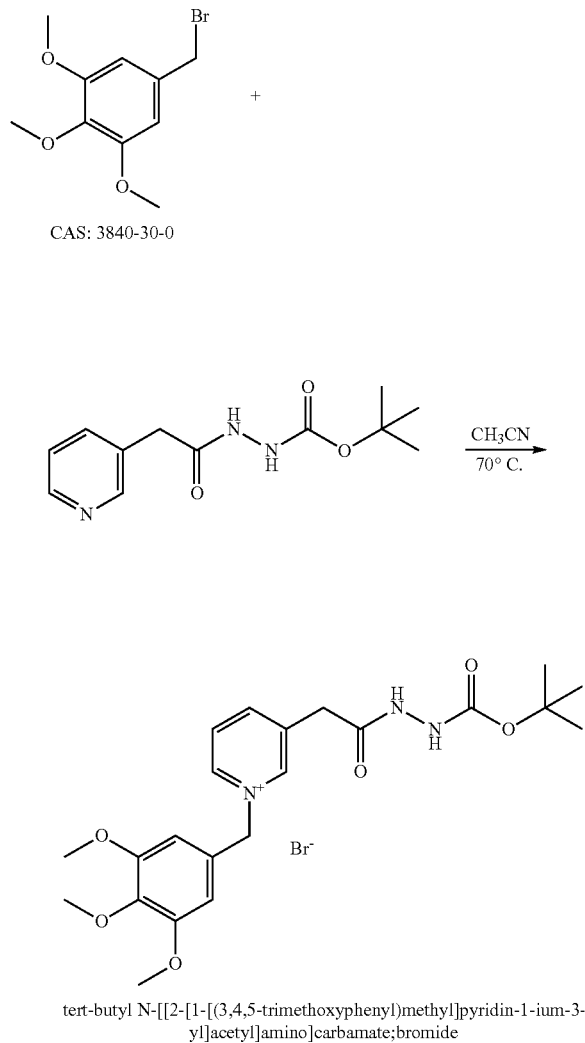

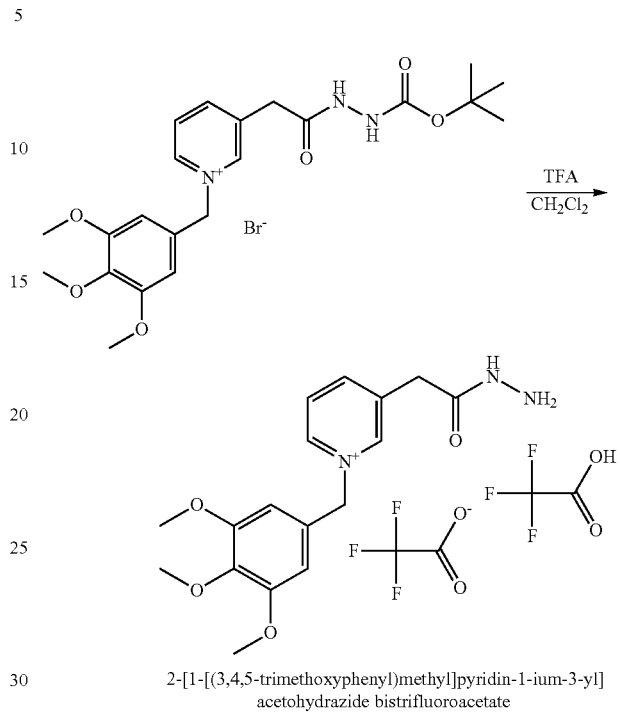

2-[1-[(3,4,5-trimethoxyphenyl)methyl]pyridin-1-ium-3-yl]acetohydrazide bistrifluoroacetate Tert-butyl N-[[2-[1-[(3,4,5-trimethoxyphenyl)methyl]pyridin-1-ium-3-yl]acetyl]amino]carbamate bromide (0.19 mmol) was treated with 50% TFA in CH$_2$Cl$_2$ (2 mL). The reaction mixture was stirred at room temperature for 1 h. The solvent was removed under vacuum and the crude suspended in water and lyophilized. 52 mg of a pure compound was obtained as a a brown oil (quantitative yield).

$^1$H NMR (400 MHz, METHANOL-d$_4$) δ ppm 3.74 (s, 3H) 3.85 (s, 6H) 4.00 (s, 2H) 5.77 (s, 2H) 6.91 (s, 2H) 8.07 (dd, J=7.91, 6.27 Hz, 1H) 8.54 (d, J=8.03 Hz, 1H) 9.02 (d, J=6.15 Hz, 1H) 9.20 (s, 1H).

$^{13}$C NMR (101 MHz, METHANOL-d$_4$) δ ppm 35.60 (1C) 55.50 (2C) 59.64 (1C) 64.53 (1C) 106.43 (2C) 127.64 (1C) 128.55 (1C) 136.03 (1C) 138.87 (1C) 142.82 (1C) 145.04 (1C) 146.81 (1C) 153.90 (2C) 168.06 (1C).

HPLC-MS (m/z) [M]+ calcd 332.2, found 332.4.

Tert-butyl N-[[2-(3-pyridyl)acetyl]amino]carbamate [synthesized as in example 4, step 1] (0.40 mmol) and 3,4,5-Trimethoxybenzyl bromide (0.48 mmol) were dissolved in dry CH$_3$CN. Then the solution was stirred at 70° C. overnight. The solvent was removed under vacuum and the crude purified by flash chromatography (gradient CH$_2$Cl$_2$→CH$_2$Cl$_2$/MeOH 80:20). 55 mg, 34% yield, of the pure compound was obtained as a brownish oil.

$^1$H NMR (400 MHz, METHANOL-d$_4$) δ ppm 1.46 (s, 9H) 3.74 (s, 3H) 3.84 (s, 6H) 5.74 (s, 2H) 6.89 (s, 2H) 8.05 (dd, J=7.78, 6.27 Hz, 1H) 8.52 (d, J=8.16 Hz, 1H) 8.98 (d, J=5.90 Hz, 1H) 9.15 (s, 1H).

$^{13}$C NMR (101 MHz, METHANOL-d$_4$) δ ppm 27.07 (3C) 36.03 (1C) 55.46 (2C) 59.62 (1C) 64.57 (1C) 80.69 (1C) 106.36 (2C) 127.59 (1C) 128.51 (1C) 136.87 (1C) 138.92 (1C) 142.53 (1C) 144.89 (s, 1C) 146.70 (s, 1C) 153.93 (2C) 166.93 (1C) 168.98 (1C).

HPLC-MS (m/z) [M]+ calcd 432.21, found 432.29.

Example 7: Synthesis of Label 7: Synthesis of 4-[1-[(2-methoxyphenyl)methyl]pyridin-1-ium-4-yl]-1,2,4-triazolidine-3,5-dione trifluoroacetate

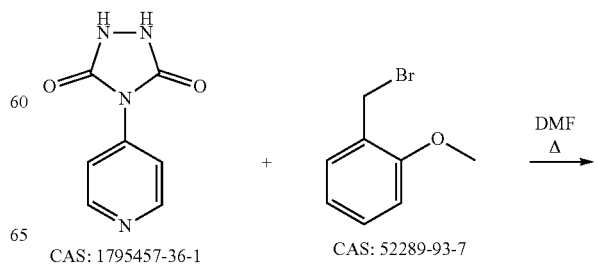

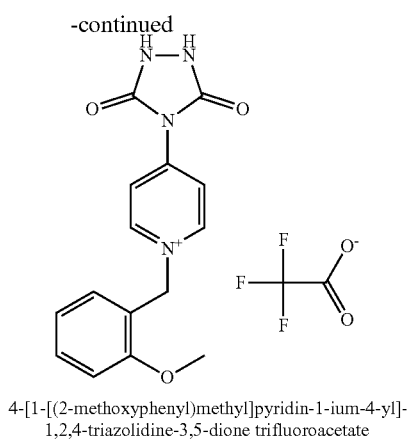

4-[1-[(2-methoxyphenyl)methyl]pyridin-1-ium-4-yl]-1,2,4-triazolidine-3,5-dione trifluoroacetate 4-(Pyridin-4-yl)-1,2,4-triazolidine-3,5-dione (0.28 mmol) and 1-(Bromomethyl)-2-methoxybenzene (0.29 mmol) were dissolved in 1 mL of dry DMF. The reaction mixture was stirred overnight at 70° C. The solvent was removed under vacuum and residue was purified by preparative HPLC. The pure fractions were collected and concentrated under vacuum to give 71 mg (61% yield) of the desired product as light yellow solid.

HPLC method C-18 column:
0 min: 100% $H_2O$ 0.1% TFA, 0% $CH_3CN$ 0.1% TFA;
0-60 min: 40% $H_2O$ 0.1% TFA, 60% $CH_3CN$ 0.1% TFA;
60-64 min: 2% $H_2O$ 0.1% TFA; 98% $CH_3CN$ 0.1% TFA;
64-74 min: 2% $H_2O$ 0.1% TFA; 98% $CH_3CN$ 0.1% TFA;
74-79 min: 60% $H_2O$ 0.1% TFA; 40% $CH_3CN$ 0.1% TFA;
79-90 min: 60% $H_2O$ 0.1% TFA, 40% $CH_3CN$ 0.1% TFA.

$^1H$ NMR (400 MHz, METHANOL-$d_4$) δ ppm 3.83 (s, 3H) 5.70 (s, 2H) 7.04-7.10 (m, 2H) 7.44-7.51 (m, 1H) 7.54 (dd, 0.1=7.84, 1.69 Hz, 1H) 8.73-8.83 (m, 2H) 8.92-8.99 (m, 2H).

HPLC-MS (m/z) [M]$^-$ calcd 299.11, found 299.33.
Label 9 can be synthesized in the same manner.

Example 8: Synthesis of Label 8: Synthesis of 4-(1-methylpyridin-1-ium-4-yl)-iodide

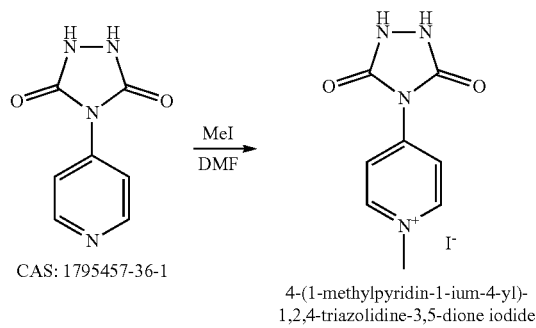

CAS: 1795457-36-1

4-(1-methylpyridin-1-ium-4-yl)-1,2,4-triazolidine-3,5-dione iodide 4-(Pyridin-4-yl)-4,2,4-triazolidine-3,5-dione (0.34 mmol) was dissolved in dry DMF. Then MeI (0.40 mmol) was added and the solution stirred overnight at room temperature. The solvent was removed under vacuum obtaining a yellow solid without additional purification (quantitative yield).

$^1H$ NMR (400 MHz, DMSO-$d_6$) δ ppm 4.27 (s, 5H) 8.47-8.57 (m, 4H) 8.90-8.98 (m, 4H) 11.37 (br s, 4H).
HPLC-MS (m/z) [M]$^-$ calcd 193.07, found 193.27.

Example 9: Synthesis of Label 10: Synthesis of 2-fluoro-1-[(2-methoxyphenyl)methyl]-N,N-dimethyl-pyridin-1-ium-1-amine bromide

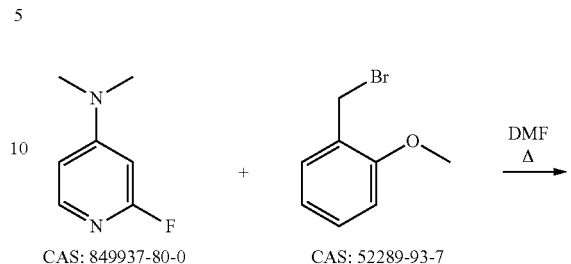

CAS: 849937-80-0   CAS: 52289-93-7

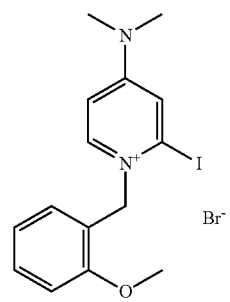

2-fluoro-1-[(2-methoxyphenyl)methyl]-N,N-dimethyl-pyridin-1-ium-4-amine bromide

2-Fluoro-N,N-dimethylpyridin-4-amine (0.35 mmol) and 1-(Bromomethyl)-2-methoxybenzene (0.39 mmol) were dissolved in 1 ml of dry DMF. The reaction mixture was stirred overnight at 70° C. The solvent was removed under vacuum and residue was purified by silica gel chromatography (eluents $CH_2Cl_2$/MeOH 100:0→95:5). The pure fractions were collected and concentrated under vacuum to give 100 mg (82% yield) of the desired product as colourless oil.

$^1H$ NMR (400 MHz, CHLOROFORM-d) δ ppm 3.24 (s, 3H) 3.35 (s, 3H) 3.85 (s, 3H) 5.38 (d, J=1.76 Hz, 2H) 6.47 (dd, J=8.66, 2.89 Hz, 1H) 6.88 (d, J=7.78 Hz, 1H) 6.97 (td, J=7.47, 1.00 Hz, 1H) 7.23 (d, J=2.89 Hz, 1H) 7.33-7.40 (m, 1H) 7.44 (dt, J=7.40, 1.51 Hz, 1H) 8.44 (dd, J=7.78, 6.15 Hz, 1H).

$^{19}F$ NMR (376 MHz, CHLOROFORM-d) δ ppm −87.92 (s, 1F).

HPLC-MS (m/z) [M]$^+$ calcd 261.14, found 261.36.

Example 10: Synthesis of Label 11: Synthesis of 2-fluoro-N,N-dimethyl-1-[(3,4,5-trimethoxyphenyl)methyl]pyridin-1-ium-4-amine bromide

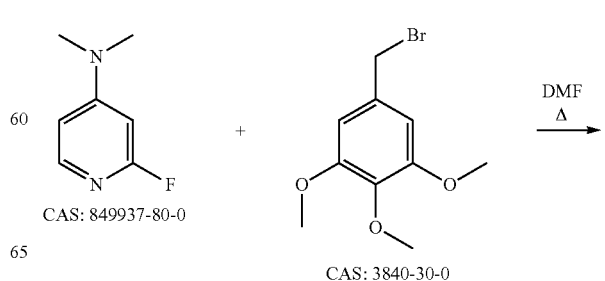

CAS: 849937-80-0   CAS: 3840-30-0

-continued

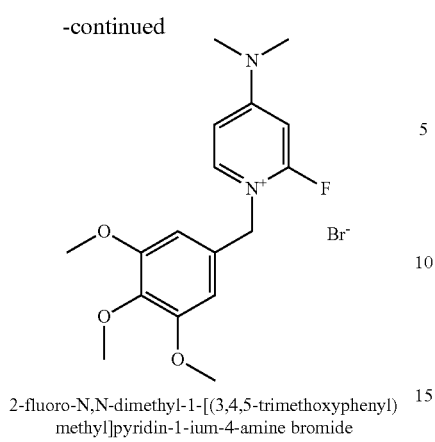

2-fluoro-N,N-dimethyl-1-[(3,4,5-trimethoxyphenyl)methyl]pyridin-1-ium-4-amine bromide 2-Fluoro-N,N-dimethylpyridin-4-amine (0.35 mmol) and 3,4,5-Trimethoxybenzyl bromide (0.39 mmol) were dissolved in 1 ml of dry DMF. The reaction mixture was stirred overnight at 70° C. The solvent was removed under vacuum and residue was purified by silica gel chromatography (eluents $CH_2Cl_2$/MeOH 100:0→95:5). The pure fractions were collected and concentrated under vacuum to give 73 mg (51% yield) of the desired product as brown oil.

$^1$H NMR (400 MHz, CHLOROFORM-d) δ ppm 3.22 (s, 3H) 3.28 (s, 3H) 3.46 (s, 3H) 3.80 (s, 3H) 3.88 (s, 3H) 5.52 (d, J=1.76 Hz, 2H) 6.44 (dd, J=8.53, 2.76 Hz, 1H) 6.85 (s, 2H) 6.91-7.07 (m, 1H) 9.30 (br t, J=6.90 Hz, 1H).

$^1$H NMR (376 MHz, CHLOROFORM-d) δ ppm −88.40 (s, 1F).

HPLC-MS (m/z) [M]$^+$ calcd 321.16, found 321.31.

Example 11: General Procedure of Synthesis

Example 11.1: Labels 1 to 3

Labels 1 to 3 are synthesized in in two steps: Pyridine alkylation and hydrazide formation.

Step 1. General Protocol for Pyridine Alkylation:

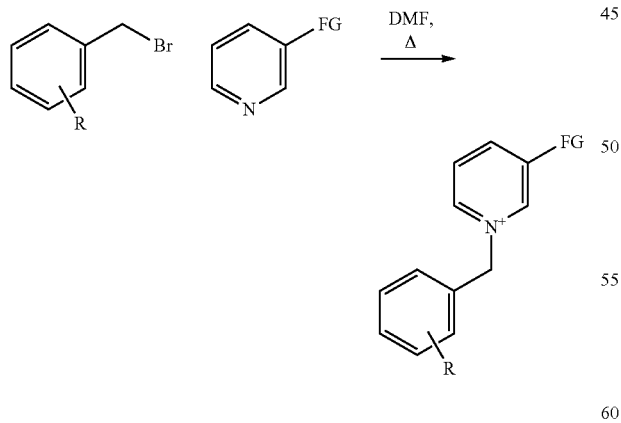

Pyridine derivative (0.87 mmol) and Benzyl Bromide derivative (1.14 mmol) were dissolved in 3 mL DMF. The reaction mixture was stirred at 115° C. for 2 h. DMF was removed in vacuum and residue was purified by preparative HPLC. The pure fractions were collected and lyophilized to give the products (85-96% yield) of coloured oil. FG means in this context functional group.

Step 2: General Protocol for Hydrazide Formation:

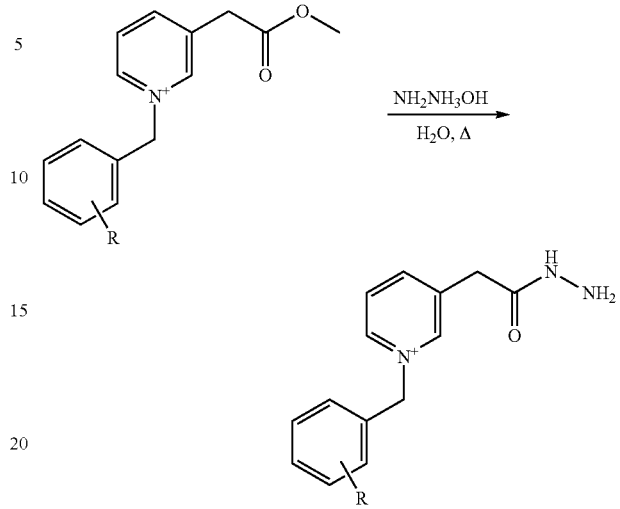

Pyridine-Methyl-Acetate derivative (0.74 mmol) was dissolved in 2 mL water or MeOH. Hydrazine monohydrate (0.74 mmol) was added and reaction mixture was stirred between r.t or 100° C. for between 30 min until 2 h. The reaction mixture was purified by preparative HPLC. The pure fractions were collected and lyophilised to give the products (46-79% yield).

Example 11.2: Labels 4 to 6

Labels 4 to 6 comprises the tert-butyl N-[[2-(3-pyridyl)acetyl]amino]carbamate alkylation and Boc deprotection. Tert-butyloxycarbonyl protecting group or tert-butoxycarbonyl protecting group can be abbreviated as Boc.

The general protocol for tert-butyl N-[[2-(3-pyridyl)acetyl]amino]carbamate alkylation is as follows:

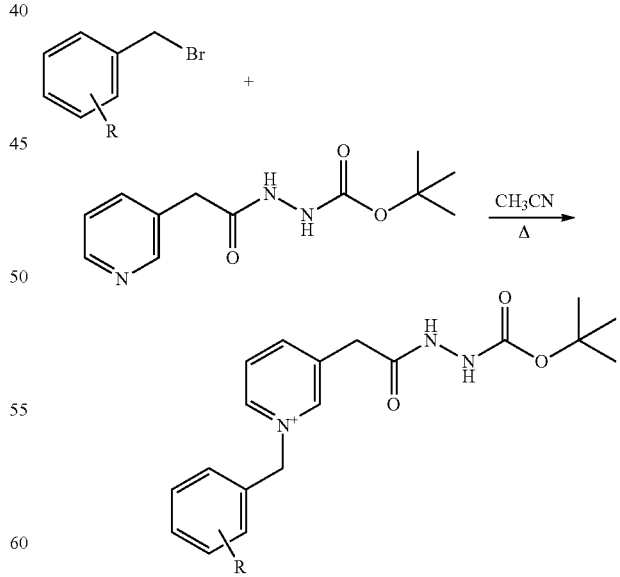

Tert-butyl N-[[2-(3-pyridyl)acetyl]amino]carbamate (0.40 mmol) and benzyl bromide derivative (0.48 mmol) were dissolved in dry $CH_3CN$. Then the solution was stirred at 70° C. overnight. The solvent was removed under vacuum and the crude purified by flash chromatography (gradient CH$_2$Cl$_2$→CH$_2$Cl$_2$/MeOH 80:20). Pure compound was obtained as a white solid (34-89% yield).

The general protocol for Boc deprotection is as follows:

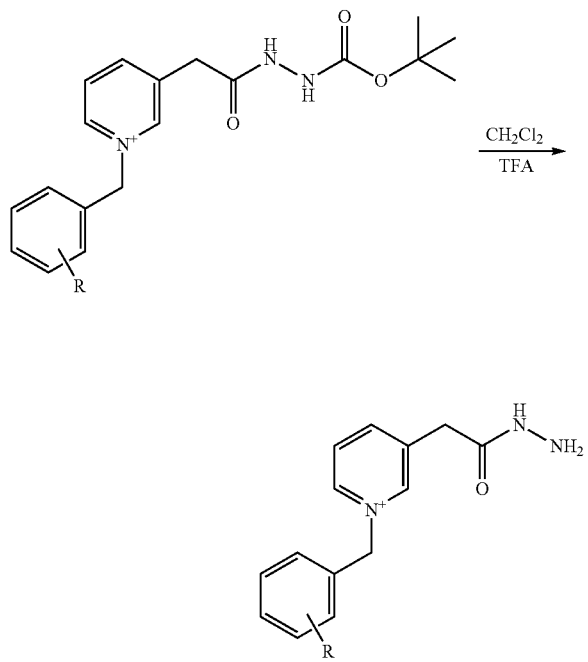

Boc-protected pyridinium salt (0.19 mmol) was treated with 50% TFA in CH$_2$Cl$_2$ (2 mL). The reaction mixture was stirred at r.t. for 1 h. The solvent was removed under vacuum and the crude suspended in water and lyophilized. Pure compound was obtained as a white solid, TFA salt (quantitative yield).

Example 11.3: Labels 7 and 9

Labels 7 and 9 are pyridine-urazole derivatives. The general protocol for pyridine-urazole alkylation is as follows:

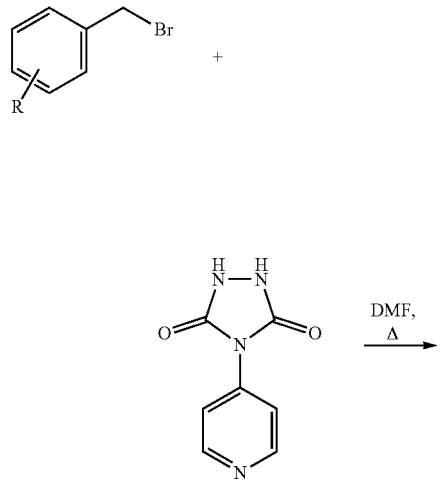

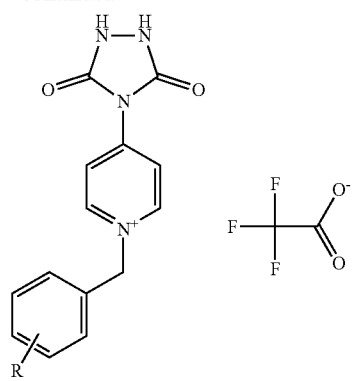

4-(Pyridin-4-yl)-1,2,4-triazolidine-3,5-dione (0.28 mmol) and benzyl bromide derivative (0.29 mmol) were dissolved in 1 mL of dry DMF. The reaction mixture was stirred overnight at 70° C. The solvent was removed under vacuum and residue was purified by preparative HPLC. The pure fractions were collected and concentrated under vacuum to give the products (61% yield) as solids.

Example 11.4: Labels 10 and 11

Labels 10 and 11 are synthesized in the following general step: General protocol for fluoro pyridine alkylation:

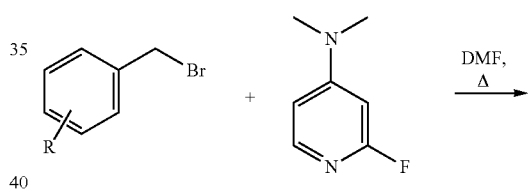

2-Fluoro-N,N-dimethylpyridin-4-amine (0.35 mmol) and benzyl bromide derivative (0.39 mmol) were dissolved in 1 mL of dry DMF. The reaction mixture was stirred overnight at 70° C. The solvent was removed under vacuum and residue was purified by silica gel chromatography (eluents CH$_2$Cl$_2$/MeOH 100:0→95:5). The pure fractions were collected and concentrated under vacuum to give the products (51-82% yield) as oils.

Example 12: General Protocol for Reaction of Testosterone with Hydrazide Derivative

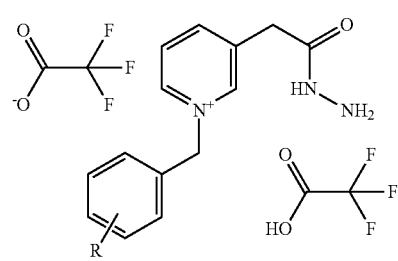

+

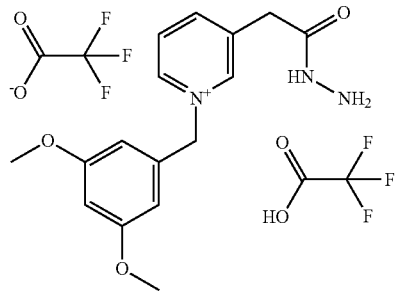

MeOH →

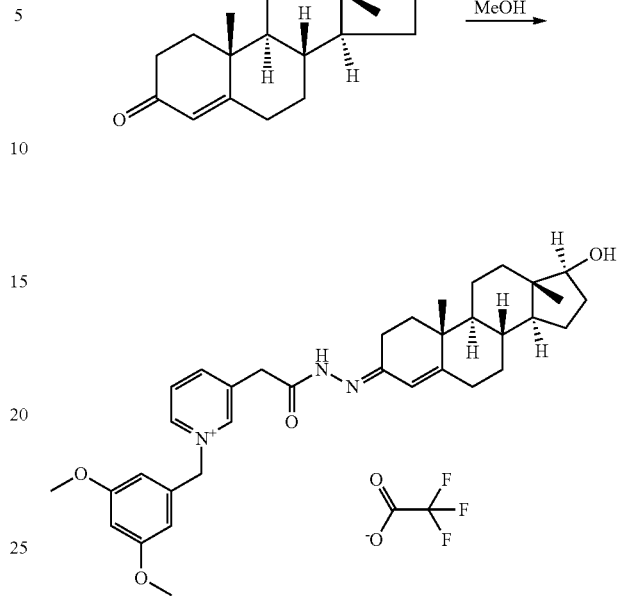

Hydrazide derivative (0.072 mmol) was dissolved in dry MeOH (1 mL) and testosterone (0.052 mmol) was added. The solution stirred at room temperature or 50° C. overnight. The solvent was removed in vacuo and the crude mixture was subjected to purification via preparative HPLC yielding the desired product as a white solid.

Example 12.1: Preparation of Label 3-Testosterone Derivative and its Analysis Via MS HPLC-MS (m/z) [M]$^+$ calcd 572.35, found 572.39.

Example 13: General Protocol for In Situ Activation of Urazole to Labels Comprising TAD and Reaction with Vitamin D

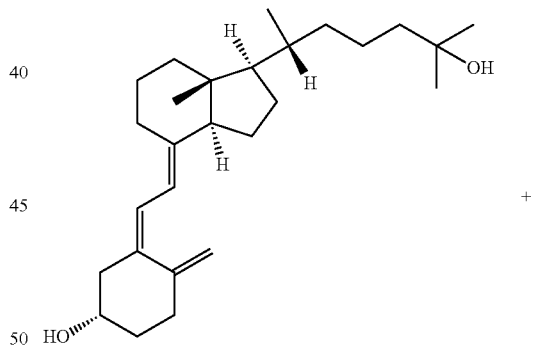

+

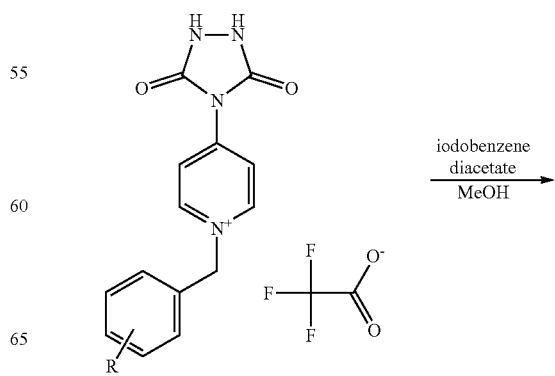

iodobenzene diacetate / MeOH →

75

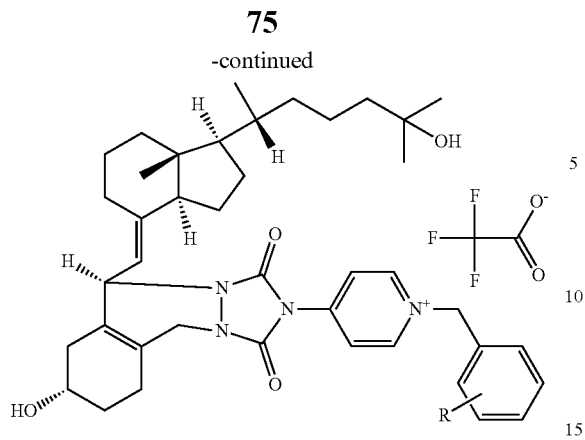

25-Hydroxyvitamin D monohydrate (0.024 mmol) and urazole derivative (0.029 mmol) were dissolved in MeOH (500 μL). A solution of iodobenzene diacetate (0.033 mmol) in MeOH was added to the first solution. The reaction mixture was stirred at r.t. for 15 min. Full conversion of vitamin D to the corresponding product was observed. The solvent was removed under vacuum and the residue was purified by preparative HPLC. Pure products were obtained as white solids.

Example 13.1: Preparation of Label 7-Vitamin D Derivative and its Analysis Via MS

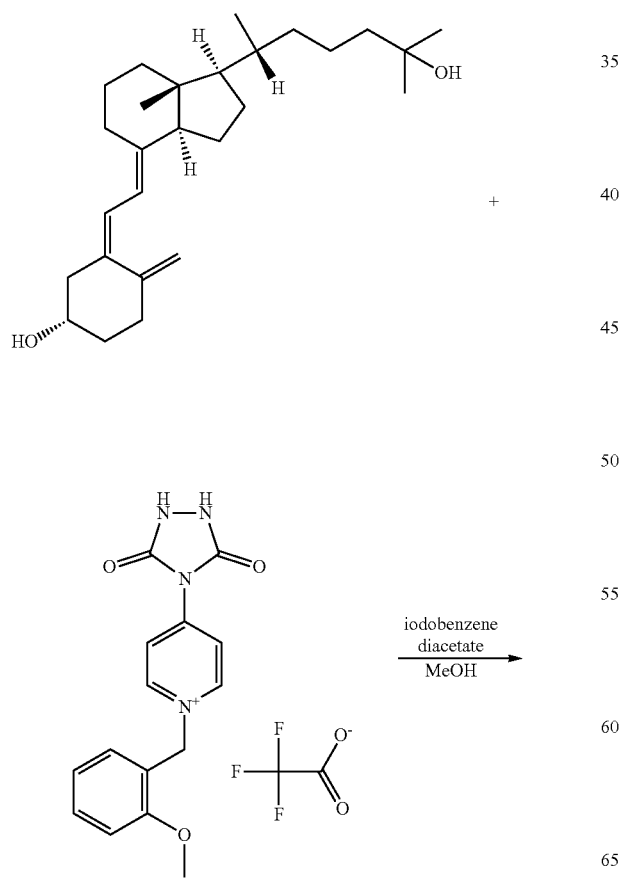

76

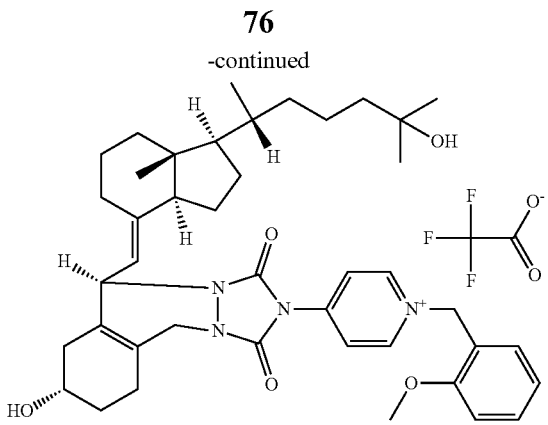

HPLC method C-18 column:

0 min: 100H $H_2O$ 0.1% TFA, 0% $CH_3CN$ 0.1% TFA;
0-20 min: 5% $H_2O$ 0.1% TFA, 95% $CH_3CN$ 0.1% TFA;
20-40 min: 5% $H_2O$ 0.1% TFA; 95% $CH_3CN$ 0.1% TFA;
40-45 min: 2% $H_2O$ 0.1% TFA; 98% $CH_3CN$ 0.1% TFA;
45-50 min: 2% $H_2O$ 0.1% TFA; 98% $CH_3CN$ 0.1% TFA;
50-55 min: 60% $H_2O$ 0.1% TFA; 40% $CH_3CN$ 0.1% TFA;
55-65 min: 60% $H_2O$ 0.1% TFA; 40% $CH_3CN$ 0.1% TFA.

$^1$H NMR (400 MHz, METHANOL-$d_4$) δ ppm 0.43 (s, 2H) 0.59 (s, 1H) 0.87-0.91 (m, 4H) 1.12-1.20 (m, 6H) 1.25-1.48 (m, 10H) 1.56-2.29 (m, 12H) 2.37-2.46 (m, 1H) 2.87-2.95 (m, 1H) 3.82 (s, 3H) 3.87-4.05 (m, 2H) 4.14-4.25 (m, 1H) 4.74-4.82 (m, 1H) 5.06-5.16 (m, 1H) 5.70 (s, 2H) 7.00-7.11 (m, 2H) 7.43-7.51 (m, 1H) 7.54 (dt, J=7.72, 1.85 Hz, 1H) 8.69-8.79 (m, 2H) 8.91-9.04 (m, 2H).

HPLC-MS (m/z) [M]$^+$ calcd 697.43, found 697.56.

Example 13.2: Preparation of Label 8-Vitamin D Derivative and its Analysis Via MS

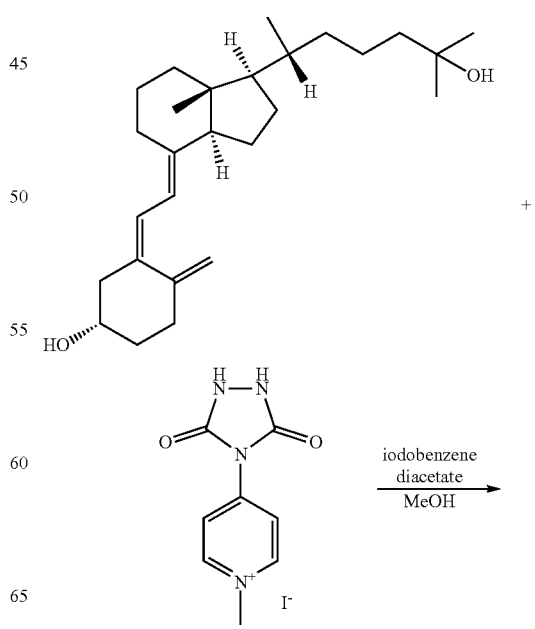

-continued

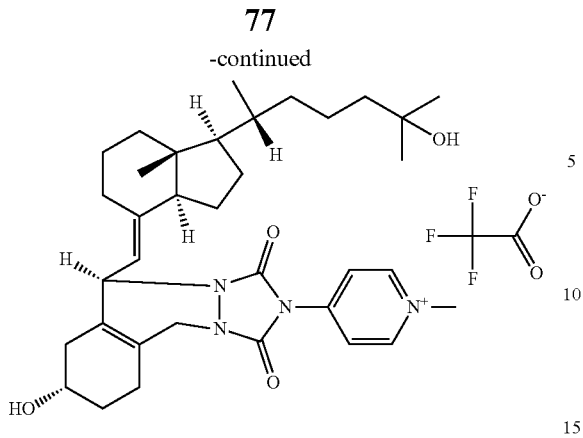

HPLC method C-18 column:
0 min: 100% $H_2O$ 0.1% TFA, 0% $CH_3CN$ 0.1% TFA;
0-20 min: 5% $H_2O$ 0.1% TFA, 95% $CH_3CN$ 0.1% TFA;
20-40 min: 5% $H_2O$ 0.1% TFA; 95% $CH_3CN$ 0.1% TFA;
40-45 min: 2% $H_2O$ 0.1% TFA; 98% $CH_3CN$ 0.1% TFA;
45-50 min: 2% $H_2O$ 0.1% TFA; 98% $CH_3CN$ 0.1% TFA;
50-55 min: 60% $H_2O$ 0.1% TFA; 40% $CH_3CN$ 0.1% TFA,
55-65 min: 60% $H_2O$ 0.1% TFA; 40% $CH_3CN$ 0.1% TFA.

$^1$H NMR (400 MHz, METHANOL-$d_4$) δ ppm 0.45 (s, 2H) 0.60 (s, 1H) 0.87-1.02 (m, 4H) 1.14 (s, 3H) 1.15 (s, 3H) 1.25-1.50 (m, 10H) 1.61-2.29 (m, 12H) 2.37-2.46 (m, 1H) 2.89-2.87 (m, 1H) 3.87-4.05 (m, 2H) 4.17-4.26 (m, 1H) 4.34 (s, 3H) 4.76-4.82 (m, 1H) 5.10-5.17 (m, 1H) 8.72-8.81 (m, 2H) 8.88 (t, J=6.74 Hz, 2H).

HPLC-MS (m/z) $[M]^+$ calcd 591.39, found 591.50.

Example 14: General Protocol for Reaction of Estradiol with Fluoro-Pyridine Derivative

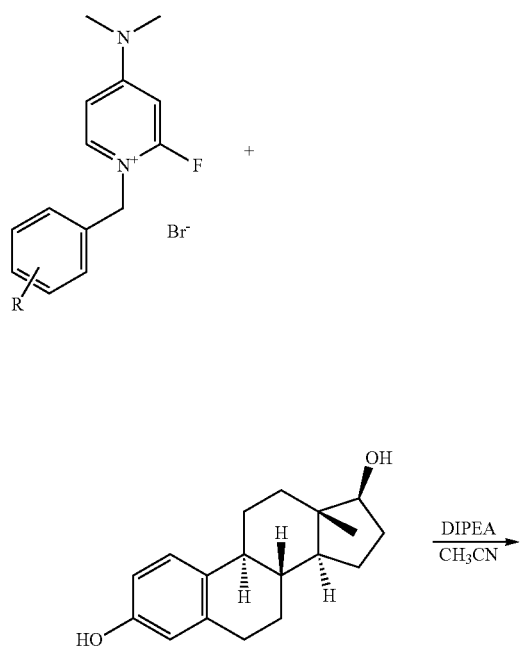

-continued

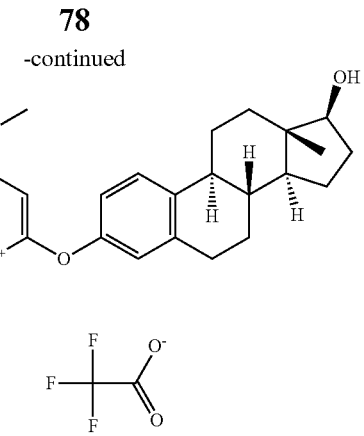

Estradiol (0.09 mmol) and fluoro pyridine derivative (0.11 mmol) were dissolved in $CH_3CN$ (1 mL). Then DIPEA (0.14 mmol) was added and the reaction mixture stirred at r.t. for 30 min. The solvent was removed under vacuum and the residue was purified by preparative HPLC. The pure fractions were collected and lyophilized to obtain the product as a solid (21-45% yield).

Example 14.1: Preparation of Label 10-Estradiol Derivative and its Analysis Via MS

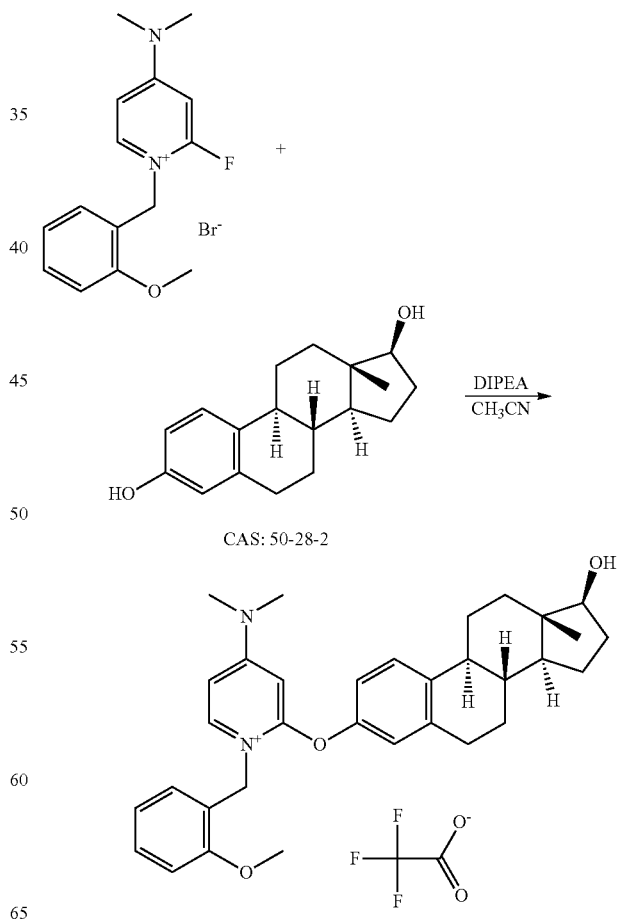

HPLC method C-18 column:
0 min: 90% H₂O 0.1% TFA, 10% CH₃CN 0.1% TFA;
0-60 min: 30% H₂O 0.1% TFA, 70% CH₃CN 0.1% TFA;
60-64 min: 2% H₂O 0.1% TFA; 98% CH₃CN 0.1% TFA;
64-74 min: 2% H₂O 0.1% TFA; 98% CH₃CN 0.1% TFA;
74-79 min: 60% H₂O 0.1% TFA; 40% CH₃CN 0.1% TFA;
79-90 min: 60% H₂O 0.1% TFA; 40% CH₃CN 0.1% TFA.
$^1$H NMR (400 MHz, METHANOL-$d_4$) δ ppm 0.78 (s, 3H) 1.11-1.60 (in, 7H) 1.63-1.78 (m, 1H) 1.84-2.11 (m, 3H) 2.19-2.29 (m, 1H) 2.36 (dq, J=13.40, 3.52 Hz, 1H) 2.76-2.87 (m, 2H) 2.92 (br s, 3H) 3.19 (br s, 3H) 3.66 (t, J=8.60 Hz, 1H) 3.85 (s, 3H) 5.40 (s, 2H) 5.80 (d, J=2.76 Hz, 1H) 6.73-6.79 (m, 2H) 6.81 (dd, J=8.47, 2.70 Hz, 1H) 6.91-7.00 (m, 1H) 7.05 (d, J=8.16 Hz, 1H) 7.30 (dd, J=7.47, 1.57 Hz, 1H) 7.41 (br d, J=8.53 Hz, 2H) 8.09 (d, J=7.78 Hz, 1H).
HPLC-MS (m/z) [M]+ calcd 513.31, found 513.41.

Example 14.2: Preparation of Label 11-Estradiol Derivative and its Analysis Via MS

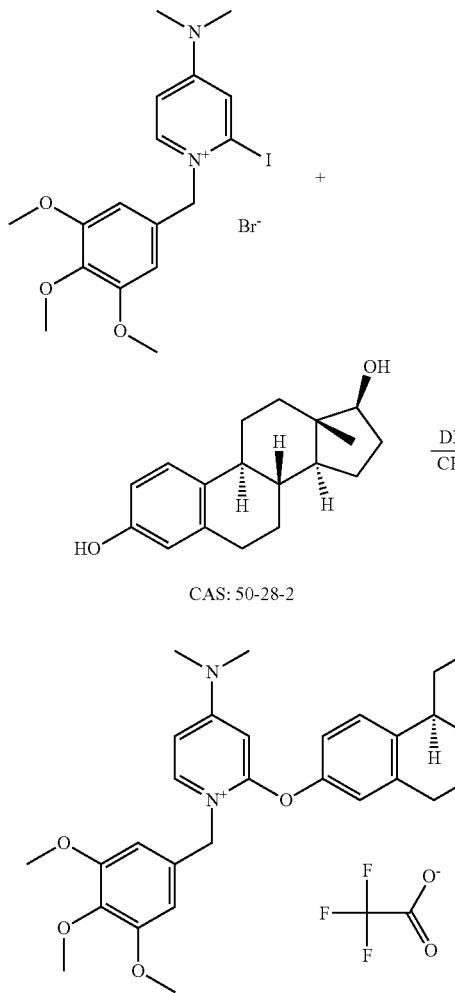

HPLC method C-18 column:
0 min: 100% H₂O 0.1% TFA, 0% CH₃CN 0.1% TFA;
0-60 min: 40% H₂O 0.1% TFA, 60% CH₃CN 0.1% TFA;
60-64 min: 2% H₂O 0.1% TFA; 98% CH₃CN 0.1% TFA;
64-74 min: 2% H₂O 0.1% TFA; 98% CH₃CN 0.1% TFA;
74-79 min: 60% H₂O 0.1% TFA; 40% CH₃CN 0.1% TFA;
79-90 min: 60% H₂O 0.1% TFA; 40% CH₃CN 0.1% TFA.

$^1$H NMR (400 MHz, METHANOL-$d_4$) δ ppm 0.78 (s, 3H) 1.12-1.59 (m, 7H) 1.64-1.79 (m, 1H) 1.82-2.10 (m, 3H) 2.18-2.30 (m, 1H) 2.31-2.42 (m, 1H) 2.81-2.89 (m, 2H) 2.95 (br s, 3H) 3.21 (br s, 3H) 3.66 (t, J=8.66 Hz, 1H) 3.74 (s, 3H) 3.76 (s, 6H) 5.37 (s, 2H) 5.88 (d, J=2.76 Hz, 1H) 6.70 (s, 2H) 6.79 (d, J=2.76 Hz, 1H) 6.84 (dd, J=7.72, 2.82 Hz, 1H) 6.88 (dd, J=8.60, 2.70 Hz, 1H) 7.43 (d, J=8.66 Hz, 1H) 8.18 (d, J=7.78 Hz, 1H).
HPLC-MS (m/z) [M]+ calcd 573.33, found 573.49.

Example 14.3: Preparation of Label 12-Estradiol Derivative and its Analysis Via MS

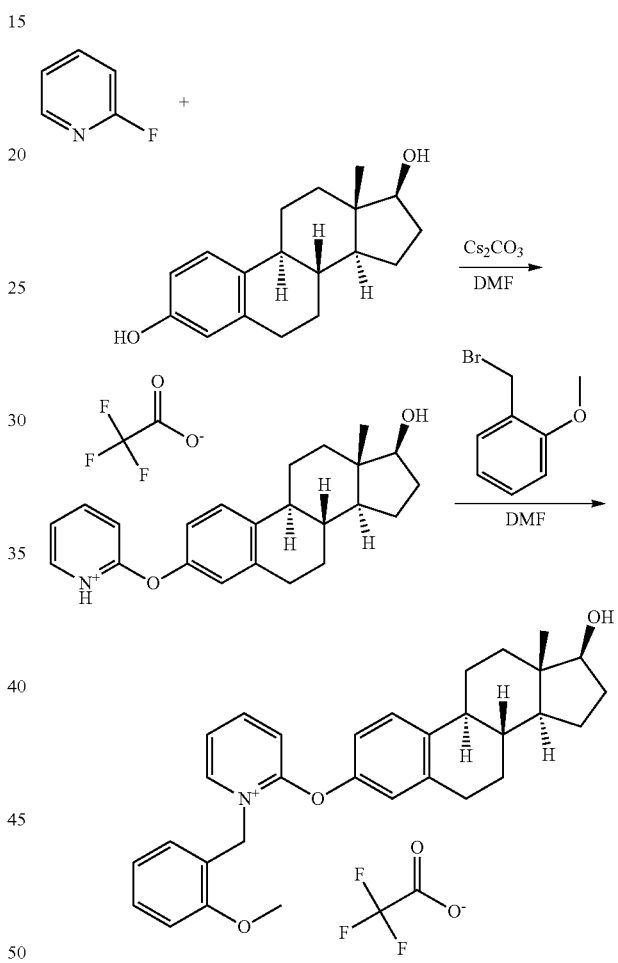

Estradiol (0.50 mmol), fluoro pyridine (0.52 mmol) and Cs₂CO₃ (0.59 mmol) were dissolved in dry DMF (1 mL). The reaction mixture stirred at 70° C. for 7 d. The solvent was removed under vacuum and the residue was purified by preparative HPLC. The pure fractions were collected and lyophilized to obtain the 81 mg (35% yield) of product as a colorless solid. The obtained product (0.09 mmol) was further reacted with benzyl bromide derivative (0.11 mmol) in dry (I mL) at 70° C. for 2 d. The solvent was removed under vacuum and the residue was purified by preparative HPLC. The pure fractions were collected and lyophilized to obtain the 18 mg (36% yield) of product as a colorless solid.
First Purification HPLC method C-18 column:
0 min: 100% H₂O 0.1% TFA, 0% CH₃CN 0.1% TFA;
0-60 min: 20% H₂O 0.1% TFA, 80% CH₃CN 0.1% TFA;

60-64 min: 2% H$_2$O 0.1% TFA; 98% CH$_3$CN 0.1% TFA;
64-80 min: 2% H$_2$O 0.1% TFA; 98% CH$_3$CN 0.1% TFA;
80-83 min: 60% H$_2$O 0.1% TFA; 40% CH$_3$CN 0.1% TFA;
83-89 min: 60% H$_2$O 0.1% TFA; 40% CH$_3$CN 0.1% TFA;
89-90 min: 60% H$_2$O 0.1% TFA; 40% CH$_3$CN 0.1% TFA.
HPLC-MS (m/z) [M+H]$^+$ calcd 350.47, found 350.50.
Second Purification HPLC method C-18 column:
0 min: 100% H$_2$O 0.1% TFA, 0% CH$_3$CN 0.1% TFA;
0-60 min: 2% H$_2$O 0.1% TFA, 98% CH$_3$CN 0.1% TFA;
60-64 min: 2% H$_2$O 0.1% TFA; 98% CH$_3$CN 0.1% TFA;
64-80 min: 2% H$_2$O 0.1% TFA; 98% CH$_3$CN 0.1% TFA;
80-83 min: 60% H$_2$O 0.1% TFA; 40% CH$_3$CN 0.1% TFA;
83-89 min: 60% H$_2$O 0.1% TFA; 40% CH$_3$CN 0.1% TFA;
89-90 min: 60% H$_2$O 0.1% TFA; 40% CH$_3$CN 0.1% TFA.
HPLC-MS (m/z) [M]$^+$ calcd 470.27, found 470.49.

Example 15: Analytical Derivatization of Testosterone Using Labels 1 to 6

A 500 ng/ml solution (S1) of Testosterone was prepared in methanol. A solution (S2) compared to the solution (S) containing an excess of either of the derivatization reagents Labels 1 to 12, diluted in methanol (molar ratio >1000) was added and the solution was acidified with glacial acidic acid (20% v/v). The solution S1 and S2 were mixed resulting in solution S3, and held for 2 h at 65° C. followed by 12 h at room temperature. After 12 h the solution S3 was diluted with methanol to give five independent concentration levels based on the molecular mass of testosterone of 1 eq testosterone, 1/20 eq testosterone, 1/40 eq testosterone; 1/100 eq testosterone and 1/200 eq testosterone. The 1 eq is chosen to be still in a linear range of the detector and the 1/200 eq testosterone below the detection limit of the used instrument. As example the following concentrations has been used for a Waters Quattro Micro system (100 ng/ml; 5 ng/ml; 2.5 ng/ml: 1 ng/ml; 500 pg/ml). A blank solution of 0 ng/ml was prepared by using the solution S2.

After derivatization of the analyte molecule, isomers may derive which often result in multiple peaks. The chromatographic behaviour of those isomers need to be addressed in a way to relatively quantify their properties. Exemplified FIG. 1 describes the signal distribution in % over time applying a certain chromatographic method in 5% of the absolute peak height. The parameter of "splitting" describes the capability of the chromatographic system to separate the derivatization reaction resulting isomers of the analyte molecule. The retention time measured in the barycentre of the isomers peak can describe the polarity of the resulting derivative if reverse phase chromatographic material is used for separation. The area A1 and A2 are measured in signal counts*min and reported as their ratio for the resulting derivation isomers respectively. If the ratio of the Peaks A1 and A2 are 50/50 the resulting isomers have been produced in equal amounts. If the label can affect this ration to be unequal to 50/50, then one isomer is predominantly produced. The signal intensities are therefore unequal distributed and will enhance therefor the signal height against the unaffected background noise.

For every labeling substance the respective testosterone derivate has been measured by electrospray ionization mass spectrometry after liquid chromatography separation and different fragmentation scans with collision energies of 15V, 20V, 25V, 30V, 35V and 40V have been performed.

The mass signal of the molecular ion peak and the most abundant fragment ion peak (neutral loss) has been used for fragmentation optimization. The fragmentation energy is one of the most important tuning parameter if it comes to signal gain for charged molecules with neutral loss unit. The fragmentation energy is critical because the molecule need to be un-cleaved during the source and further ion path conditions. The cleaving or cleavage of the neutral loss fragment should only occur in the collision cell (and or related devices) to form a certain fragment of interest. If the collision energy needs to be very high for the cleavage of the neutral loss fragment also other unwanted fragmentation paths can occur which results in a loss of signal intensity for the neutral loss fragmentation path. Therefor the collision energy is supposed too be not to small and not too large to obtain optimal fragmentation behavior. The maximum in area counts by the respective collision energy has been used for further detection limit quantification approaches.

For every labeling substance the respective testosterone derivate has been tuned on a triple quadrupole mass spectrometer by injecting it via liquid chromatography into the mass spectrometer. The tuning parameter was the collision energy which resulted in the highest signal of the respective chromatographic peak of five independent collision energy experiments.

Chromatographic and MS Parameters

Polarity ES+
Calibration Static 2
Soft Transmission Mode Disabled
Capillary (kV)3.00 3.14
Cone (V) 50.00 144.92
Source Offset (V) 30.0
Source Temperature (° C.) 140 140
Desolvation Temperature (° C.) 350 350
Cone Gas Flow (L/Hr) 150 149
Desolvation Gas Flow (L/Hr) 1000 990
Collision Gas Flow (mL/Min) 0.15 0.14
Nebuliser Gas Flow (Bar) 7.00 6.52
LM 1 Resolution 3.0
HM 1 Resolution 15.0
Ion Energy 1 −0.2
MS Mode Collision Energy 4.00
MSMS Mode Collision Energy 2.00
MS Mode Entrance 1.00
MS Mode Exit 1.00
Gas On MS Mode Entrance 1.00
Gas On MS Mode Exit 1.00
Gas On MSMS Mode Entrance 1.00
Gas On MSMS Mode Exit 1.00
Gas Off MS Mode Entrance 30.00
Gas Off MS Mode Exit 30.00
Gas Off MSMS Mode Entrance 30.00
Gas Off MSMS Mode Exit 30.00
ScanWave MS Mode Entrance 1.00
ScanWave MS Mode Exit 1.00
ScanWave MSMS Mode Entrance 1.00
ScanWave MSMS Mode Exit 1.00
LM 2 Resolution 3.0
HM 2 Resolution 15.0
Ion Energy 2 0.2
Gain 1.00
Multiplier 513.80
Active Reservoir C
Cone Energy Ramp: Disabled
Probe Temperature Ramp: Disabled
Collision Energy Ramp: Disabled
Instrument Parameters - Function 2:
Parameter File - E:\Regulated projects\ESI-Derivatization_PDA.PRO\ACQUDB\cz20Mrz2019-testo-label-general_tuning.IPR
Polarity ES+
Calibration Static 2
Soft Transmission Mode Disabled
Capillary (kV)3.00 3.14
Cone (V) 50.00 144.92
Source Offset (V) 30.0
Source Temperature (° C.) 140 140
Desolvation Temperature (° C.) 350 350

-continued

Cone Gas Flow (L/Hr) 150 149
Desolvation Gas Flow (L/Hr) 1000 990
Collision Gas Flow (mL/Min) 0.15 0.14
Nebuliser Gas Flow (Bar) 7.00 6.52
LM 1 Resolution 3.0
HM 1 Resolution 15.0
Ion Energy 1 −0.2
MS Mode Collision Energy 4.00
MSMS Mode Collision Energy 2.00
MS Mode Entrance 1.00
MS Mode Exit 1.00
Gas On MS Mode Entrance 1.00
Gas On MS Mode Exit 1.00
Gas On MSMS Mode Entrance 1.00
Gas On MSMS Mode Exit 1.00
Gas Off MS Mode Entrance 30.00
Gas Off MS Mode Exit 30.00
Gas Off MSMS Mode Entrance 30.00
Gas Off MSMS Mode Exit 30.00
ScanWave MS Mode Entrance 1.00
ScanWave MS Mode Exit 1.00
ScanWave MSMS Mode Entrance 1.00
ScanWave MSMS Mode Exit 1.00
LM 2 Resolution 3.0
HM 2 Resolution 15.0
Ion Energy 2 0.2
Gain 1.00
Multiplier 513.80
Active Reservoir C
Cone Energy Ramp: Disabled
Probs Temperature Ramp: Disabled
Collision Energy Ramp: Disabled
Engineers Settings:
MS1 Low Mass Position 673
MS1 High Mass Position 335
MS1 Low Mass Resolution 215
MS1 High Mass Resolution 2152
MS1 Resolution Linearity 531
MS1 High Mass DC Balance 0.07
MS1 DC Polarity Negative
MS2 Low Mass Position 672
MS2 High Mass Position 291
MS2 Low Mass Resolution 219
MS2 High Mass Resolution 2162
MS2 Resolution Linearity 528
MS2 High Mass DC Balance 0.50
MS2 DC Polarity Negative
Inter-scan delays:
Automatic Mode
MS Inter-scan delay (secs) 0.003
Polarity/Mode switch Inter-scan delay (secs) 0.020
Enhanced Inter-scan delay (secs) 0.020
Inter-channel delay - See Tables MS 1 Delay Table:

| R | delay |
|---|---|
| <=1.250 | 0.001 |
| <=4.000 | 0.002 |
| <=10.000 | 0.003 |
| <=20.000 | 0.004 |
| >20.000 | 0.005 |

-------------------- Run method parameters ----------------
Waters Acquity SDS
Run Time: 6.50 min
Comment:
Solvent Selection A: A2
Solvent Selection B: B1
Low Pressure Limit: 0.000 bar
High Pressure Limit: 1034.200 bar
Solvent Name A: Water + NH4Ac + 0.1% formic acid
Solvent Name B: MeOH + NH4Ac + 0.1% formic acid
Switch 1: No Change
Switch 2: No Change
Switch 3: No Change
Seal Wash. 5.0 min
Chart Out 1: System Pressure
Chart Out 2: % B
System Pressure Data Channel: Yes
Flow Rate Data Channel: No
% A Data Channel: No
% B Data Channel: Yes
Primary A Pressure Data Channel: No
Accumulator A Pressure Data Channel: No
Primary B Pressure Data Channel: No
Accumulator B Pressure Data Channel: No
Degasser Pressure Data Channel: No

[Gradient Table]

| Time(min) | Flow | Rate | % A | % B | Curve |
|---|---|---|---|---|---|
| 1. | Initial | 0.400 | 60.0 | 40.0 | Initial |
| 2. | 0.50 | 0.400 | 60.0 | 40.0 | 6 |
| 3. | 3.00 | 0.400 | 10.0 | 90.0 | 6 |
| 4. | 5.00 | 0.400 | 10.0 | 90.0 | 6 |
| 5. | 5.10 | 0.400 | 60.0 | 40.0 | 6 |
| 6. | 6.50 | 0.400 | 60.0 | 40.0 | 6 |

Run Events: Yes
Gradient Start (Relative to Injection): 0 uL
2D Repeat: No
Waters Acquity PDA
Run Time: 6.50 min
PDA Detector Type: UPLC LG 500 nm
Lamp: On
Sampling Rate: 10 points/sec
Filter Time Constant: 0.2000 sec
Exposure Time: Auto msec
Interpolate 2nd order filter Region: No
Use UV Blocking Filter: No
3D Channel . . .
Range: 200-400
Resolution: 2.4 nm
Initial Switch 1: No Change
Initial Switch 2: No Change
Waters ACQUITY FTN AutoSampler
Run Time: 6.50 min
Comment:
Load Ahead: Disabled
Loop Offline: Automatic min
Wash Solvent Name: ACN: water
Pre-Inject Wash Time: 15.0 sec
Post-Inject Wash Time: 15.0 sec
Purge Solvent Name: ACN: water
Dilution: Disabled
Dilution Volume: 0 uL
Delay Time: 0 min
Dilution Needle Placement: Automatic mm
Target Column Temperature: 40.0 C.
Column Temperature Alarm Band: Disabled
Target Sample Temperature: 6.0 C.
Sample Temperature Alarm Band: Disabled
Syringe Draw Rate: Automatic
Needle Placement: 0.5 mm
Pre-Aspirate Air Gap: Automatic
Post-Aspirate Air Gap: Automatic
Column Temperature Data Channel: No
Room Temperature Data Channel: Yes
Sample Temperature Data Channel: Yes
Sample Organiser Temperature Data Channel: No
Sample Pressure Data Channel: No
Preheater Temperature Data Channel: No
Seal Force Data Channel: No
No Injection Mode Enabled: No
Autoaddition Mix Stroke Cycles: Automatic
Autoaddition Mix Stroke Volume: Automatic uL
Active Preheater: Use Console Configuration
Run Events: No
Sample Run Injection Parameter
Injection Volume (ul) - 5.00
Function 1
Scans in function: 738
Cycle time (secs): Automatic
Inter Scan Delay (secs): Automatic
Inter Channel Delay (secs): Automatic

```
Span (Da): 0.500
Start and End Time(mins): 0.000 to 5.000
Ionization mode: ES+
Data type: Enhanced SIR or MRM
Function type: MRM of 1 channel
Chan Reaction Dwell(secs) Cone Volt. Col. Energy Delay(secs)
Compound
1: 289.25 > 108.78 0.200 Tune 25.0 Auto Testosterone
Function 2
Scans in function: 737
Cycle time (secs): Automatic
Inter Scan Delay (secs): Automatic
Inter Channel Delay (secs): Automatic
Span (Da): 0.500
Start and End Time(mins): 0.000 to 5.000
Ionization mode: ES+
Data type: Enhanced SIR or MRM
Function type: MRM of 1 channel
Chan Reaction Dwell(secs) Cone Volt. Col. Energy Delay(secs)
Compound Formula|Mass
1: 624.40 > 203.00 0.200 Tune 40.0 Auto DMA041
CE40 420.2
Function 3
Scans in function: 3901
Function type: Diode Array
Wavelength range (nm): 200 to 400
```

Figure 2:
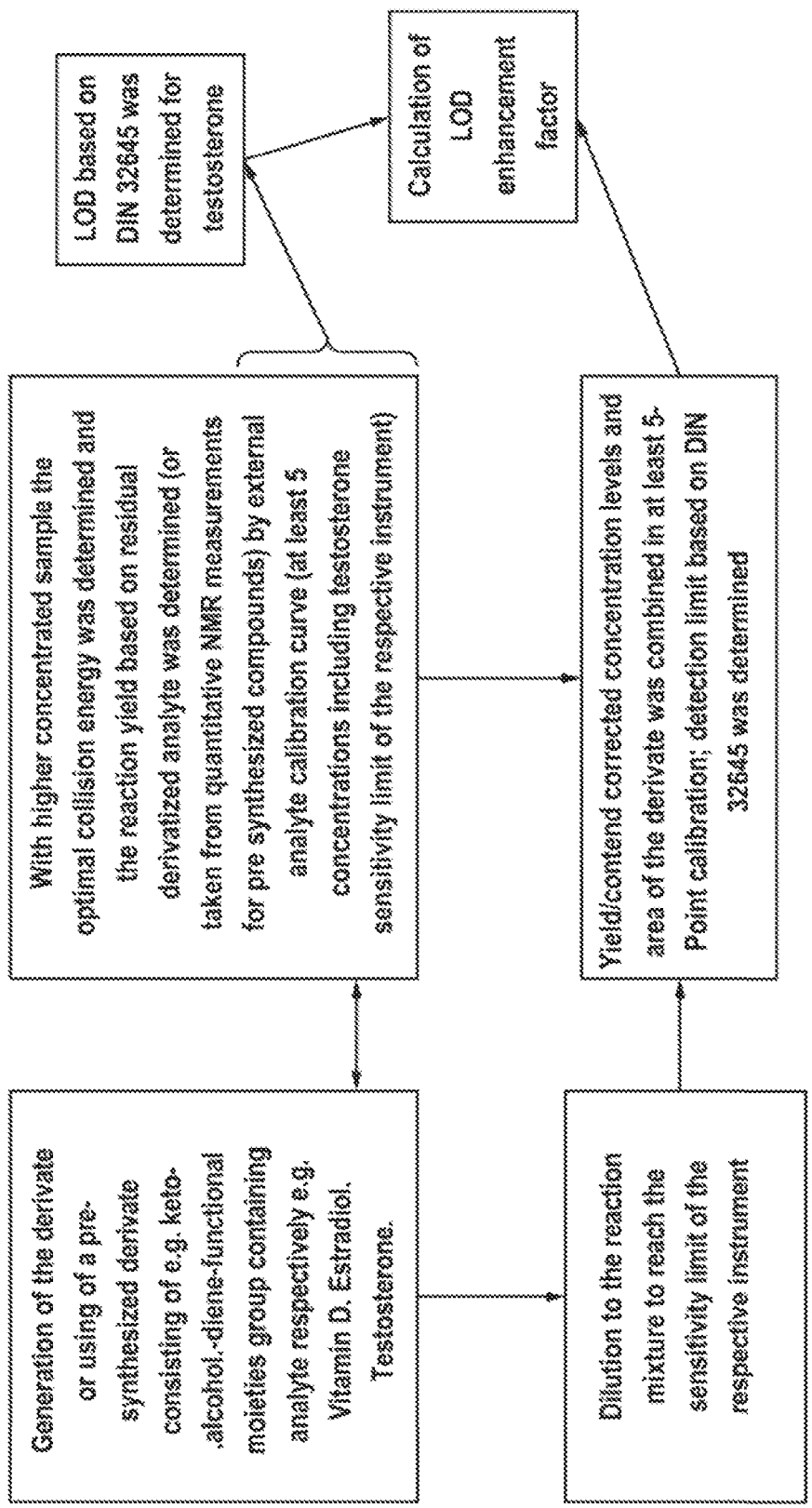
FIG. 2 shows schematic representation of the workflow determining the Enhancement Factor of the derivatized/labeled analyte in comparison to underivatized analyte, e.g. testosterone, or Amplifex derivatized analyte, e.g. Amplifex derivatized testosterone.

From linear calibration curves the respective detection limits were obtained by using the procedure described in DIN EN ISO 32645. Enhancement factors are calculated based upon the labeled analyte Limit of Detection (LOD), here the labeled testosterone Limit of Detection (LOD), in comparison to the underivatized analyte LOD, here the underivatized testosterone LOD. The workflow is shown in FIG. 2. Results are shown in Table 2 below.

TABLE 2

Results for the specific labels

| Label | Enhancement factor to underivatized Testosterone (Mean) n: | Retention Time [min] | Peak Splitting [min] | Peak Width [min] | Loss fragment | Optimized fragmentation energy [V] | Ratio A1/A2 Isomer |
|---|---|---|---|---|---|---|---|
| Testosterone underivatized | 1 | 2.82 | 0 | 0.2 | Testosterone structure element | 25 | n.z. |
| Amphifex Sciex | 22 | 2.35 | 0.11 | 0.5 | NMe3 | 20 | 51/49 |
| 2 | 60 | 2.48 | 0.13 | 0.25 | Testo-Linker-Pyridine | 35 | 30/70 |
| 4 | 19 | 3.38 | 0.06 | 0.17 | Testo-Linker-Pyridine | 40 | 30/70 |
| 5 | 50 | 2.78 | 0.10 | 0.17 | Testo-Linker-Pyridine | 30 | 30/70 |
| 6 | 60 | 2.40 | 0.11 | 0.23 | Testo-Linker-Pyridine | 30 | 30/70 |
| 1 | 46 | 2.41 | 0.12 | 0.26 | Testo-Linker-Pyridine | 35 | 30/70 |

As it can be seen from Table 2, labels 1, 2 and 4 to 6 and complexes thereof exhibit a signal enhancement compared to the non derivatized analyte. These labels and complexes thereof show a better enhancement factor than the state of the art derivation agents e.g. Amplifex from Sciex.

Example 16: Analytical Derivatization of Estradiol Using Labels 10 to 12

A 500 pg ml solution (S1) of estradiol was prepared in acetonitrile. Horse serum was depleted using acetonitrile (−20° C.) in a ratio of 1 mL horse serum+3 mL acetonitrile. The horse serum/acetonitrile-mixture was mixed and centrifuged and the supernatant was transferred resulting in solution (S2). The solution S1 and S2 were mixed in a ratio of 1:5 resulting in solution S3. A solution (S4) compared to the solution (S3) containing an excess of either of the derivatization reagents labels 10 to 12, diluted in methanol (molar ratio >1000) was added. A solution of 5 µg/mL $K_2CO_3$ (S5) was prepared in acetonitrile/H2O 90/10+0.1% formic acid. The solutions S3, S4 and S5 were mixed resulting in solution S6 and held for 1 h at 50° C. followed by 12 h at room temperature. The solution S6 was diluted with acetonitrile/$H_2O$+0.1% formic acid to give appropriate concentration levels for quantification.

From linear calibration curves the respective detection limits were obtained by using the procedure described in DIN EN ISO 32645. Enhancement factors are calculated based upon the labeled estradiol Limit of Detection (LOD) in comparison to the underivatized estradiol LOD. Results are shown in Table 3 below.

TABLE 3

| | Results for the specific label 10 to 11 | | | | |
|---|---|---|---|---|---|
| Label | Enhancement factor to underivatized Estradiol (Mean) | Retention Time [min] | Peak Width [min] | Loss fragment | Optimized fragmentation energy [V] |
| Estradiol underivatized | 1 | 2.71 | 0.07 | 274 → 148 | 40 |
| 10 | 63 | 2.81 | 0.06 | 513.3 → 121.07 | 35 |
| | | | | 513.3 → 91.05 | 65 |
| 11 | 200 | 2.51 | 0.07 | 573.3 → 181.1 | 25 |

As it can be seen from Table 3, labels 10 and 11 and complexes thereof exhibit a signal enhancement compared to the non derivatized analyte.

Example 17: Analytical Derivatization of Vitamin D Using Labels 7 and 8

A 500 pg/ml solution (S) of 25-OH vitamin D3 was prepared in methanol. Horse serum was depleted using methanol (−20° C.) in a ratio of 1 mL horse serum+3 mL methanol. The horse serum/methanol-mixture was mixed and centrifuged and the supernatant was transferred resulting in solution (S2). The solution S1 and S2 were mixed in a ratio of 1:5 resulting in solution S3. Solution S3 was concentrated to dryness. A solution (S4) compared to the solution (S3) containing an excess of either of the derivatization reagents labels 7 to 8, diluted in methanol (molar ratio >1000) was added and the resulting solution was mixed. A solution of iodobenzene diacetate in methanol with 2 mg/mL (S5) was added and the resulting solution (S6) was stirred for 2 min at 40° C. The solution S6 was diluted with methanol/H2O+0.1% formic acid to give appropriate concentration levels for quantification.

TABLE 4

Results for the specific labels

| Label | Enhancement factor to underivatized Vitamin D (Mean) | Retention Time [min] | Peak Width [min] | Loss fragment | Optimized fragmentation energy [V] |
|---|---|---|---|---|---|
| 25-OH Vitamin D3 underivatized | 1 | 4.12 | | | |
| 7 | 12500 | 3.08 | 0.13 | 697.3 → 240.9 | 30 |
| | | | | 697.3 → 120.7 | 35 |
| 8 | 1500 | 2.83 | 0.06 | 591.4 → 192.9 | 30 |
| | | | | 591.4 → 134.7 | 30 |

As it can be seen from Table 4, labels 7 and 8 and complexes thereof exhibit a signal enhancement compared to the non derivatized analyte.

Beside testosterone, estradiol and vitamin D, other analytes can be chosen as the analyte of interest. Complexes with these others analytes exhibit a signal enhancement compared to the non derivatized analyte.

This patent application claims the priority of the European patent application 20175801.8, wherein the content of this European patent application is hereby incorporated by references.

The invention claimed is:

1. A compound of formula I for mass spectrometric determination of an analyte:

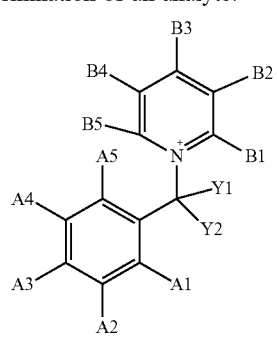

(I)

wherein one of the substituents B1, B2, B3, B4, B5 is a coupling group Q, which is capable of forming a covalent bond with the analyte, wherein the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof, wherein Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

2. The compound of claim 1, wherein the coupling group Q is bonded to X according to the following formula II:

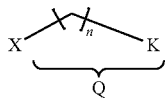

(II)

wherein K is a reactive unit, which is capable of forming the covalent bond with the analyte,
wherein n is 0, 1, 2, 3, 4 or 5, and
wherein X is a binding carbon-atom of the pyridinium cation of formula I.

3. The compound of claim 2, wherein K is capable of reacting with a carbonyl group, phenol group, amine, hydroxyl group or diene group of the analyte.

4. The compound of claim 2, wherein K is selected from the group consisting of hydrazide, hydrazine, hydroxylamine, Br, F, 4-substituted 1,2,4-triazolin-3,5-dione (TAD) and carbamate.

5. The compound of claim 2, wherein n =0 and K is Br or n=0 and K is F.

6. The compound of claim 1, wherein Q is selected from the group consisting of methyl hydrazide, methyl hydrazine, methyl hydroxylamine, acetohydrazide, 4-substituted 1,2,4-triazoline-3,5-dione (TAD) and F.

7. The compound of claim 1, wherein B1 is Q or B2 is Q or B3 is Q.

8. The compound of claim 1, wherein the compound is permanent positively charged.

9. A composition comprising the compound of claim 1.

10. A kit comprising the compound of claim 1.

11. A complex for detecting an analyte using mass spectrometric determination comprising a binding analyte and a binding compound, which are covalently linked to each other, wherein the complex is formed by chemical reaction of the analyte and the compound of claim 1, and wherein the analyte is selected from the group consisting of a nucleic acid, an amino acid, a peptide, a protein, a metabolite, a hormone, a fatty acid, a lipid, a carbohydrate, a steroid, a ketosteroid, a secosteroid, a molecule characteristic of a certain modification of another molecule, a substance that has been internalized by the organism, and a metabolite of such a substance, and combinations thereof.

12. The complex of claim 11, wherein the binding compound comprises the formulae III and IV:

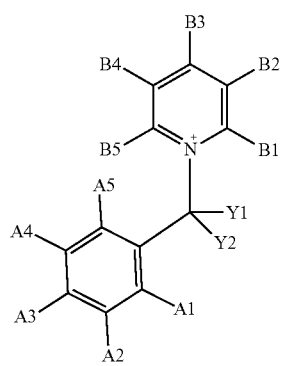

(III)

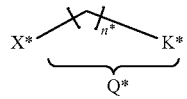

(IV)

wherein one of the substituents B1, B2, B3, B4, B5 is a coupling group Q*, which forms a covalent bond with the analyte, wherein the other substituents A1, A2, A3, A4, A5, B1, B2, B3, B4, B5 are each independently selected from hydrogen, halogen, alkyl, N-acylamino, alkoxy, thioalkoxy, hydroxy, cyano, alkoxycarbonyl, alkoxythiocarbonyl, acyl, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, isotope or derivative thereof, wherein Y1 and Y2 are each independently selected from hydrogen, methyl, ethyl, methoxy, amine or wherein Y1 and Y2 form a ring structure, which is selected from substituted cycloalkyl, unsubstituted cycloalkyl, substituted aromatic, benzylic, unsubstituted aromatic, substituted heteroaromatic, unsubstituted heteroaromatic, wherein n* is 0, 1, 2, 3, 4 or 5, wherein the binding analyte is covalently bonded via K*, this is true for pyridinium-hydrazide and pyridinium-1,2,4-triazoline-3,5-dione, but in the case of fluoropyridinium K*=X* and n*=0, and wherein X* is a binding carbon-atom of the pyridinium cation of formula III.

13. A method for mass spectrometric determination of an analyte comprising the steps of:

(a) reacting the analyte with the compound of formula I as defined in claim 1, whereby a complex is formed, (b) subjecting the complex from step (a) to a mass spectrometric analysis, wherein step (b) comprises:

(i) subjecting an ion of the complex to a first stage of mass spectrometric analysis, whereby the ion of the complex is characterized according to its mass/charge (m/z) ratio, (ii) causing fragmentation of the complex ion, whereby a first entity is released and a daughter ion of the complex is generated, wherein the daughter ion of the complex differs in its m/z ratio from the complex ion, and (iii) subjecting the daughter ion of the complex to a second stage of mass spectrometric analysis, whereby the daughter ion of the complex is characterized according to its m/z ratio, and/or wherein (ii) may further comprise alternative fragmentation of the complex ion, whereby a second entity different from the first entity is released and a second daughter ion of the complex is generated, and wherein (iii) may further comprise subjecting the first and second daughter ions of the complex to a second stage of mass spectrometric analysis, whereby the first and second daughter ions of the complex are characterized according to their m/z ratios.

14. A compound of formula V:

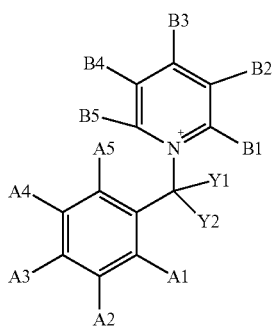

(V)

wherein one of the substituents B1, B2, B3, B4, B5 is a coupling group Q, which is capable of forming a covalent bond with the analyte, wherein the other substituents A1, A2, A3, A4, A5, B1, B2, B3, B4, B5 are each independently selected from hydrogen, halogen, alkyl, N-acylamino, N,N-dialkylamino, alkoxy, thioalkoxy, hydroxy, cyano, alkoxycarbonyl, alkoxythiocarbonyl, acyl, nitro, thioacyl, aryloyl, fluoromethyl, difluoromethyl, trifluoromethyl, trifluoroethyl, cyanomethyl, cyanoethyl, hydroxyethyl, methoxyethyl, nitroethyl, acyloxy, aryloyloxy, cycloalkyl, aryl, heteroaryl, heterocycloalkyl, amino, isotope or derivative thereof, wherein Y1 and Y2 are each independently selected from hydrogen, methyl, ethyl, methoxy, substituted aromatic, unsubstituted aromatic, substituted cycloalkyl, unsubstituted cycloalkyl, substituted heteroaromatic, unsubstituted heteroaromatic, amine or wherein Y1 and Y2 form a ring structure, which is selected from substituted cycloalkyl, unsubstituted cycloalkyl, substituted aromatic, unsubstituted aromatic, substituted heteroaromatic, unsubstituted heteroaromatic.

* * * * *